United States Patent
Vasudevan et al.

(10) Patent No.: US 9,212,192 B2
(45) Date of Patent: Dec. 15, 2015

(54) BICYCLIC CARBOXAMIDE INHIBITORS OF KINASES

(75) Inventors: Anil Vasudevan, Union Grove, WI (US); Thomas Dale Penning, Elmhurst, IL (US); Huanming Chen, Irvine, CA (US); Bo Liang, Beijing (CN); Shaohui Wang, Beijing (CN); Fengchun Wu, Beijing (CN); Yan Shen, Beijing (CN); Cuihua Liu, Beijing (CN); Zhenguang Zou, Beijing (CN); Marina Pliushchev, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/979,387

(22) PCT Filed: Jan. 20, 2012

(86) PCT No.: PCT/CN2012/000103
§ 371 (c)(1),
(2), (4) Date: Mar. 20, 2014

(87) PCT Pub. No.: WO2012/097684
PCT Pub. Date: Jul. 26, 2012

(65) Prior Publication Data
US 2014/0194418 A1    Jul. 10, 2014

(30) Foreign Application Priority Data
Jan. 21, 2011  (WO) ................ PCT/CN2011/000109

(51) Int. Cl.
C07D 487/04 (2006.01)
A61K 31/4353 (2006.01)
A61P 35/00 (2006.01)
C07D 519/00 (2006.01)
C07D 471/04 (2006.01)

(52) U.S. Cl.
CPC .......... *C07D 519/00* (2013.01); *A61K 31/4353* (2013.01); *C07D 471/04* (2013.01); *C07D 487/04* (2013.01)

(58) Field of Classification Search
CPC .. C07D 487/04; C07D 401/12; C07D 401/14; C07D 403/12; C07D 403/14; A61K 31/4353
USPC ........................................... 546/118; 514/303
See application file for complete search history.

(56) References Cited

PUBLICATIONS

Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ferrara, N, Oncology, 69 Suppl. 3, 11-16, 2005.*
Jain et al., Nature Clinical Practice Oncology, 3(1), 24-40, 2006.*
Gautschi et al., Clin. Cancer Res., 14(6), 1639-1648, 2008.*
Mountzios et al., Cancer Treatments Reviews, 34, 175-182, 2008.*
Qiu Y., Oncogene 19, 5651-5661,2000.*
Pyne et al. Cancer Res 2011 ;71:6576-6582.*
Supplementary European Search Report for EP12736701 mailed May 16, 2014.
Andini E. et al., Anaplastic Lymphoma Kinase: Role in Specific Tumors, and Development of Small Molecule Inhibitors for Cancer Therapy, Cancer Letters, 2010, 229(2): 81-94.
Coopman P.J.P. et al, The Syk Tyrosine Kinase Suppresses Malignant Growth of Human Breast Cancer Cells, Nature, 2000, 406: 742-747.

* cited by examiner

*Primary Examiner* — Venkataraman Balasubramanian
(74) *Attorney, Agent, or Firm* — Changxia Sun

(57) ABSTRACT

Compounds of formula (I) or pharmaceutical acceptable salts are provided, wherein $X^1 \sim X^5$, $R^1 \sim R^3$, A, B, Z and n are defined in the description. And compositions containing said compounds, and the uses for inhibitors of kinases such as ALK, and the uses for treating cancer thereof are provided.

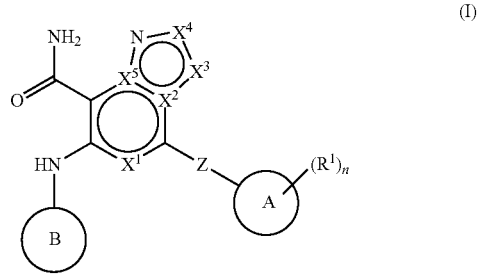

14 Claims, No Drawings

BICYCLIC CARBOXAMIDE INHIBITORS OF KINASES

FIELD OF THE INVENTION

This invention pertains to compounds which inhibit the activity of anaphastic lymphoma kinase (ALK), methods of making the compounds, compositions containing the compounds, and methods of treatment using the compounds.

BACKGROUND OF THE INVENTION

Signaling through receptor tyrosine kinases (RTKs) regulates and fine-tunes many processes including cell growth, proliferation, differentiation, and apoptosis. The improper activation of RTKs is involved in the pathogenesis, growth, and metastasis of many cancers. The receptor tyrosine kinase ALK (Anaplastic Lymphoma Kinase) is a member of the insulin receptor superfamily that was initially identified from the t(2;5)(p23;q35) translocation in anaplastic large cell lymphoma (ALCL) (Fischer, P., et al. Blood, 72: 234-240. (1988)). The protein product of this translocation is ALK fused to nucleophosmin (NPM) (Morris et al., 1994). When fused to ALK, the dimerization domain of NPM results in constitutive dimerization and activation of ALK (reviewed in Chiarle, R., Nature reviews, 8:11-23 (2008)). Once activated, ALK recruits several adaptor proteins and stimulates multiple signaling pathways known to mediate tumor cell growth and survival including STAT3, PLC-γ, RAS-ERK1,2, and PI3K-AKT (Bai, R. Y., et al. Molecular and cellular biology 18: 6951-6961 (1998); Bai, R. Y., et al. Blood 96:4319-4327 (2000); Chiarle, R., et al. Nature medicine 11:623-629 (2005); Pulford, K., et al. Journal of cellular physiology 199: 330-358 (2004)). The dysregulation of ALK is highly oncogenic, as it is sufficient to induce cell transformation in a several immortalized cell lines (Bischof, D., et al. Molecular and cellular biology 17:2312-2325 (1997); Fujimoto, J., et al. Proceedings of the National Academy of Sciences of the United States of America 93: 4181-4186 (1996)) and to form tumors in animal models (Chiarle, R., et al. Blood 101: 1919-1927 (2003); Kuefer, M. U., et al. Blood 90: 2901-2910 (1997)). Moreover, NPM-ALK drives tumor formation, proliferation and survival in ALCL (reviewed in (Duyster, J., et al. Oncogene 20: 5623-5637 (2001)).

More recently, ALK translocations have been detected in ~5% of non-small cell lung cancers (NSCLC). Similar to ALK translocations in ALCL, the fusion proteins in NSCLC display constitutive ALK activity and drive tumor growth and survival (Soda et al., Nature 448: 561-566 (2007); Soda et al., Proceedings of the National Academy of Sciences of the United States of America 105: 19893-19897 (2008)). NSCLC tumors harboring ALK translocations are mutually exclusive from K-Ras or EGFR aberrations and predominantly occur in younger patients that are non-smokers (Rodig et al., Clin Cancer Res 15: 5216-5223 (2009); Shaw et al., J Clin Oncol 27: 4247-4253 (2009); Wong et al., Cancer 115: 1723-1733 (2009)). In addition to chromosomal rearrangements, activating point mutations and amplifications have been reported in a subset of sporadic and familial neuroblastomas, further expanding the spectrum of tumors dependent on ALK activity (Chen et al., Nature 455: 971-974 (2008); George et al., Nature 455: 975-978 (2008); Janoueix-Lerosey et al., Nature 455: 967-970 (2008); Mosse et al., Nature 455: 930-935 (2008)). Neuroblastomas with ALK genetic aberrations also are dependent on ALK for proliferation and survival, and cells expressing ALK containing activating mutations form tumors in animal models.

Inhibitors of RTKs have the potential to cause lethality in cancerous cells that are reliant on deregulated RTK activity while sparing normal tissues. Thus, small molecule inhibitors of ALK would be beneficial for therapeutic intervention in ALCL, NSCLC, neuroblastoma, and other cancers that are dependent on ALK for growth and survival.

SUMMARY OF THE INVENTION

The present invention has numerous embodiments. One embodiment of this invention, therefore, pertains to compounds that have formula (I).

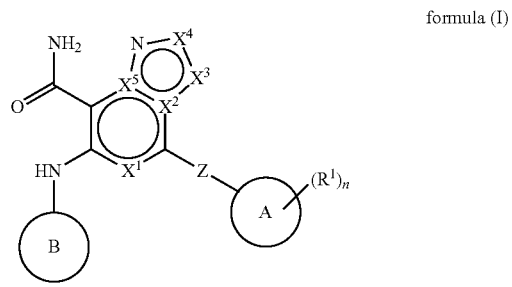

formula (I)

wherein $X^1$, $X^2$, $X^3$, $X^4$, $X^5$, $R^1$, $R^2$, $R^3$, A, B, Z, and n are as defined below and subsets therein.

Also provided are pharmaceutically acceptable compositions, comprising a therapeutically effective amount of a compound of formula (I) and a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). Another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$—$C_y$—", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$— prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Embodiments of Formula (I)

In one embodiment, the present invention is directed, in part, to a class of compounds having a structure of Formula I

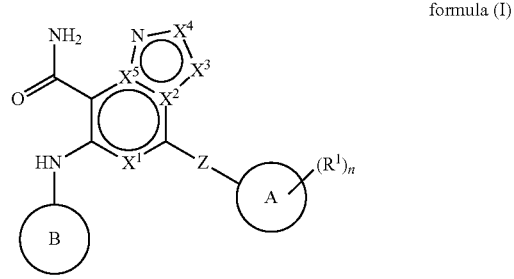

formula (I)

wherein $X^2$ is N, $X^5$ is C, $X^1$, $X^3$, and $X^4$ are CH; or
  $X^1$ and $X^2$ are N, $X^5$ is C, and $X^3$ and $X^4$ are $CR^4$; or
  $X^1$ and $X^3$ are N, $X^2$ and $X^5$ are C, and $X^4$ is $CR^{14}$; or
  $X^1$, $X^2$, and $X^4$ are N, Xs is C, and $X^3$ is $CR^{14}$; or
  $X^1$, $X^2$, $X^3$, and $X^4$ are N and $X^5$ is C; or
  $X^1$ and $X^5$ are N, $X^2$ is C, and $X^3$ and $X^4$ are CH;

A is phenyl, naphthyl, indenyl, $C_{3-8}$ cycloalkyl, 5-7 membered heterocycloalkyl, 5-7 membered heterocycloalkenyl, or 5-7 membered heteroaryl;

B is phenyl, pyridinyl, pyrimidinyl, pyrazinyl, pyridazinyl, or pyrazolinyl, wherein B is optionally substituted with one, two, three, or four $R^2$ and is substituted with $R^3$; or
  B is 1,2,3,4-tetrahydroisoquinoline;

Z is a bond, $C_{1-6}$ alkylene, or $C_{2-6}$ alkenylene;

$R^1$, at each occurrence, is independently selected from the group consisting of halo, CN, $NO_2$, $C_{1-6}$-alkyl, $C_{1-6}$-haloalkyl, aryl, $C_{3-8}$ cycloalkyl, heteroaryl, heterocycloalkyl, $OR^5$, $SR^5$, $C(O)R^5$, $C(O)NR^6R^7$, $C(O)OR^5$, $OC(O)R^5$, $OC(O)NR^6R^7$, $NR^6R^7$, $NR^6C(O)R^5$, $S(O)R^5$, $S(O)NR^6R^7$, S(O)$_2$R$^5$, NR$^6$S(O)$_2$R$^3$, and S(O)$_2$NR$^6$R$^7$; wherein the C$_{3-8}$ cycloalkyl, aryl, heterocycloalkyl, and heteroaryl are optionally substituted with 1, 2, or 3 substituents independently selected from halo, C$_{1-4}$ alkyl, C$_{1-4}$ haloalkyl, CN, NO$_2$, OR$^a$, SR$^a$, C(O)R$^a$, C(O)NR$^b$R$^a$, C(O)OR$^a$, OC(O)R$^a$, OC(O)NR-$^b$R$^c$, NR$^b$R$^c$, NR$^b$C(O)R$^a$, S(O)R$^a$, S(O)NR$^b$R$^c$, S(O)$_2$R$^a$, NR$^b$S(O)$_2$R$^a$, and S(O)$_2$NR$^b$R$^c$;

R$^2$, at each occurrence, is independently selected from the group consisting of halo, CN, OH, C$_{1-4}$ alkyl, C$_{1-4}$-haloalkyl, C$_{1-4}$ alkoxy, C$_{1-4}$ haloalkoxy, C$_{1-4}$-thioalkoxy, —S(O)C$_{1-4}$ alkyl; amino, C$_{1-4}$ alkylamino, and C$_{1-4}$ dialkylamino;

R$^3$ is selected from the group consisting of aryl, C$_{3-8}$ cycloalkyl, heteroaryl, heterocycloalkyl, aryl-C$_{1-6}$-alkyl-, C$_{3-8}$ cycloalkyl-C$_{1-6}$-alkyl-, heteroaryl-C$_{1-6}$-alkyl-, heterocycloalkyl-C$_{1-6}$-alkyl-, OR$^8$, C(O)R$^8$, —CH$_2$C(O)R$^8$, C(O)NR$^9$R$^{10}$, C(O)OR$^8$, OC(O)R$^8$, OC(O)NR$^9$R$^{10}$, NR$^9$R$^{10}$, NR$^9$C(O)R$^8$, S(O)R$^8$, S(O)NR$^9$R$^{10}$, S(O)$_2$R$^8$, NR$^9$S(O)$_2$R$^8$, and S(O)$_2$NR$^9$R$^{10}$, wherein the C$_{3-8}$ cycloalkyl, aryl, heterocycloalkyl, and heteroaryl, alone or part of another moiety, are optionally substituted with one, two, or three R$^{11}$;

R$^4$ is H or C$_{1-6}$-alkyl;

R$^5$, R$^6$, and R$^7$, at each occurrence, are independently selected from H, C$_{1-8}$ alkyl, C$_{1-6}$ haloalkyl, aryl, C$_{3-8}$ cycloalkyl, heteroaryl, and heterocycloalkyl, wherein the aryl, C$_{3-8}$ cycloalkyl, heteroaryl, and heterocycloalkyl moiety are optionally substituted with 1, 2, or 3 substituents independently selected from halo, CN, OH, C$_{1-4}$ alkyl, C$_{1-4}$-haloalkyl, C$_{1-4}$ alkoxy, C$_{1-4}$ haloalkoxy, amino, C$_{1-4}$ alkylamino, C$_{1-4}$ dialkylamino, C(O)OH, C(O)C$_{1-4}$ alkyl, C(O)NH$_2$, C(O)NH(C$_{1-4}$ alkyl), or C(O)N(C$_{1-4}$ alkyl)$_2$;

R$^8$, R$^9$, and R$^{10}$, at each occurrence, are independently selected from H, C$_{1-6}$ alkyl, C$_{1-6}$ haloalkyl, heteroaryl-C$_{1-6}$-alkyl-, heterocycloalkyl-C$_{1-6}$-alkyl-, R$^{12}$R$^{13}$N—C$_{1-6}$-alkyl-, aryl, C$_{3-8}$ cycloalkyl, heteroaryl, and heterocycloalkyl, wherein the aryl, C$_{3-8}$ cycloalkyl, heteroaryl, and heterocycloalkyl, alone or as part of another moiety, are optionally substituted with 1, 2, or 3 substituents independently selected from halo, CN, OH, C$_{1-4}$ alkyl, C$_{1-4}$-haloalkyl, C$_{1-4}$ alkoxy, C$_{1-4}$ haloalkoxy, amino, C$_{1-4}$ alkylamino, C$_{1-4}$ dialkylamino, C(O)OH, C(O)C$_{1-7}$ alkyl, C(O)NH$_2$, C(O)NH(C$_{1-4}$ alkyl), or C(O)N(C$_{1-4}$ alkyl)$_2$;

R$^{11}$, at each occurrence, is independently selected from the group consisting of halo, C$_{1-4}$ alkyl, C$_{1-4}$ haloalkyl, amino-C$_{1-4}$-alkyl-, C$_{1-4}$ alkylamino-C$_{1-4}$ alkyl-, C$_{1-4}$ dialkylamino-C$_{1-4}$ alkyl-, hydroxy-C$_{1-4}$-alkyl-, C$_{1-4}$ alkyl-C$_{1-4}$ alkoxy, aryl, C$_{3-8}$ cycloalkyl, heteroaryl, heterocycloalkyl, aryl-(C$_{1-2}$ alkyl)-, C$_{3-8}$ cycloalkyl-(C$_{1-2}$ alkyl)-, heteroaryl-(C$_{1-2}$ alkyl)-, heterocycloalkyl-(C$_{1-2}$ alkyl)-, CN, NO$_2$, OR$^d$, SR$^d$, C(O)R$^d$, C(O)NR$^e$R$^f$, C(O)OR$^d$, OC(O)R$^d$, OC(O)NR$^e$R$^f$, NR$^e$R$^f$, NR$^e$C(O)R$^d$, S(O)R$^d$, S(O)NR$^e$R$^f$, S(O)$_2$R$^d$, NR$^e$S(O)$_2$R$^d$, and S(O)$_2$NR$^e$R$^f$, wherein the aryl, C$_{3-8}$ cycloalkyl, heteroaryl, and heterocycloalkyl, alone or as part of another moiety, are optionally substituted with one, two or three substituents independently selected from halo and C$_{1-4}$ alkyl;

R$^{12}$ and R$^{13}$, at each occurrence, are independently selected from the group consisting of H, C$_{1-6}$-alkyl, C$_{1-6}$ haloalkyl, aryl, C$_{3-8}$ cycloalkyl, heteroaryl, and heterocycloalkyl;

R$^{14}$ is selected from the group consisting of H, C$_{1-6}$ alkyl, C$_{1-6}$ haloalkyl, —C$_{1-6}$ alkyl-heterocycloalkyl, —C(O)OC$_{1-6}$ alkyl, —C(O)OC$_{1-6}$ haloalkyl, —C(O)NHC$_{1-6}$ alkyl, —C(O)NHC$_{1-6}$ haloalkyl;

R$^a$, at each occurrence, is independently selected from the group consisting of H, C$_{1-6}$ alkyl, C$_{1-6}$ haloalkyl, aryl, C$_{3-8}$ cycloalkyl, heteroaryl, and heterocycloalkyl;

R$^b$ and R$^c$, at each occurrence, are independently selected from the group consisting of H, C$_{1-6}$ alkyl, C$_{1-6}$ haloalkyl, aryl, C$_{3-8}$ cycloalkyl, heteroaryl, heterocycloalkyl;

R$^d$, at each occurrence, is independently selected from the group consisting of H, C$_{1-6}$ alkyl, C$_{1-6}$ haloalkyl, aryl, C$_{3-8}$ cycloalkyl, heteroaryl, and heterocycloalkyl;

R$^e$ and R$^f$, at each occurrence, are independently selected from the group consisting of H, C$_{1-6}$ alkyl, C$_{1-6}$ haloalkyl, aryl, C$_{3-8}$ cycloalkyl, heteroaryl, and heterocycloalkyl; and n is 0, 1, 2, or 3;

or a pharmaceutically acceptable salt or solvate thereof.

In one embodiment of formula (I), X$^2$ is N, X$^5$ is C, X$^1$, X$^3$, and X$^4$ are CH.

In one embodiment of formula (I), X$^1$ and X$^2$ are N, X$^5$ is C, and X$^3$ and X$^4$ are CR$^{14}$. In another embodiment of formula (I), X$^1$ and X$^2$ are N, X$^5$ is C, and X$^3$ and X$^4$ are CH.

In one embodiment of formula (I), X$^1$ and X$^3$ are N, X$^2$ and X$^5$ are C, and X$^4$ is CR$^{14}$. In another embodiment of formula (I), X$^1$ and X$^3$ are N, X$^2$ and X$^5$ are C, and X$^4$ is CH.

In one embodiment of formula (I), X$^1$, X$^2$, and X$^4$ are N, X$^5$ is C, and X$^3$ is CR$^{14}$. In another embodiment of formula (I), X$^1$, X$^2$, and X$^4$ are N, X$^5$ is C, and X$^3$ is CH.

In another embodiment of formula (I), X$^1$, X$^2$, X$^3$, and X$^4$ are N and X$^5$ is C.

In another embodiment of formula (I), X$^1$ and X$^5$ are N, X$^2$ is C, and X$^3$ and X$^4$ are CH.

In one embodiment of formula (I), Z is C$_{1-6}$ alkylene. In another embodiment, Z is —CH$_2$—, —CH$_2$CH$_2$—, —CH$_2$CH$_2$CH$_2$—, or —CH$_2$CH$_2$CH$_2$CH$_2$—. In another embodiment, Z is —CH(CH$_3$)—, —CH$_2$CH(CH$_3$)—, —CH(CH$_3$)CH$_2$—, —CH(CH$_3$)CH$_2$CH$_2$—, —CH$_2$CH(CH$_3$)CH$_2$—, —CH$_2$CH$_2$CH(CH$_3$)—, —C(CH$_3$)$_2$—, —CH$_2$C(CH)$_2$—, —C(CH$_3$)$_2$CH$_2$—, —CH$_2$CH$_2$C(CH$_3$)$_2$—, —CH$_2$C(CH$_3$)$_2$CH$_2$—, or —C(CH$_3$)$_2$CH$_2$CH$_2$—. In another embodiment, Z is —CH(CH$_2$CH$_3$)—, —CH$_2$CH(CH$_2$CH$_3$)—, —CH(CH$_2$CH$_3$)CH$_2$—, —CH(CH$_2$CH$_3$)CH$_2$CH$_2$—, —CH$_2$CH(CH$_2$CH$_3$)CH$_2$—, —CH$_2$CH$_2$CH(CH$_2$CH$_3$)—, —C(CH$_2$CH$_3$)$_2$—, —CH$_2$C(CH$_2$CH$_3$)$_2$—, —C(CH$_2$CH$_3$)$_2$CH$_2$—, —CH$_2$CH$_2$C(CH$_2$CH$_3$)$_2$—, —CH$_2$C(CH$_2$CH$_3$)$_2$CH$_2$—, or —C(CH$_2$CH$_3$)$_2$CH$_2$CH$_2$—. In yet another embodiment, Z is —CH$_2$—, —CH$_2$CH$_2$—, —CH(CH$_3$)—, or —C(CH$_3$)$_2$—.

In another embodiment of formula (I), Z is C$_{2-6}$ alkenylene. In yet another embodiment of formula (I), Z is —CH=CH—, —CH$_2$CH$_2$=CH—, —CH=CHCH$_2$—, —CH$_2$CH=CH—CH$_2$—, —CH=CH—CH$_2$CH$_2$—, or —CH$_2$CH$_2$—CH=CH—. In another embodiment of formula (I), Z is —CH(=CH$_2$)—, —CH$_2$CH(=CH$_2$)—, —CH(=CH$_2$)CH$_2$—, or —CH(CHCH$_3$)—. In yet another embodiment of formula (I), Z is —CH=CH— or —CH(=CH$_2$)—.

In one embodiment of formula (I), Z is a bond.

In one embodiment of formula (I), A is phenyl, naphthyl, indenyl or C$_{3-8}$ cycloalkyl. In yet another embodiment of formula (I), A is phenyl In another embodiment of formula (I), A is a 5-7 membered heterocycloalkyl or heterocycloalkenyl. In another embodiment of formula (I), A is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (I), A is dihydrofuranyl, dihydrothiophenyl, pyrrolinyl, imidazolinyl, pyrazolinyl, thiazolinyl, isothiazolinyl, dihydropyranyl, oxathiazinyl, oxadiazinyl, or oxazinyl.

In one embodiment of formula (I), A is a 5-7 membered heteroaryl. In another embodiment, A is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl.

A is optionally substituted with —$(R^1)_n$, wherein n is 0, 1, 2, or 3. In one embodiment, $R^1$ is selected from the group consisting of halo, CN, $NO_2$, $C_{1-6}$-alkyl, $C_{1-6}$-haloalkyl, aryl, $C_{3-8}$ cycloalkyl, heteroaryl, heterocycloalkyl, $OR^5$, $SR^5$, $C(O)R^5$, $C(O)NR^6R^7$, $C(O)OR^5$, $OC(O)R^5$, $OC(O)NR^6R^7$, $NR^6R^7$, $NR^6C(O)R^5$, $S(O)R^5$, $S(O)NR^6R^7$, $S(O)_2R^5$, $NR^6S(O)_2R^5$, and $S(O)_2NR^6R^7$; wherein the $C_{3-8}$ cycloalkyl, aryl, heteroaryl, and heterocycloalkyl, are optionally substituted with 1, 2, or 3 substituents independently selected from halo, $C_{1-4}$ alkyl, $C_{1-4}$ haloalkyl, CN, $NO_2$, $OR^a$, $SR^a$, $C(O)R^a$, $C(O)NR^bR^c$, $C(O)OR^a$, $OC(O)R^a$, $OC(O)NR^bR^c$, $NR^bR^c$, $NR^bC(O)R^a$, $S(O)R^a$, $S(O)NR^bR^c$, $S(O)_2R^a$, $NR^bS(O)_2R^a$, and $S(O)_2NR^bR^c$.

In another embodiment of formula (I), n is 0.

In another embodiment of formula (I), n is 1, 2, or 3, and $R^1$ is halo, $OR^5$, $C_{1-16}$ alkyl, $C_{1-6}$ haloalkyl, or CN, wherein $R^5$ is defined above. In another embodiment, n is 1 or 2, $R^1$ is $OR^5$, wherein $R^5$ is H or $C_{1-6}$ alkyl. In yet another embodiment of formula (I), n is 1, 2, or 3, and $R^1$ is halo.

In one embodiment of formula (I), n is 1 or 2, and $R^1$ is $C(O)NR^6R^7$, $C(O)OR^5$, $NR^6C(O)R^5$, $NR^6S(O)_2R^5$, or $S(O)_2NR^6R^7$, wherein $R^6$ and $R^7$ is defined above. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, or heterocycloalkyl moiety is optionally substituted with $C_{1-4}$ alkyl.

In one embodiment of formula (I), B is phenyl, pyridinyl, pyrimidinyl, pyrazinyl, pyridazinyl, or pyrazolinyl. In another embodiment of formula (I), B is phenyl.

In one embodiment of formula (I), B is

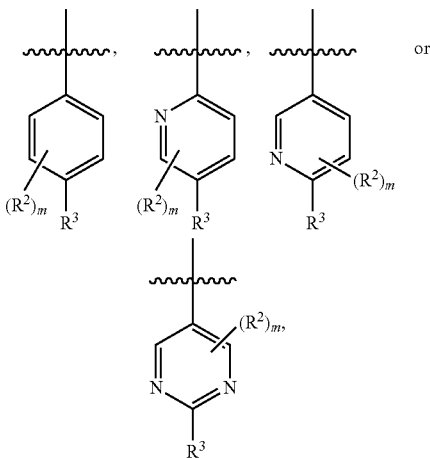

wherein $R^2$ and $R^3$ are defined above and m is 0, 1, or 2. In another embodiment of formula (I), m is 0. In yet another embodiment of formula (I), m is 1 and $R^2$ is selected from the group consisting of halo, $C_{1-4}$ alkyl, and $C_{1-4}$ alkoxy. In another embodiment of formula (I), $R^3$ is selected from the group consisting of aryl, $C_{3-8}$ cycloalkyl, heteroaryl, heterocycloalkyl, aryl-$C_{1-6}$ alkyl-, $C_{3-8}$ cycloalkyl-$C_{1-6}$-alkyl-, heteroaryl-$C_{1-6}$-alkyl-, and heterocycloalkyl-$C_{1-6}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In yet another embodiment of formula (I), $R^3$ is heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, $C(O)R^d$, and $S(O)_2R^d$ wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl, and wherein $R^d$ is defined above.

In one embodiment of formula (I), B is

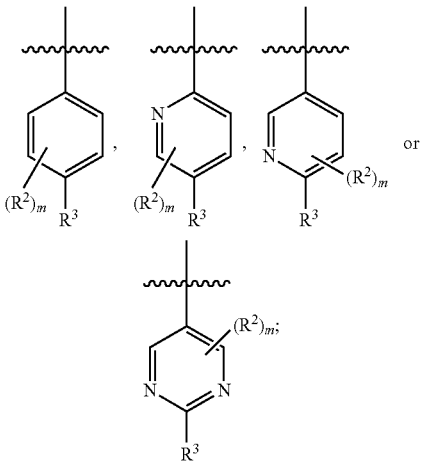

m is 0 or 1;
$R^2$ is halo, $C_{1-4}$ alkyl, or $C_{1-4}$ alkoxy;
$R^3$ is

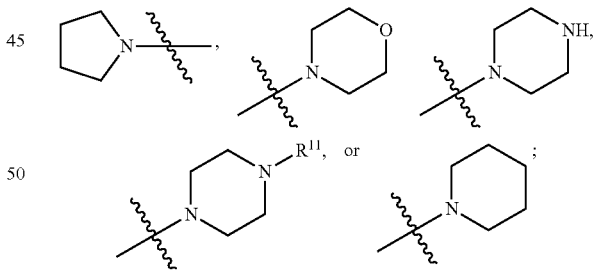

$R^{11}$ is $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, and hydroxy-$C_{1-4}$-alkyl-, $C_{1-4}$ alkyl-$C_{1-4}$ alkoxy, aryl, cycloalkyl, heteroaryl, heterocycloalkyl, aryl-($C_{1-2}$ alkyl)-, cycloalkyl-($C_{1-2}$ alkyl)-, heteroaryl-($C_{1-2}$ alkyl)-, or heterocycloalkyl-($C_{1-2}$ alkyl)-, wherein the aryl, cycloalkyl, heteroaryl, and heterocycloalkyl, alone or as part of another moiety, are optionally substituted with 1, 2, or 3 substituents independently selected from halo and $C_{1-4}$ alkyl.

In another embodiment, B is

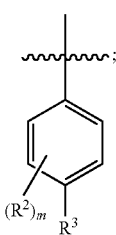

m is 0 or 1;
$R^2$ is halo, $C_{1-4}$ alkyl, or $C_{1-4}$ alkoxy;
$R^3$ is

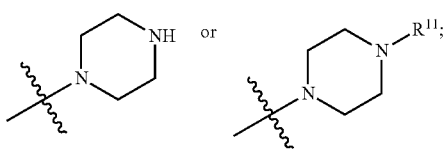

and $R^{11}$ is $C_{1-4}$ alkyl.

Embodiments of Formula (II)

In one embodiment, the present invention is directed, in part, to a class of compounds having a structure of Formula (II),

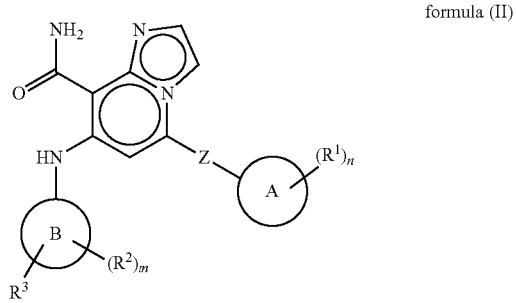

formula (II)

wherein A, B, Z, $R^1$, $R^2$, $R^3$, and n are as described in formula (I) and m is 0, 1, or 2.

In one embodiment of formula (II), the $C_{1-6}$ alkylene is —CH$_2$—, —CH$_2$CH$_2$—, —CH$_2$CH$_2$CH$_2$—, or —CH$_2$CH$_2$CH$_2$CH$_2$—. In another embodiment, the $C_{1-6}$ alkylene is —CH(CH$_3$)—, —CH$_2$CH(CH$_3$)—, —CH(CH$_3$)CH$_2$—, —CH(CH$_3$)CH$_2$CH$_2$—, —CH$_2$CH(CH$_3$)CH$_2$—, —CH$_2$CH$_2$CH(CH$_3$)—, —C(CH$_3$)$_2$—, —CH$_2$C(CH$_3$)$_2$—, —C(CH$_3$)$_2$CH$_2$—, —CH$_2$CH$_2$C(CH$_3$)$_2$—, —CH$_2$C(CH$_3$)$_2$CH$_2$—, or —C(CH$_3$)$_2$CH$_2$CH$_2$—. In another embodiment, the $C_{1-6}$ alkylene is CH(CH$_2$CH$_3$)—, —CH$_2$CH(CH$_2$CH$_3$)—, —CH(CH$_2$CH$_3$)CH$_2$—, —CH(CH$_2$CH$_3$)CH$_2$CH$_2$—, —CH$_2$CH(CH$_2$CH$_3$)CH$_2$—, —CH$_2$CH$_2$CH(CH$_2$CH$_3$)—, —C(CH$_2$CH$_3$)$_2$—, —CH$_2$C(CH$_2$CH$_3$)$_2$—, —C(CH$_2$CH$_3$)$_2$CH$_2$—, —CH$_2$CH$_2$C(CH$_2$CH$_3$)$_2$—, —CH$_2$C(CH$_2$CH$_3$)$_2$CH$_2$—, or —C(CH$_2$CH$_3$)$_2$CH$_2$CH$_2$—. In yet another embodiment, the $C_{1-6}$ alkylene is —CH$_2$—, —CH$_2$CH$_2$—, —CH(CH$_3$)—, or —C(CH$_3$)$_2$—.

In one embodiment of formula (II), A is phenyl, naphthyl, or $C_{3-8}$ cycloalkyl. In another embodiment of formula (II), A is phenyl.

In one embodiment of formula (II), n is 0. In another embodiment of formula (II), n is 1, 2, or 3, and $R^1$ is halo, $OR^5$, $C_{1-6}$ alkyl, $C_{1-6}$ haloalkyl, or CN, wherein $R^5$ is described in formula (II). In another embodiment, n is 1 or 2, $R^1$ is $OR^5$, wherein $R^5$ is H or $C_{1-6}$ alkyl. In yet another embodiment of formula (II), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (II), m is 0. In yet another embodiment of formula (II), m is 1 and $R^2$ is selected from the group consisting of halo, $C_{1-4}$ alkyl, and $C_{1-4}$ alkoxy. In another embodiment of formula (II), $R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, and heterocycloalkyl-$C_{1-6}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In yet another embodiment of formula (II), $R^3$ heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, $C(O)R^d$, and $S(O)_2R^d$ wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl, and wherein $R^d$ is described in formula (I).

In another embodiment of formula (II),
m is 0 or 1;
$R^2$ is halo, $C_{1-4}$ alkyl, or $C_{1-4}$ alkoxy;
$R^3$ is

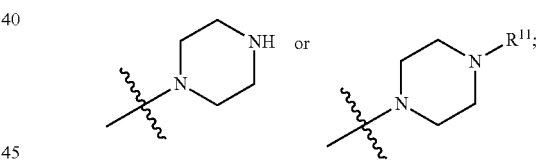

and $R^{11}$ is $C_{1-4}$ alkyl.

In one embodiment, the present invention is directed, in part, to a class of compounds having a structure of formula (IIa),

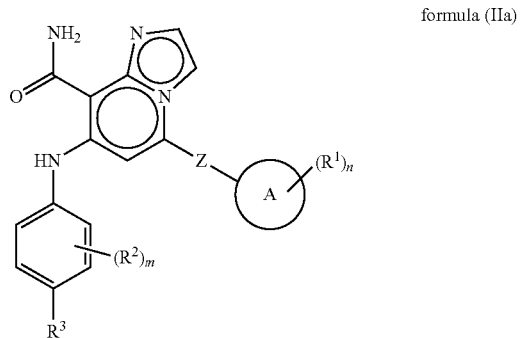

formula (IIa)

wherein A, $R^1$, $R^2$, $R^3$, m and n are as described in formula (II).

In one embodiment, the present invention is directed, in part, to a class of compounds having a structure of formula (IIb),

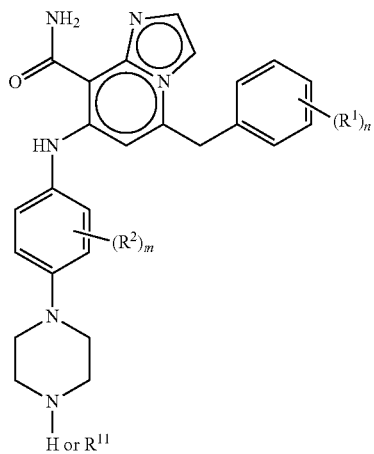

formula (IIb)

In one embodiment of formula (IIb), n is 0. In another embodiment of formula (IIb), n is 1, 2, or 3, and $R^1$ is halo, $OR^5$, $C_{1-6}$ alkyl, $C_{1-6}$ haloalkyl, or CN, wherein $R^5$ is described in formula (IIb). In another embodiment, n is 1 or 2, $R^1$ is $OR^5$, wherein $R^5$ is H or $C_{1-6}$ alkyl. In yet another embodiment of formula (IIb), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, or heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (IIb), m is 0. In yet another embodiment of formula (IIb), m is 1 and $R^2$ is selected from the group consisting of halo, $C_{1-4}$ alkyl, and $C_{1-4}$ alkoxy.

In one embodiment of formula (IIb), $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, $C_{3-8}$ cycloalkyl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, and heterocycloalkyl-($C_{1-2}$ alkyl)-, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl. In one embodiment of formula (IIb), $R^{11}$ is $C_{1-4}$ alkyl.

Embodiments of Formula (III)

In one embodiment, the present invention is directed, in part, to a class of compounds having a structure of Formula (III),

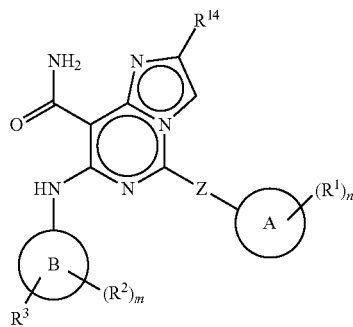

formula (III)

wherein A, B, Z, $R^1$, $R^2$, $R^3$, $R^{14}$, m, and n are as described in formula (I).

In one embodiment of formula (III), the $C_{1-6}$ alkylene is —$CH_2$—, —$CH_2CH_2$—, —$CH_2CH_2CH_2$—, or —$CH_2CH_2CH_2CH_2$—. In another embodiment, the $C_{1-6}$ alkylene is —$CH(CH_3)$—, —$CH_2CH(CH_3)$—, —$CH(CH_3)CH_2$—, —$CH(CH_3)CH_2CH_2$—, —$CH_2CH(CH_3)CH_2$—, —$CH_2CH_2CH(CH_3)$—, —$C(CH_3)_2$—, —$CH_2C(CH_3)_2$—, —$C(CH_3)_2CH_2$—, —$CH_2CH_2C(CH_3)_2$—, —$CH_2C(CH_3)_2CH_2$—, or —$C(CH_3)_2CH_2CH_2$—. In another embodiment, the $C_{1-6}$ alkylene is $CH(CH_2CH_3)$—, —$CH_2CH(CH_2CH_3)$—, —$CH(CH_2CH_3)CH_2$—, —$CH(CH_2CH_3)CH_2CH_2$—, —$CH_2CH(CH_2CH_3)CH_2$—, —$CH_2CH_2CH(CH_2CH_3)$—, —$C(CH_2CH_3)_2$—, —$CH_2C(CH_2CH_3)_2$—, —$C(CH_2CH_3)_2CH_2$—, —$CH_2CH_2C(CH_2CH_3)_2$—, —$CH_2C(CH_2CH_3)_2CH_2$—, or —$C(CH_2CH_3)_2CH_2CH_2$—. In yet another embodiment, the $C_{1-6}$ alkylene is —$CH_2$—, —$CH_2CH_2$—, —$CH(CH_3)$—, or —$C(CH_3)_2$—.

In one embodiment of formula (III), A is phenyl, naphthyl, or $C_{3-8}$ cycloalkyl. In another embodiment of formula (III), A is phenyl.

In one embodiment of formula (III), n is 0. In another embodiment of formula (III), n is 1, 2, or 3, and $R^1$ is halo, $OR^5$, $C_{1-6}$ alkyl, $C_{1-6}$ haloalkyl, or CN, wherein $R^5$ is described in formula (III). In another embodiment, n is 1 or 2, $R^1$ is $OR^5$, wherein $R^5$ is H or $C_{1-6}$ alkyl. In yet another embodiment of formula (III), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (III), m is 0. In yet another embodiment of formula (III), m is 1 and $R^2$ is selected from the group consisting of halo, $C_{1-4}$ alkyl, and $C_{1-4}$ alkoxy. In another embodiment of formula (III), $R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, and heterocycloalkyl-$C_{1-6}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In yet another embodiment of formula (III), $R^3$ heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, C(O)R$^d$, and S(O)$_2$R$^d$ wherein the aryl, C$_{3-8}$ cycloalkyl, heteroaryl, and heterocycloalkyl, alone or as part of another moiety, are optionally substituted with one, two or three substituents independently selected from halo and C$_{1-4}$ alkyl, and wherein R$^d$ is described in formula (I).

In another embodiment of formula (III),
m is 0 or 1;
R$^2$ is halo, C$_{1-4}$ alkyl, or C$_{1-4}$ alkoxy;
R$^3$ is

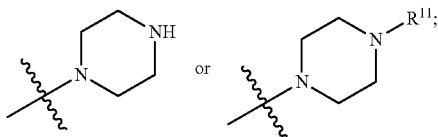

and R$^{11}$ is C$_{1-4}$ alkyl.

In one embodiment, the present invention is directed, in part, to a class of compounds having a structure of formula (IIIa),

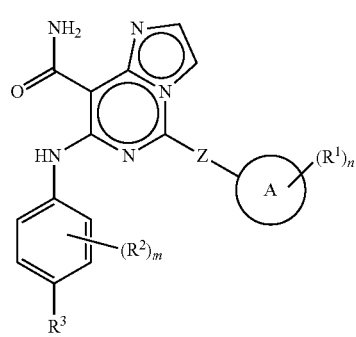

formula (IIIa)

wherein A, R$^1$, R$^2$, R$^3$, m and n are as described in formula (III).

In one embodiment, the present invention is directed, in part, to a class of compounds having a structure of formula (IIIb),

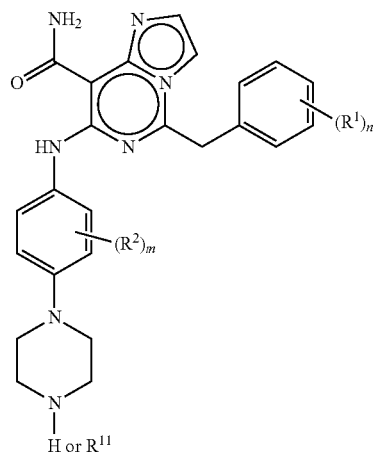

formula (IIIb)

In one embodiment of formula (IIIb), n is 0. In another embodiment of formula (IIIb), n is 1, 2, or 3, and R$^1$ is halo, OR$^5$, C$_{1-6}$ alkyl, C$_{1-6}$ haloalkyl, or CN, wherein R$^5$ is described in formula (IIIb). In another embodiment, n is 1 or 2, R$^1$ is OR$^5$, wherein R$^5$ is H or C$_{1-6}$ alkyl. In yet another embodiment of formula (IIIb), n is 1, 2, or 3, and R$^1$ is halo. In yet another embodiment, R$^1$ is NR$^6$S(O)$_2$R$^5$ or S(O)$_2$NR$^6$R$^7$, R$^6$ is hydrogen or C$_{1-6}$ alkyl, and R$^5$ and R$^7$ are independently C$_{1-6}$ alkyl, C$_{1-6}$ haloalkyl, aryl, C$_{3-8}$ cycloalkyl, heteroaryl, or heterocycloalkyl, wherein the aryl, C$_{3-8}$ cycloalkyl, heteroaryl, and heterocycloalkyl moiety is optionally substituted with C$_{1-4}$ alkyl.

In one embodiment of formula (IIIb), m is 0. In yet another embodiment of formula (IIIb), m is 1 and R$^2$ is selected from the group consisting of halo, C$_{1-4}$ alkyl, and C$_{1-4}$ alkoxy.

In one embodiment of formula (IIIb), R$^{11}$ is selected from the group consisting of C$_{1-4}$ alkyl, C$_{1-4}$ haloalkyl, amino-C$_{1-4}$-alkyl-, C$_{1-4}$ alkylamino-C$_{1-4}$ alkyl-, C$_{1-4}$ dialkylamino-C$_{1-4}$ alkyl-, hydroxy-C$_{1-4}$-alkyl-, C$_{1-4}$ alkyl-C$_{1-4}$ alkoxy, C$_{3-8}$ cycloalkyl, heterocycloalkyl, aryl-(C$_{1-2}$ alkyl)-, C$_{3-8}$ cycloalkyl-(C$_{1-2}$ alkyl)-, heteroaryl-(C$_{1-2}$ alkyl)-, and heterocycloalkyl-(C$_{1-2}$ alkyl)-, wherein the aryl, C$_{3-8}$ cycloalkyl, heteroaryl, and heterocycloalkyl, alone or as part of another moiety, are optionally substituted with one, two or three substituents independently selected from halo and C$_{1-4}$ alkyl. In one embodiment of formula (IIIb), R$^{11}$ is C$_{1-4}$ alkyl.

Embodiments of Formula (IV)

In one embodiment, the present invention is directed, in part, to a class of compounds having a structure of Formula (IV),

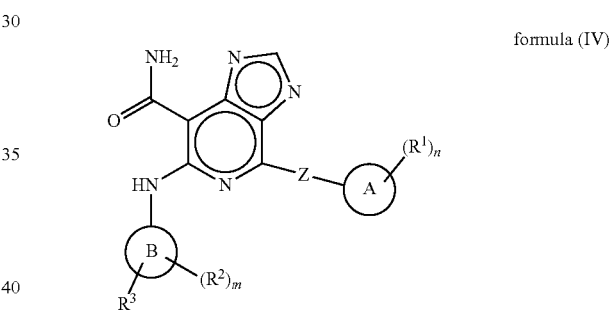

formula (IV)

wherein A, B, Z, R$^1$, R$^2$, R$^3$, and n are as described in formula (I) and m is 0, 1, or 2.

In one embodiment of formula (IV), the C$_{1-6}$ alkylene is —CH$_2$—, —CH$_2$CH$_2$—, —CH$_2$CH$_2$CH$_2$—, or —CH$_2$CH$_2$CH$_2$CH$_2$—. In another embodiment, the C$_{1-6}$ alkylene is —CH(CH$_3$)—, —CH$_2$CH(CH$_3$)—, —CH(CH$_3$)CH$_2$—, —CH(CH$_3$)CH$_2$CH$_2$—, —CH$_2$CH(CH$_3$)CH$_2$—, —CH$_2$CH$_2$CH(CH$_3$)—, —C(CH$_3$)$_2$—, —CH$_2$C(CH$_3$)$_2$—, —C(CH$_3$)$_2$CH$_2$—, —CH$_2$CH$_2$C(CH$_3$)$_2$—, —CH$_2$C(CH$_3$)$_2$CH$_2$—, or —C(CH$_3$)$_2$CH$_2$CH$_2$—. In another embodiment, the C$_{1-6}$ alkylene is CH(CH$_2$CH$_3$)—, —CH$_2$CH(CH$_2$CH$_3$)—, —CH(CH$_2$CH$_3$)CH$_2$—, —CH(CH$_2$CH$_3$)CH$_2$CH$_2$—, —CH$_2$CH(CH$_2$CH$_3$)CH$_2$—, —CH$_2$CH$_2$CH(CH$_2$CH$_3$)—, —C(CH$_2$CH$_3$)$_2$—, —CH$_2$C(CH$_2$CH$_3$)$_2$—, —C(CH$_2$CH$_3$)$_2$CH$_2$—, —CH$_2$CH$_2$C(CH$_2$CH$_3$)$_2$—, —CH$_2$C(CH$_2$CH$_3$)$_2$CH$_2$—, or —C(CH$_2$CH$_3$)$_2$CH$_2$CH$_2$—. In yet another embodiment, the C$_{1-6}$ alkylene is —CH$_2$—, —CH$_2$CH$_2$—, —CH(CH$_3$)—, or —C(CH$_3$)$_2$—.

In one embodiment of formula (IV), A is phenyl, naphthyl, or C$_{3-8}$ cycloalkyl. In another embodiment of formula (IV), A is phenyl.

In one embodiment of formula (IV), n is 0. In another embodiment of formula (IV), n is 1, 2, or 3, and R$^1$ is halo, OR$^5$, C$_{1-6}$ alkyl, C$_{1-6}$ haloalkyl, or CN, wherein R$^5$ is described in formula (IV). In another embodiment, n is 1 or 2, $R^1$ is $OR^5$, wherein $R^5$ is H or $C_{1-6}$ alkyl. In yet another embodiment of formula (IV), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-4}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (IV), m is 0. In yet another embodiment of formula (IV), m is 1 and $R^2$ is selected from the group consisting of halo, $C_{1-4}$ alkyl, and $C_{1-4}$ alkoxy. In another embodiment of formula (IV), $R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-4}$-alkyl-, heteroaryl-$C_{1-6}$-alkyl-, and heterocycloalkyl-$C_{1-6}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In yet another embodiment of formula (IV), $R^3$ heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, $C(O)R^d$, and $S(O)_2R^d$ wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl, and wherein $R^d$ is described in formula (I).

In another embodiment of formula (IV),
m is 0 or I;
$R^2$ is halo, $C_{1-4}$ alkyl, or $C_{1-4}$ alkoxy;
$R^3$ is

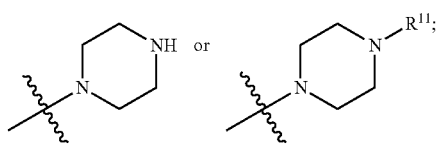

and $R^{11}$ is $C_{1-4}$ alkyl.

In one embodiment, the present invention is directed, in part, to a class of compounds having a structure of formula (IVa),

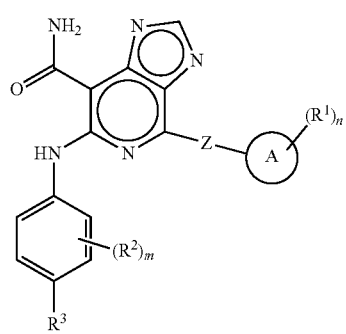

formula (IVa)

wherein A, $R^1$, $R^2$, $R^3$, m and n are as described in formula (IV).

In one embodiment, the present invention is directed, in part, to a class of compounds having a structure of formula (IVb),

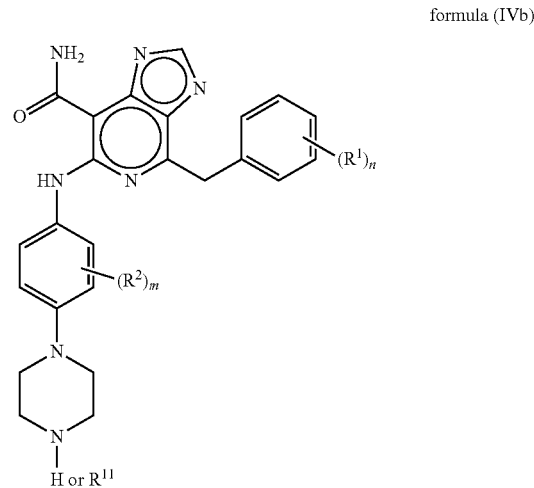

formula (IVb)

In one embodiment of formula (IVb), n is 0. In another embodiment of formula (IVb), n is 1, 2, or 3, and $R^1$ is halo, $OR^5$, $C_{1-6}$ alkyl, $C_{1-6}$ haloalkyl, or CN, wherein $R^5$ is described in formula (IVb). In another embodiment, n is 1 or 2, $R^1$ is $OR^5$, wherein $R^5$ is H or $C_{1-6}$ alkyl. In yet another embodiment of formula (IVb), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, or heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (IVb), m is 0. In yet another embodiment of formula (IVb), m is 1 and $R^2$ is selected from the group consisting of halo, $C_{1-4}$ alkyl, and $C_{1-4}$ alkoxy.

In one embodiment of formula (IVb), $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, $C_{3-8}$ cycloalkyl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, and heterocycloalkyl-($C_{1-2}$ alkyl)-, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl. In one embodiment of formula (IVb), $R^{11}$ is $C_{1-4}$ alkyl.

Embodiments of Formula (V)

In one embodiment, the present invention is directed, in part, to a class of compounds having a structure of Formula (V),

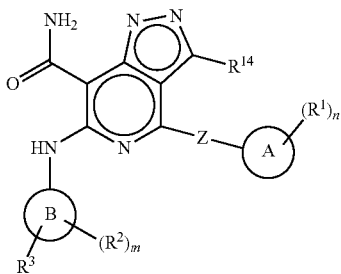

formula (V)

wherein A, B, Z, $R^1$, $R^2$, $R^3$, and n are as described in formula (I) and m is 0, 1, or 2.

In one embodiment of formula (V), the $C_{1-6}$ alkylene is —$CH_2$—, —$CH_2CH_2$—, —$CH_2CH_2CH_2$—, or —$CH_2CH_2CH_2CH_2$—. In another embodiment, the $C_{1-6}$ alkylene is —$CH(CH_3)$—, —$CH_2CH(CH_3)$—, —$CH(CH_3)CH_2$—, —$CH(CH_3)CH_2CH_2$—, —$CH_2CH(CH_3)CH_2$—, —$CH_2CH_2CH(CH_3)$—, —$C(CH_3)_2$—, —$CH_2C(CH_3)_2$—, —$C(CH_3)_2CH_2$—, —$CH_2CH_2C(CH_3)_2$—, —$CH_2C(CH_3)_2CH_2$—, or —$C(CH_3)_2CH_2CH_2$—. In another embodiment, the $C_{1-6}$ alkylene is $CH(CH_2CH_3)$—, —$CH_2CH(CH_2CH_3)$—, —$CH(CH_2CH_3)CH_2$—, —$CH(CH_2CH_3)CH_2CH_2$—, —$CH_2CH(CH_2CH_3)CH_2$—, —$CH_2CH_2CH(CH_2CH_3)$—, —$C(CH_2CH_3)_2$—, —$CH_2C(CH_2CH_3)_2$—, —$C(CH_2CH_3)_2CH_2$—, —$CH_2CH_2C(CH_2CH_3)_2$—, —$CH_2C(CH_2CH_3)_2CH_2$—, or —$C(CH_2CH_3)_2CH_2CH_2$—. In yet another embodiment, the $C_{1-6}$ alkylene is —$CH_2$—, —$CH_2CH_2$—, —$CH(CH_3)$—, or —$C(CH_3)_2$—.

In one embodiment of formula (V), A is phenyl, naphthyl, or $C_{3-8}$ cycloalkyl. In another embodiment of formula (V), A is phenyl.

In one embodiment of formula (V), n is 0. In another embodiment of formula (V), n is 1, 2, or 3, and $R^1$ is halo, $OR^5$, $C_{1-6}$ alkyl, $C_{1-6}$ haloalkyl, or CN, wherein $R^5$ is described in formula (V). In another embodiment, n is 1 or 2, $R^1$ is $OR^5$, wherein $R^5$ is H or $C_{1-6}$ alkyl. In yet another embodiment of formula (V), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (V), m is 0. In yet another embodiment of formula (V), m is 1 and $R^2$ is selected from the group consisting of halo, $C_{1-4}$ alkyl, and $C_{1-4}$ alkoxy. In another embodiment of formula (V), $R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, and heterocycloalkyl-$C_{1-4}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In yet another embodiment of formula (V), $R^3$ heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, $C(O)R^d$, and $S(O)_2R^d$ wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl, and wherein $R^d$ is described in formula (I).

In another embodiment of formula (V),
m is 0 or 1;
$R^2$ is halo, $C_{1-4}$ alkyl, or $C_{1-4}$ alkoxy;
$R^3$ is

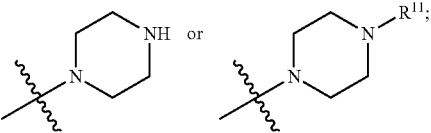

and $R^{11}$ is $C_{1-4}$ alkyl.

In one embodiment, the present invention is directed, in part, to a class of compounds having a structure of formula (Va),

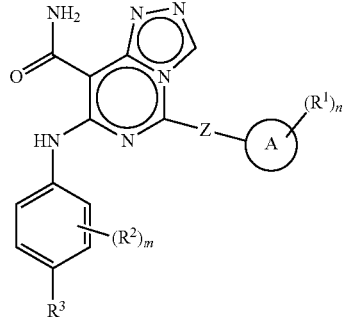

formula (Va)

wherein A, $R^1$, $R^2$, $R^3$, m and n are as described in formula (V).

In one embodiment, the present invention is directed, in part, to a class of compounds having a structure of formula (Vb),

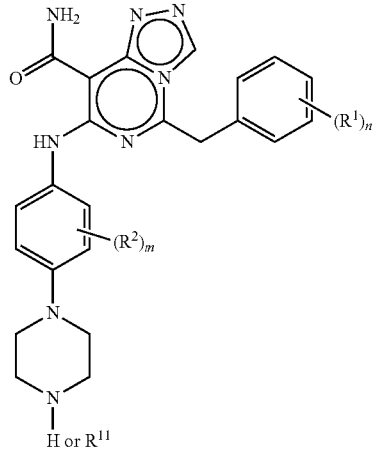

formula (Vb)

In one embodiment of formula (Vb), n is 0. In another embodiment of formula (Vb), n is 1, 2, or 3, and $R^1$ is halo, $OR^5$, $C_{1-4}$ alkyl, $C_{1-4}$ haloalkyl, or CN, wherein $R^5$ is described in formula (Vb). In another embodiment, n is 1 or 2, $R^1$ is $OR^5$, wherein $R^5$ is H or $C_{1-6}$ alkyl. In yet another embodiment of formula (Vb), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, or heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (Vb), m is 0. In yet another embodiment of formula (Vb), m is 1 and $R^2$ is selected from the group consisting of halo, $C_{1-4}$ alkyl, and $C_{1-4}$ alkoxy.

In one embodiment of formula (Vb), $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, $C_{3-8}$ cycloalkyl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, and heterocycloalkyl-($C_{1-2}$ alkyl)-, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl. In one embodiment of formula (Vb), $R^{11}$ is $C_{1-4}$ alkyl.

Embodiments of Formula (VI)

In one embodiment, the present invention is directed, in part, to a class of compounds having a structure of Formula (VI),

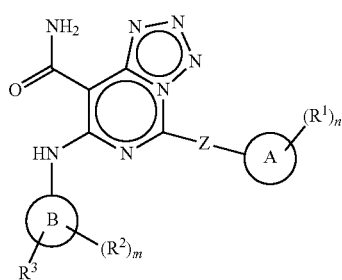

formula (VI)

wherein A, B, Z, $R^1$, $R^2$, $R^3$, and n are as described in formula (I) and m is 0, 1, or 2.

In one embodiment of formula (VI), the $C_{1-6}$ alkylene is —$CH_2$—, —$CH_2CH_2$—, —$CH_2CH_2CH_2$—, or —$CH_2CH_2CH_2CH_2$—. In another embodiment, the $C_{1-4}$ alkylene is —$CH(CH_3)$—, —$CH_2CH(CH_3)$—, —$CH(CH_3)CH_2$—, —$CH(CH_3)CH_2CH_2$—, —$CH_2CH(CH_3)CH_2$—, —$CH_2CH_2CH(CH_3)$—, —$C(CH_3)_2$—, —$CH_2C(CH_3)_2$—, —$C(CH_3)_2CH_2$—, —$CH_2CH_2C(CH_3)_2$—, —$CH_2C(CH_3)_2CH_2$—, or —$C(CH_3)_2CH_2CH_2$—. In another embodiment, the $C_{1-6}$ alkylene is $CH(CH_2CH_3)$—, —$CH_2CH(CH_2CH_3)$—, —$CH(CH_2CH_3)CH_2$—, —$CH(CH_2CH_3)CH_2CH_2$—, —$CH_2CH(CH_2CH_3)CH_2$—, —$CH_2CH_2CH(CH_2CH_3)$—, —$C(CH_2CH_3)_2$—, —$CH_2C(CH_2CH_3)_2$—, —$C(CH_2CH_3)_2CH_2$—, —$CH_2CH_2C(CH_2CH_3)_2$—, —$CH_2C(CH_2CH_3)_2CH_2$—, or —$C(CH_2CH_3)_2CH_2CH_2$—. In yet another embodiment, the $C_{1-6}$ alkylene is —$CH_2$—, —$CH_2CH_2$—, —$CH(CH_3)$—, or —$C(CH_3)_2$—.

In one embodiment of formula (VI), A is phenyl, naphthyl, or $C_{3-8}$ cycloalkyl. In another embodiment of formula (VI), A is phenyl.

In one embodiment of formula (VI), n is 0. In another embodiment of formula (VI), n is 1, 2, or 3, and $R^1$ is halo, $OR^5$, $C_{1-6}$ alkyl, $C_{1-6}$ haloalkyl, or CN, wherein $R^5$ is described in formula (VI). In another embodiment, n is 1 or 2, $R^1$ is $OR^5$, wherein $R^5$ is H or $C_{1-6}$ alkyl. In yet another embodiment of formula (VI), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (VI), m is 0. In yet another embodiment of formula (VI), m is 1 and $R^2$ is selected from the group consisting of halo, $C_{1-4}$ alkyl, and $C_{1-4}$ alkoxy. In another embodiment of formula (VI), $R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, and heterocycloalkyl-$C_{1-6}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In yet another embodiment of formula (VI), $R^3$ heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, $C(O)R^d$, and $S(O)_2R^d$ wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl, and wherein $R^d$ is described in formula (I).

In another embodiment of formula (VI),
m is 0 or 1;
$R^2$ is halo, $C_{1-4}$ alkyl, or $C_{1-4}$ alkoxy;
$R^3$ is

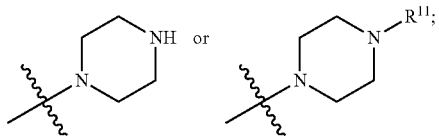

and $R^{11}$ is $C_{1-4}$ alkyl.

In one embodiment, the present invention is directed, in part, to a class of compounds having a structure of formula (VIa),

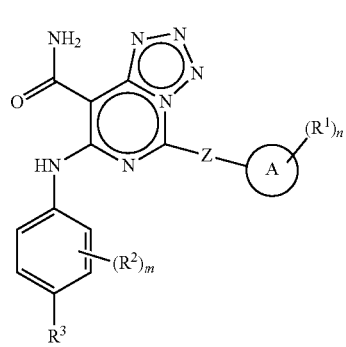

formula (VIa)

wherein A, $R^1$, $R^2$, $R^3$, m and n are as described in formula (VI).

In one embodiment, the present invention is directed, in part, to a class of compounds having a structure of formula (VIb),

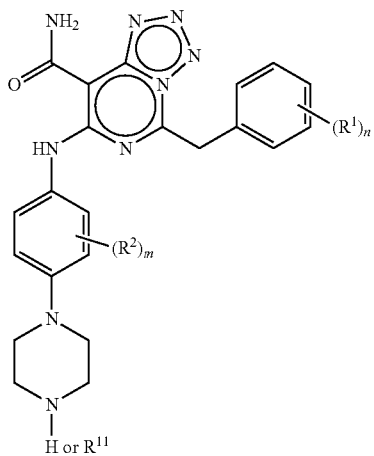

formula (VIb)

In one embodiment of formula (Vb), n is 0. In another embodiment of formula (VIb), n is 1, 2, or 3, and $R^1$ is halo, $OR^5$, $C_{1-6}$ alkyl, $C_{1-4}$ haloalkyl, or CN, wherein $R^5$ is described in formula (VIb). In another embodiment, n is 1 or 2, $R^1$ is $OR^5$, wherein $R^5$ is H or $C_{1-6}$ alkyl. In yet another embodiment of formula (VIb), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-4}$ alkyl, and $R^5$ and $R^7$ are independently $C_{1-6}$ alkyl, $C_{1-4}$ haloalkyl, aryl, $C_{3-8}$ cycloalkyl, heteroaryl, or heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (VIb), m is 0. In yet another embodiment of formula (VIb), m is 1 and $R^2$ is selected from the group consisting of halo, $C_{1-4}$ alkyl, and $C_{1-4}$ alkoxy.

In one embodiment of formula (VIb), $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, $C_{3-8}$ cycloalkyl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, and heterocycloalkyl-($C_{1-2}$ alkyl)-, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl. In one embodiment of formula (VIb), $R^{11}$ is $C_{1-4}$ alkyl.

Specific embodiments contemplated as part of the invention include, but are not limited to, compounds of formula (I), for example:

5-(2,6-dichlorobenzyl)-7-{[2-methoxy-4-(piperazin-1-yl)phenyl]amino}imidazo[1,2-c]pyrimidine-8-carboxamide;

5-(2,6-dichlorobenzyl)-7-{[2-methoxy-4-(piperazin-1-yl)phenyl]amino}[1,2,4]triazolo[4,3-c]pyrimidine-8-carboxamide;

5-(2,6-dichlorobenzyl)-7-{[2-methoxy-4-(piperazin-1-yl)phenyl]amino}[1,2,4]triazolo[4,3-c]pyrimidine-8-carboxamide;

5-(2,6-dichlorobenzyl)-7-{[4-(piperazin-1-yl)phenyl]amino}[1,2,4]triazolo[4,3-c]pyrimidine-8-carboxamide;

5-(2,6-dichlorobenzyl)-7-{[2-methoxy-4-(piperazin-1-yl)phenyl]amino}tetrazolo[1,5-c]pyrimidine-8-carboxamide;

5-(2,6-dichlorobenzyl)-7-{[4-(piperazin-1-yl)phenyl]amino}tetrazolo[1,5-c]pyrimidine-8-carboxamide;

5-(2,6-dichlorobenzyl)-7-{[2-methoxy-4-(piperazin-1-yl)phenyl]amino}imidazo[1,2-a]pyridine-8-carboxamide;

5-(2,6-dichlorobenzyl)-7-{[4-(piperazin-1-yl)phenyl]amino}imidazo[1,2-a]pyridine-8-carboxamide;

4-(2,6-dichlorobenzyl)-6-{[2-methoxy-4-(piperazin-1-yl)phenyl]amino}-1H-imidazo[4,5-c]pyridine-7-carboxamide;

5-(2,6-dichlorobenzyl)-7-{[4-(piperazin-1-yl)phenyl]amino}imidazo[1,2-c]pyrimidine-8-carboxamide;

5-(2,6-dichlorobenzyl)-7-{[2-methoxy-4-(morpholin-4-ylcarbonyl)phenyl]amino}imidazo[1,2-c]pyrimidine-8-carboxamide;

5-(2,6-dichlorobenzyl)-7-[(2-methoxy-4-{[2-(piperidin-1-yl)ethyl]carbamoyl}phenyl)amino][1,2,4]triazolo[4,3-c]pyrimidine-8-carboxamide;

5-(2,6-dichlorobenzyl)-7-[(4-{[2-(dimethylamino)ethyl]carbamoyl}-2-methoxyphenyl)amino]imidazo[1,2-c]pyrimidine-8-carboxamide;

7-{[2-methoxy-4-(piperazin-1-yl)phenyl]amino}-5-(pyrrolidin-1-yl)imidazo[1,2-c]pyrimidine-8-carboxamide;

5-(2,6-dichlorobenzyl)-7-{[2-(methylsulfinyl)-4-(piperazin-1-yl)phenyl]amino}imidazo[1,2-c]pyrimidine-8-carboxamide;

5-(2,6-dichlorobenzyl)-7-{[2,5-difluoro-4-(piperazin-1-yl)phenyl]amino}[1,2,4]triazolo[4,3-c]pyrimidine-8-carboxamide;

5-(2,6-dichlorobenzyl)-7-{[2,6-difluoro-4-(piperazin-1-yl)phenyl]amino}[1,2,4]triazolo[4,3-c]pyrimidine-8-carboxamide;

7-{[2-methoxy-4-(piperazin-1-yl)phenyl]amino}-5-{[(1S)-1-phenylethyl]amino}imidazo[1,2-c]pyrimidine-8-carboxamide;

5-(2,6-dichlorobenzyl)-7-{[3-methyl-4-(piperazin-1-yl)phenyl]amino}[1,2,4]triazolo[4,3-c]pyrimidine-8-carboxamide;

6-{[3-chloro-4-(piperazin-1-yl)phenyl]amino}-4-(2,6-dichlorobenzyl)-1H-imidazo[4,5-c]pyridine-7-carboxamide;

5-(2-chlorobenzyl)-7-{[2-methoxy-4-(piperazin-1-yl)phenyl]amino}imidazo[1,2-c]pyrimidine-8-carboxamide;

4-(2,6-dichlorobenzyl)-6-{[2,5-difluoro-4-(piperazin-1-yl)phenyl]amino}-1H-imidazo[4,5-c]pyridine-7-carboxamide;

7-{[2-methoxy-4-(piperazin-1-yl)phenyl]amino}-5-(piperazin-1-yl)imidazo[1,2-c]pyrimidine-8-carboxamide;

7-{[2-methoxy-4-(piperazin-1-yl)phenyl]amino}-5-(piperidin-4-ylamino)imidazo[1,2-c]pyrimidine-8-carboxamide;

4-(2,6-dichlorobenzyl)-6-{[4-(piperazin-1-yl)-2-(trifluoromethyl)phenyl]amino}-1H-imidazo[4,5-c]pyridine-7-carboxamide;

5-(2,6-dichlorobenzyl)-7-({2-methoxy-4-[(4-methylpiperazin-1-yl)carbonyl]phenyl}amino)imidazo[1,2-c]pyrimidine-8-carboxamide;

5-(2,6-dichlorobenzyl)-7-[(2-methoxy-4-{[2-(4-methylpiperazin-1-yl)ethyl]carbamoyl}phenyl)amino]imidazo[1,2-c]pyrimidine-8-carboxamide;

5-(2,6-dichlorobenzyl)-7-{[3,5-dichloro-4-(piperazin-1-yl)phenyl]amino}[1,2,4]triazolo[4,3-c]pyrimidine-8-carboxamide;

4-(2,6-dichlorobenzyl)-6-{[2-methyl-4-(piperazin-1-yl)phenyl]amino}-1H-imidazo[4,5-c]pyridine-7-carboxamide;

7-{[3-chloro-4-(piperazin-1-yl)phenyl]amino}-5-(2,6-dichlorobenzyl)[1,2,4]triazolo[4,3-c]pyrimidine-8-carboxamide;

5-(2,6-dichlorobenzyl)-7-{[2-fluoro-4-(piperazin-1-yl)phenyl]amino}[1,2,4]triazolo[4,3-c]pyrimidine-8-carboxamide;

4-(2,6-dichlorobenzyl)-6-{[3-methyl-4-(piperazin-1-yl)phenyl]amino}-1H-imidazo[4,5-c]pyridine-7-carboxamide;

4-(2,6-dichlorobenzyl)-6-({2-methoxy-4-[2-oxo-2-(pyrrolidin-1-yl)ethyl]phenyl}amino)-1H-imidazo[4,5-c]pyridine-7-carboxamide;

4-(2,6-dichlorobenzyl)-6-[(4-{[2-(dimethylamino)ethyl]carbamoyl}-2-methoxyphenyl)amino]-1H-imidazo[4,5-c]pyridine-7-carboxamide;

5-(2,6-dichlorobenzyl)-7-[(2-methoxy-4-{[2-(pyrrolidin-1-yl)ethyl]carbamoyl}phenyl)amino]imidazo[1,2-c]pyrimidine-8-carboxamide;

5-(2,6-dichlorobenzyl)-7-[(2-methoxy-4-{[2-(piperidin-1-yl)ethyl]carbamoyl}phenyl)amino]imidazo[1,2-c]pyrimidine-8-carboxamide;

5-(2,6-dichlorobenzyl)-7-[(2-methoxy-4-{[3-(morpholin-4-yl)propyl]carbamoyl}phenyl)amino]imidazo[1,2-c]pyrimidine-8-carboxamide;

5-(2,6-dichlorobenzyl)-7-{[2-methoxy-4-(piperazin-1-ylcarbonyl)phenyl]amino}imidazo[1,2-c]pyrimidine-8-carboxamide;

4-(2,6-dichlorobenzyl)-6-({2-methoxy-4-[(4-methylpiperazin-1-yl)carbonyl]phenyl}amino)-1H-imidazo[4,5-c]pyridine-7-carboxamide;

4-(2,6-dichlorobenzyl)-6-{[2-fluoro-4-(piperazin-1-yl)phenyl]amino}-1H-imidazo[4,5-c]pyridine-7-carboxamide;

5-[(2-chlorophenyl)amino]-7-{[2-methoxy-4-(piperazin-1-yl)phenyl]amino}imidazo[1,2-c]pyrimidine-8-carboxamide;

4-(2,6-dichlorobenzyl)-6-{[2-methoxy-4-(piperazin-1-ylcarbonyl)phenyl]amino}-1H-imidazo[4,5-c]pyridine-7-carboxamide;

5-[(2,3-difluorophenyl)amino]-7-{[2-methoxy-4-(piperazin-1-yl)phenyl]amino}imidazo[1,2-c]pyrimidine-8-carboxamide;

4-(2,6-dichlorobenzyl)-6-{[3,5-dichloro-4-(piperazin-1-yl)phenyl]amino}-1H-imidazo[4,5-c]pyridine-7-carboxamide;

4-(2,6-dichlorobenzyl)-6-{[3,5-difluoro-4-(piperazin-1-yl)phenyl]amino}-1H-imidazo[4,5-c]pyridine-7-carboxamide;

6-{[2-chloro-4-(piperazin-1-yl)phenyl]amino}-4-(2,6-dichlorobenzyl)-1H-imidazo[4,5-c]pyridine-7-carboxamide;

4-(2,6-dichlorobenzyl)-6-{[3-fluoro-2-methoxy-4-(piperazin-1-yl)phenyl]amino}-1H-imidazo[4,5-c]pyridine-7-carboxamide;

4-(2,6-dichlorobenzyl)-6-{[4-(piperazin-1-yl)-3-(trifluoromethyl)phenyl]amino}-1H-imidazo[4,5-c]pyridine-7-carboxamide;

4-(2,6-dichlorobenzyl)-6-{[4-(piperazin-1-yl)-2-(trifluoromethoxy)phenyl]amino}-1H-imidazo[4,5-c]pyridine-7-carboxamide;

4-(2,6-dichlorobenzyl)-6-{[2-methoxy-5-(piperazin-1-yl)phenyl]amino}-1H-imidazo[4,5-c]pyridine-7-carboxamide;

4-(2,6-dichlorobenzyl)-6-{[4-(hexahydropyrrolo[1,2-a]pyrazin-2(1H)-yl)-2-methoxyphenyl]amino}-1H-imidazo[4,5-c]pyridine-7-carboxamide;

4-[(2-chlorophenyl)amino]-6-{[2-methoxy-4-(piperazin-1-yl)phenyl]amino}pyrazolo[1,5-a]pyrazine-7-carboxamide;

4-(2,6-dichlorobenzyl)-6-{[2,3-dimethyl-4-(piperazin-1-yl)phenyl]amino}-1H-imidazo[4,5-c]pyridine-7-carboxamide;

4-(2,6-dichlorobenzyl)-6-{[2-methoxy-4-(pyrrolidin-1-ylmethyl)phenyl]amino}-1H-imidazo[4,5-c]pyridine-7-carboxamide;

7-{[2-bromo-4-(piperazin-1-yl)phenyl]amino}-5-(2,6-dichlorobenzyl)[1,2,4]triazolo[4,3-c]pyrimidine-8-carboxamide;

4-(2,6-dichlorobenzyl)-6-{[2-fluoro-5-methyl-4-(piperazin-1-yl)phenyl]amino}-1H-imidazo[4,5-c]pyridine-7-carboxamide;

4-(2,6-dichlorobenzyl)-6-{[3,5-difluoro-2-methoxy-4-(piperazin-1-yl)phenyl]amino}-1H-imidazo[4,5-c]pyridine-7-carboxamide;

4-(2,6-dichlorobenzyl)-6-[(6-methoxy-1,2,3,4-tetrahydroisoquinolin-7-yl)amino]-1H-imidazo[4,5-c]pyridine-7-carboxamide;

6-{[2-chloro-4-(piperidin-4-yl)phenyl]amino}-4-(2,6-dichlorobenzyl)-1H-imidazo[4,5-c]pyridine-7-carboxamide;

7-(2-chloro-4-(piperidin-4-yl)phenylamino)-5-(2-chlorobenzyl)-3-ethyl-[1,2,4]triazolo[4,3-c]pyrimidine-8-carboxamide;

5-(2,6-dichlorobenzyl)-7-{[2-methoxy-4-(piperazin-1-yl)phenyl]amino}-3-methyl[1,2,4]triazolo[4,3-c]pyrimidine-8-carboxamide;

5-(2,6-dichlorobenzyl)-3-ethyl-7-{[2-methoxy-4-(piperazin-1-yl)phenyl]amino}[1,2,4]triazolo[4,3-c]pyrimidine-8-carboxamide;

5-(2-chlorobenzyl)-2-ethyl-7-{[2-methoxy-4-(piperazin-1-yl)phenyl]amino}imidazo[1,2-c]pyrimidine-8-carboxamide;

5-(2-chlorobenzyl)-7-{[2-chloro-4-(piperidin-4-yl)phenyl]amino}-2-ethylimidazo[1,2-c]pyrimidine-8-carboxamide;

5-(2-chlorobenzyl)-7-{[2-chloro-4-(piperidin-4-yl)phenyl]amino}[1,2,4]triazolo[4,3-c]pyrimidine-8-carboxamide;

5-(2-chlorobenzyl)-3-ethyl-7-{[2-methoxy-4-(piperazin-1-yl)phenyl]amino}[1,2,4]triazolo[4,3-c]pyrimidine-8-carboxamide;

5-(2,3-dichlorobenzyl)-7-{[2-methoxy-4-(piperidin-4-yl)phenyl]amino}[1,2,4]triazolo[4,3-c]pyrimidine-8-carboxamide;

5-(2-fluorobenzyl)-7-{[2-methoxy-4-(piperidin-4-yl)phenyl]amino}[1,2,4]triazolo[4,3-c]pyrimidine-8-carboxamide;

5-(2,3-difluorobenzyl)-7-{[2-methoxy-4-(piperidin-4-yl)phenyl]amino}[1,2,4]triazolo[4,3-c]pyrimidine-8-carboxamide;

5-(2,6-dichlorobenzyl)-7-{[2-methoxy-4-(piperazin-1-yl)phenyl]amino}-2-(morpholin-4-ylmethyl)imidazo[1,2-c]pyrimidine-8-carboxamide;

ethyl 8-carbamoyl-5-(2,6-dichlorobenzyl)-7-{[2-methoxy-4-(piperazin-1-yl)phenyl]amino}imidazo[1,2-c]pyrimidine-2-carboxylate;

5-(2,6-dichlorobenzyl)-N~2~-ethyl-7-{[2-methoxy-4-(piperazin-1-yl)phenyl]amino}imidazo[1,2-c]pyrimidine-2,8-dicarboxamide; and 5-(2,6-dichlorobenzyl)-7-{[2-methoxy-4-(piperazin-1-yl)phenyl]amino}-N~2~-(2,2,2-trifluoroethyl)imidazo[1,2-c]pyrimidine-2,8-dicarboxamide.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. Tautomeric forms are intended to be encompassed by the scope of this invention, even though only one tautomeric form may be depicted.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

Schemes

Scheme 1

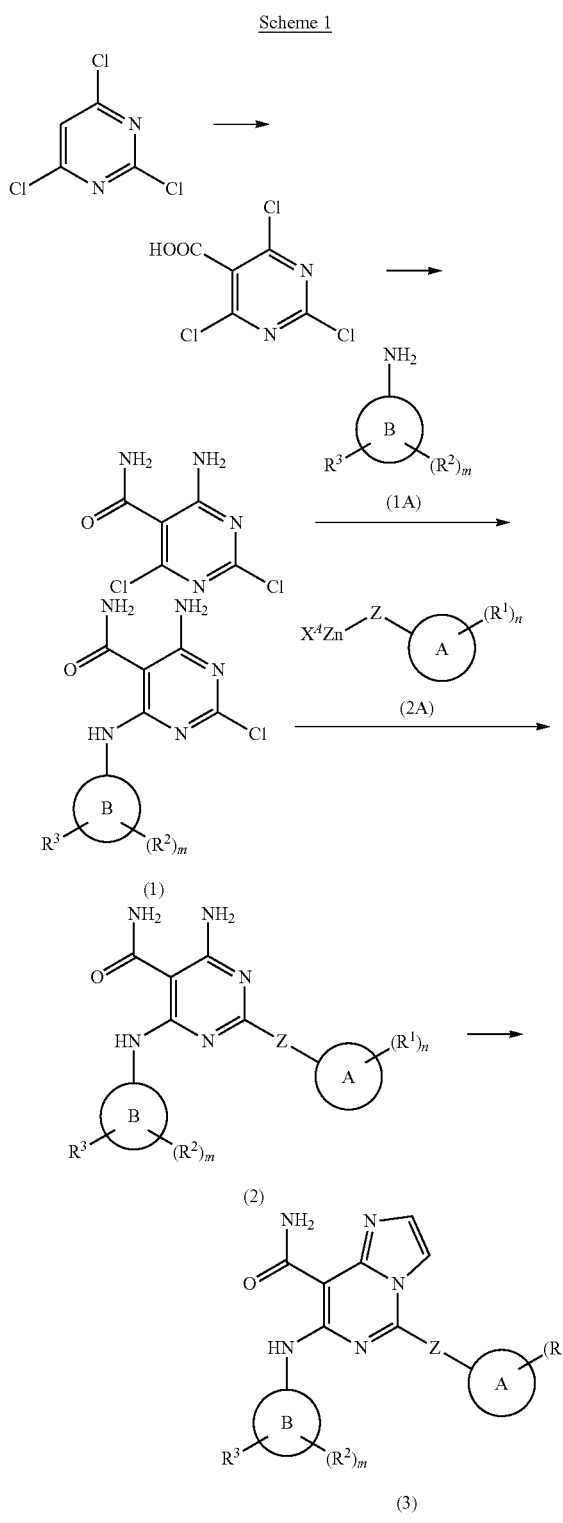

As shown in Scheme 1, 2,4,6-trichloropyrimidine can be added to a mixture of n-butyl lithium and diisopropylamine, followed by the addition of solid carbon dioxide (dry ice) and then an aqueous acid such as but not limited to aqueous hydrochloric acid to provide 2,4,6-trichloropyrimidine-5-carboxylic acid. The reaction is typically performed at reduced temperature in a solvent such as but not limited to tetrahydrofuran. 4-Amino-2,6-dichloropyrimidine-5-carboxamide can be prepared by first reacting 2,4,6-trichloropyrimidine-5-carboxylic acid with oxalyl chloride at ambient temperature, followed by reacting the resulting acid chloride at reduced temperature with ammonium hydroxide. The reaction is typically performed in a solvent such as but not limited to tetrahydrofuran, N,N-dimethylformamide, and the like, or mixtures thereof. 4-Amino-2,6-dichloropyrimidine-5-carboxamide can be reacted with compounds of formula (1A), wherein B, $R^2$, $R^3$, and m are as described herein, to provide compounds of formula (1). The reaction typically requires elevated temperatures and the use of a base such as but not limited to diisopropylethylamine in a solvent such as but not limited to 4-dioxane. Compounds of formula (2), can be prepared by reacting compounds of formula (1) with an organozinc compound of formula (2A), wherein Z, A, $R^1$, and n are as described herein and $X^A$ is a halide. The reaction typically involves the use of heat and a nickel or palladium catalyst such as but not limited to bis(triphenylphosphine)palladium(II) dichloride or tetrakis(triphenylphosphine)palladium(0) in a solvent such as but not limited to N-methylpyrrolidone, tetrahydrofuran, or mixtures thereof. A solution of 2-chloro-1,1-diethoxyethane can be reacted with acetic acid at elevated temperature and then added to a solution of a compound of formula (2) to provide a compound of formula (3), which is representative of compounds of Formula (I). The reaction is typically performed at elevated temperature in a solvent such as but not limited to N,N-dimethylformamide.

Scheme 2

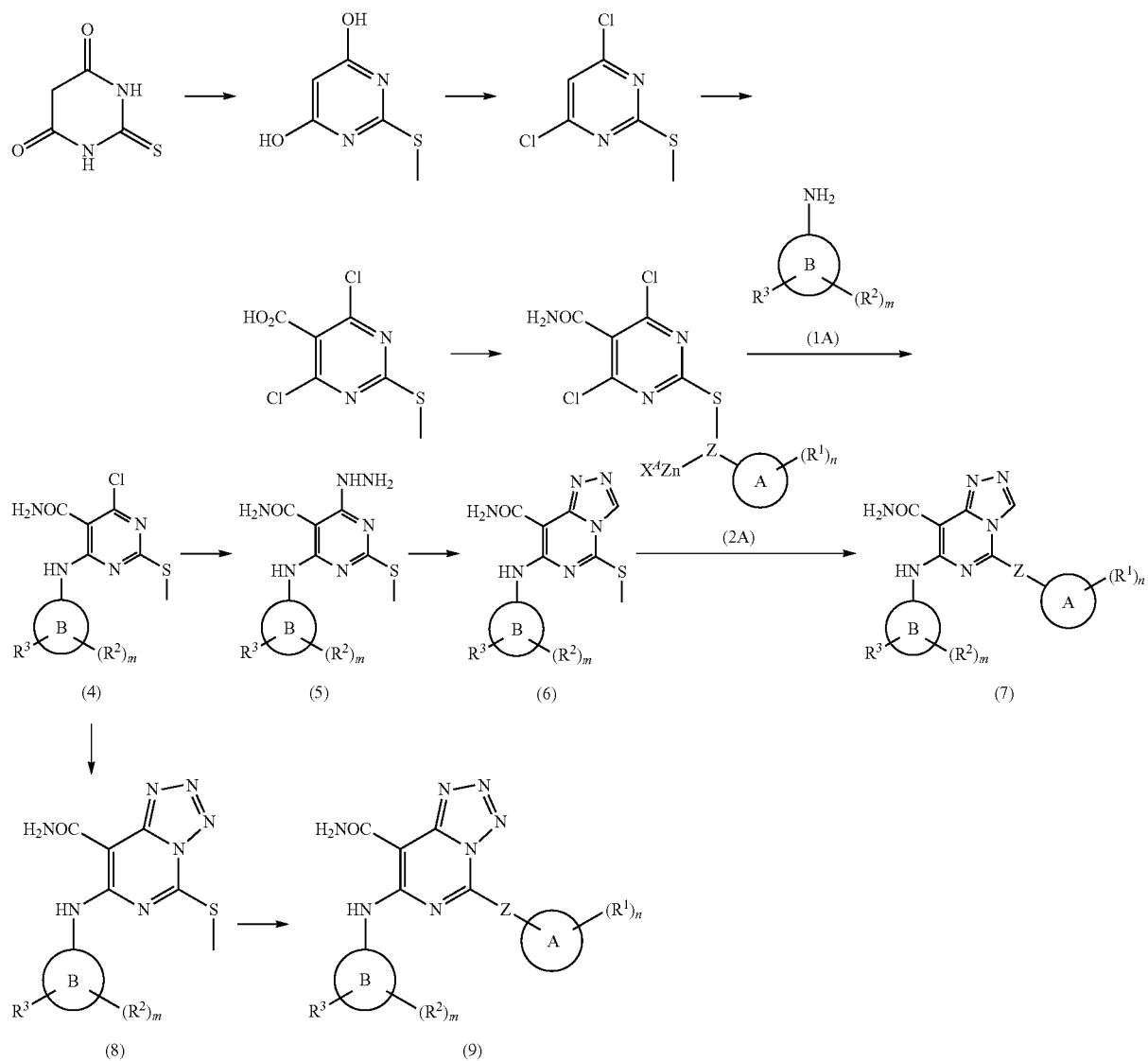

Methyl iodide can be added to a solution of 2-thioxodihydropyrimidine-4,6(1H,5H)-dione and aqueous sodium hydroxide to provide 2-(methylthio)pyrimidine-4,6-diol. The reaction is typically performed in a solvent such as but not limited to ethanol, and may require the use of heat. Addition of phosphorus oxychloride to 2-(methylthio)pyrimidine-4,6-diol will provide 4,6-dichloro-2-(methylthio)pyrimidine. The reaction is typically done at elevated temperature without an additional solvent. 4,6-Dichloro-2-(methylthio)pyrimidine can be added to a mixture of diisopropylamine and n-butyl lithium, followed by the addition of dry carbon dioxide gas to provide 4,6-dichloro-2-(methylthio)pyrimidine-5-carboxylic acid. The reaction is typically performed at reduced temperature in a solvent such as but not limited to tetrahydrofuran. A mixture of 4,6-dichloro-2-(methylthio)pyrimidine-5-carboxylic acid and thionyl chloride can be refluxed together and concentrated, followed by the addition of aqueous ammonia at reduced temperature in a solvent such as but not limited to tetrahydrofuran to provide 4,6-dichloro-2-(methylthio)pyrimidine-5-carboxamide. A compound of formula (1A) wherein B, $R^2$, $R^3$, and m are as described herein, can be reacted with 4,6-dichloro-2-(methylthio)pyrimidine-5-carboxamide in the presence of a base such as but not limited to N,N-diisopropylethylamine to provide compounds of formula (4). The reaction typically requires the use of heat and a solvent such as but not limited to 1,4-dioxane. Compounds of formula (5) can be prepared by reacting compounds of formula (4) with hydrazine hydrate. The reaction is typically performed at ambient temperature in a solvent such as but not limited to 1,4-dioxane. Methyl orthoformate can be reacted with compounds of formula (5) to provide compounds of formula (6). The reaction may require the use of heat. Compounds of formula (7), which are representative of the compounds of Formula (I), can be prepared by reacting compounds of formula (6) with an organozinc compound of formula (2A), wherein Z, A, $R^1$, and n are as described herein and $X^4$ is a halide. The reaction typically involves the use of heat and a nickel or palladium catalyst such as but not limited to bis(triphenylphosphine)palladium(II) dichloride or tetrakis(triphenylphosphine)palladium(0) in a solvent such as but not limited to N-methylpyrrolidone, tetrahydrofuran, or mixtures thereof.

Alternatively, compounds of formula (8) can be prepared by reacting compounds of formula (4) with sodium azide. The reaction is typically performed at ambient temperature in a solvent such as but not limited to N,N-dimethylformamide. Compounds of formula (9), which are representative of the compounds of Formula (I), can be prepared by reacting compounds of formula (8) with an organozinc compound of formula (2A), wherein Z, A, $R^1$, and n are as described herein and $X^A$ is a halide. The reaction typically involves the use of heat and a nickel or palladium catalyst such as but not limited to bis(triphenylphosphine)palladium(II) dichloride or tetrakis(triphenylphosphine)palladium(0) in a solvent such as but not limited to N-methylpyrrolidone, tetrahydrofuran, or mixtures thereof.

mide to provide compounds of formula (10). The reaction typically requires the use of heat and a solvent such as but not limited to 1,4-dioxane. Compounds of formula (11), which are representative of the compounds of Formula (I), can be prepared by reacting compounds of formula (10) with an organozinc compound of formula (2A), wherein Z, A, $R^1$, and n are as described herein and $X^A$ is a halide. The reaction typically involves the use of heat and a nickel or palladium catalyst such as but not limited to bis(triphenylphosphine)palladium(II) dichloride or tetrakis(triphenylphosphine)palladium(0) in a solvent such as but not limited to N-methylpyrrolidone, tetrahydrofuran, or mixtures thereof.

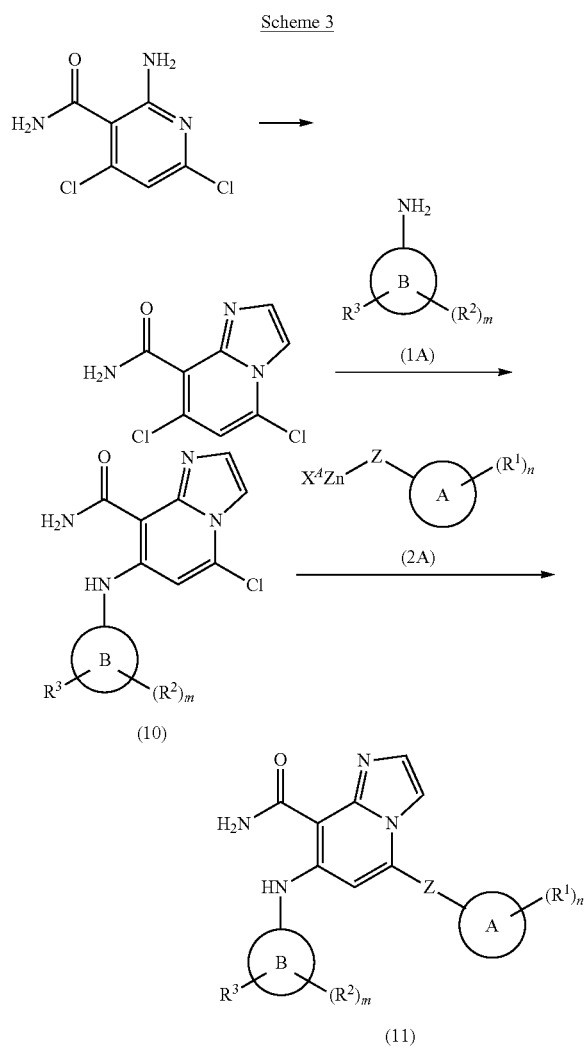

Scheme 3

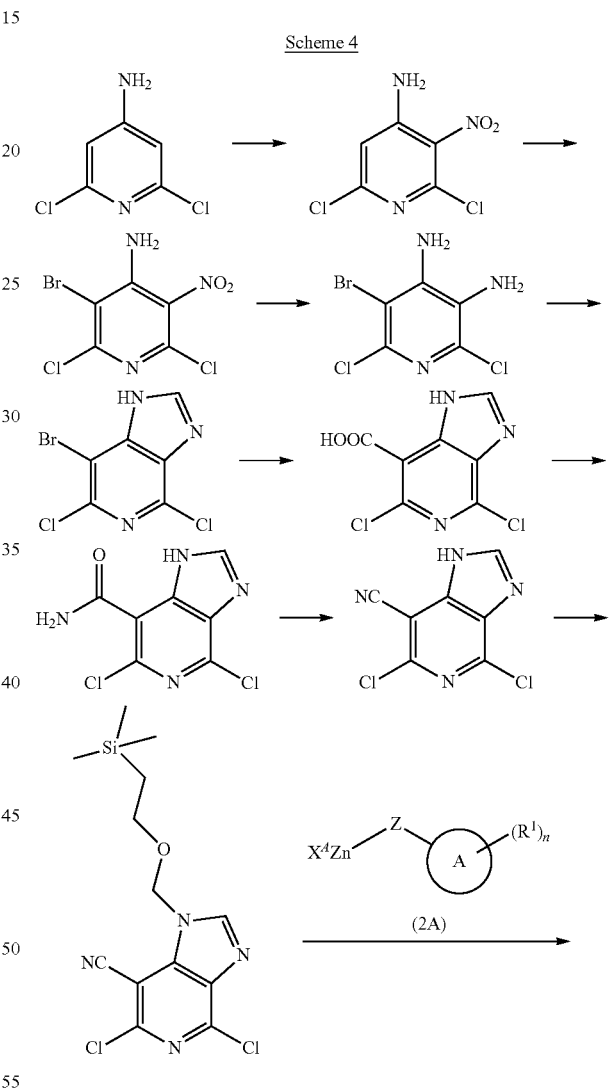

Scheme 4

2-Amino-4,6-dichloronicotinamide can be reacted with 2-chloroacetaldehyde to provide 5,7-dichloroimidazo[1,2-a]pyridine-8-carboxamide. The reaction is typically performed at elevated temperature in a solvent such as but not limited to N,N-dimethylformamide. Compounds of formula (IA) wherein B, $R^2$, $R^3$, and m are as described herein, can be reacted with 5,7-dichloroimidazo[1,2-a]pyridine-8-carboxa-

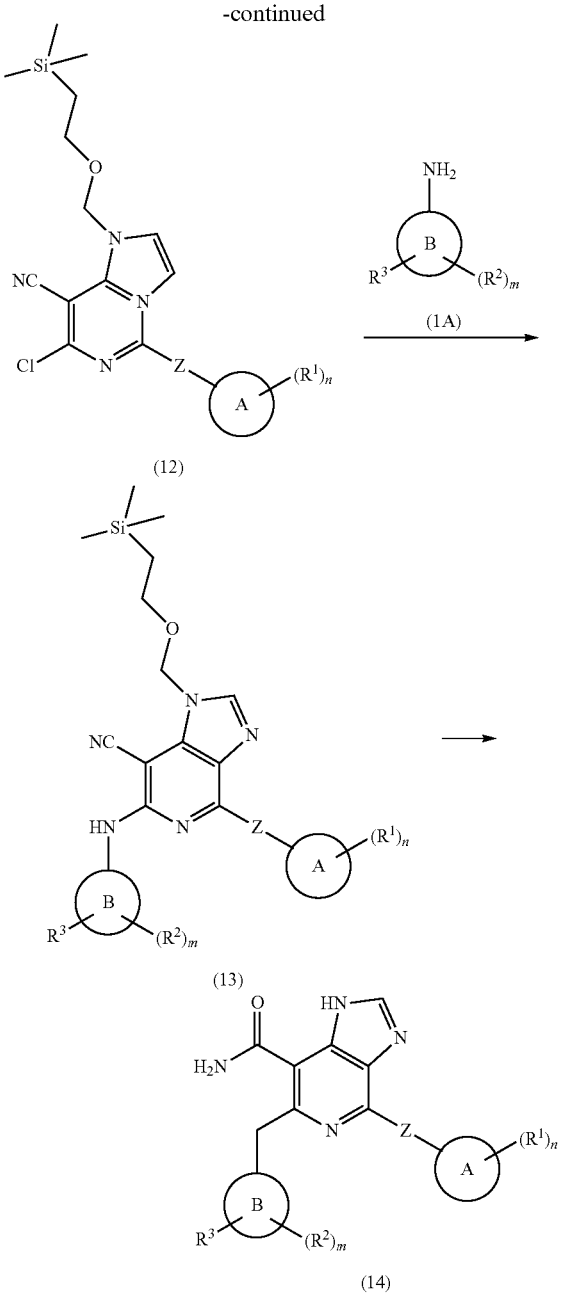

reaction is typically performed at elevated temperature. N,N,N',N'-Tetramethylethylenediamine can be added to 7-bromo-4,6-dichloro-1H-imidazo[4,5-c]pyridine followed by the addition of n-butyllithium and then dry carbon dioxide gas to provide 4,6-dichloro-1H-imidazo[4,5-c]pyridine-7-carboxylic acid. The reaction is typically performed at reduced temperature in a solvent such as but not limited to tetrahydrofuran, hexane, and the like, or mixtures thereof. A mixture of 4,6-dichloro-1H-imidazo[4,5-c]pyridine-7-carboxylic acid and thionyl chloride can be refluxed together and concentrated, followed by the addition of aqueous ammonia at reduced temperature in a solvent such as but not limited to tetrahydrofuran to provide 4,6-dichloro-1H-imidazo[4,5-c]pyridine-7-carboxamide. Phosphorus oxychloride can be reacted with 4,6-dichloro-1H-imidazo[4,5-c]pyridine-7-carboxamide at elevated temperature to provide 4,6-dichloro-1H-imidazol-[4,5-c]pyridine-7-carbonitrile. A base such as but not limited to triethylamine can be reacted with 4,6-dichloro-1H-imidazo[4,5-c]pyridine-7-carbonitrile, followed by the addition of 2-(trimethylsilyl)ethoxymethyl chloride to provide 4,6-dichloro-1-((2-(trimethylsilyl)ethoxy)methyl)-1H-imidazo[4,5-c]pyridine-7-carbonitrile. The reaction is typically performed at low temperature followed by warming to ambient temperature, in a solvent such as but not limited to tetrahydrofuran. Compounds of formula (12), can be prepared by reacting 4,6-dichloro-1-((2-(trimethylsilyl)ethoxy)methyl)-1H-imidazo[4,5-c]pyridine-7-carbonitrile with an organozinc compound of formula (2A), wherein Z, A, $R^1$, and n are as described herein and $X^A$ is a halide. The reaction typically involves the use of heat and a nickel or palladium catalyst such as but not limited to bis(triphenylphosphine)palladium(II) dichloride or tetrakis(triphenylphosphine)palladium(0) in a solvent such as but not limited to N-methylpyrrolidone, tetrahydrofuran, or mixtures thereof. A compound of formula (IA) wherein B, $R^2$, $R^3$, and m are as described herein, can be reacted with compounds of formula (12) in the presence of a base such as but not limited to N,N-diisopropylethylamine or cesium carbonate to provide compounds of formula (13). The reaction typically requires the use of heat and a solvent such as but not limited to 1,4-dioxane or toluene. Compounds of formula (13) can be heated in a mixture of concentrated sulfuric acid and water to provide compounds of formula (14), which are representative of the compounds of Formula (I).

2,6-Dichloropyridin-4-amine can be added in portions to concentrated sulfuric acid, followed by the addition of fuming nitric acid to provide 2,6-dichloro-3-nitropyridin-4-amine. The reaction is typically performed at reduced temperature before warming to ambient temperature. 2,6-Dichloro-3-nitropyridin-4-amine can be reacted with N-bromosuccinimide in acetic acid to provide 3-bromo-2,6-dichloro-5-nitropyridin-4-amine. The reaction is typically performed at elevated temperature. Reduction of -bromo-2,6-dichloro-5-nitropyridin-4-amine with Raney nickel and hydrogen gas can provide 5-bromo-2,6-dichloropyridine-3,4-diamine. The reaction may be performed at ambient temperature in a solvent such as but not limited to ethanol. 7-Bromo-4,6-dichloro-1H-imidazo[4,5-c]pyridine can be prepared by reacting 5-bromo-2,6-dichloropyridine-3,4-diamine with triethyl orthoformate and acetic anhydride. The Scheme 5

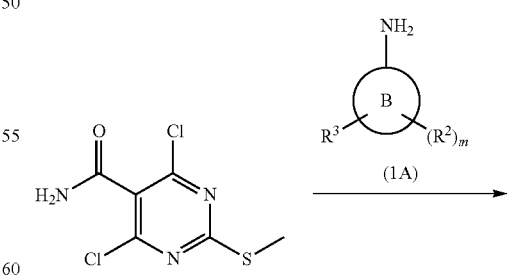

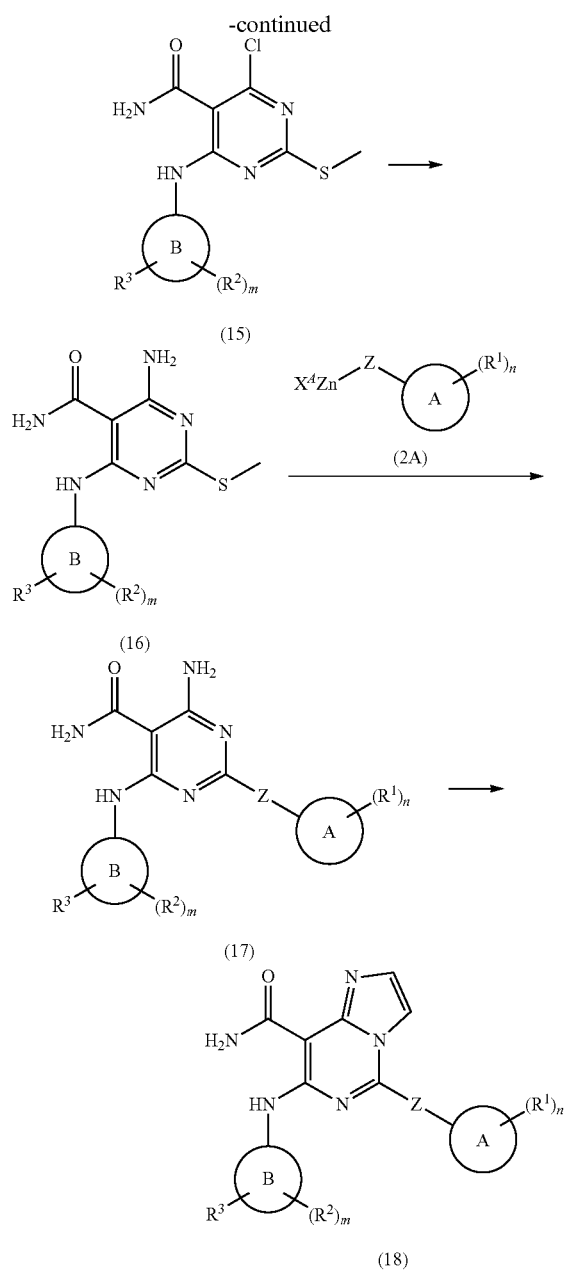

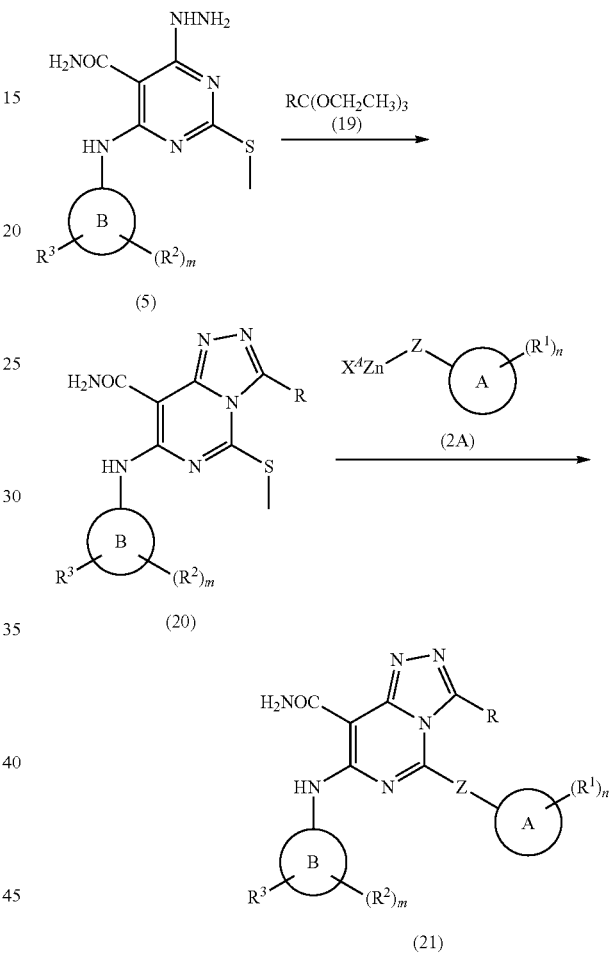

in a solvent such as but not limited to N-methylpyrrolidone, tetrahydrofuran, or mixtures thereof. Compounds of formula (18), which are representative of the compounds of Formula (I), can be prepared by reacting compounds of formula (17) with 2-chloroacetaldehyde. The reaction is typically performed at elevated temperature in a solvent such as but not limited to N,N-dimethylformamide.

As shown in Scheme 5, a compound of formula (IA) wherein B, $R^2$, $R^3$, and m are as described herein, can be reacted with 4,6-dichloro-2-(methylthio)pyrimidine-5-carboxamide in the presence of a base such as but not limited to N,N-diisopropylethylamine or cesium carbonate to provide compounds of formula (15). The reaction typically requires the use of heat and a solvent such as but not limited to 1,4-dioxane or toluene. Aqueous ammonia can be reacted with compounds of formula (15) to provide compounds of formula (16). The reaction is typically performed at elevated temperature. Compounds of formula (17), can be prepared by reacting compounds of formula (16) with an organozinc compound of formula (2A), wherein Z, A, $R^1$, and n are as described herein and $X^A$ is a halide. The reaction typically involves the use of heat and a nickel or palladium catalyst such as but not limited to bis(triphenylphosphine)palladium (II) dichloride or tetrakis(triphenylphosphine)palladium(0)

Compounds of formula (5), wherein B, $R^2$, $R^3$ and m are as described herein, can be reacted with compounds of formula (19) to provide compounds of formula (20). The reaction may be performed at elevated temperature. Compounds of formula (21), which are representative of the compounds of Formula (I), can be prepared by reacting compounds of formula (20) with an organozinc compound of formula (2A), wherein Z, A, $R^1$, and n are as described herein and $X^A$ is a halide. The reaction typically involves the use of heat and a nickel or palladium catalyst such as but not limited to bis (triphenylphosphine)palladium(II) dichloride or tetrakis (triphenylphosphine)palladium(0) in a solvent such as but not limited to N-methylpyrrolidone, tetrahydrofuran, or mixtures thereof.

Scheme 7

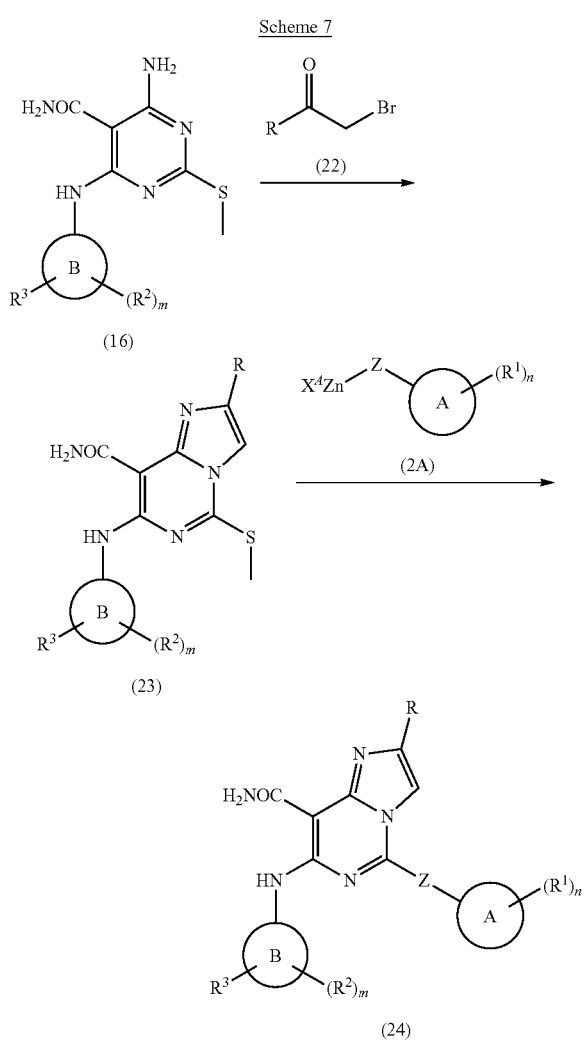

As shown in Scheme 7, compounds of formula (16) can be reacted with a compound of formula (22) to provide compounds of formula (23). The reaction is typically performed at an elevated temperature in a solvent such as but not limited to N,N-dimethylformamide. Compounds of formula (24), which are representative of the compounds of Formula (I), can be prepared by reacting compounds of formula (23) with an organozinc compound of formula (2A), wherein Z, A, $R^1$, and n are as described herein and $X^A$ is a halide. The reaction typically involves the use of heat and a nickel or palladium catalyst such as but not limited to bis(triphenylphosphine)palladium(II) dichloride or tetrakis(triphenylphosphine)palladium(0) in a solvent such as but not limited to N-methylpyrrolidone, tetrahydrofuran, or mixtures thereof.

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all CDC-7 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORE- TAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TRE-ANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like.

Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673. CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806

(mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukoptye alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFGx1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN®(Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETTIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXAMPLE 10

5-(2,6-dichlorobenzyl)-7-{[2-methoxy-4-(morpholin-4-ylcarbonyl)phenyl]amino}imidazo[1,2-c]pyrimidine-8-carboxamide

EXAMPLE 10A methyl 4-(5-carbamoyl-6-chloro-2-(methylthio)pyrimidin-4-ylamino)-3-methoxybenzoate A suspension of the product of Example 2D (1.0 g, 4.2 mmol), methyl 4-amino-3-methoxybenzoate (1.1 g, 6.3 mmol) and N,N-diisopropylethylamine (1.1 g, 8.4 mmol) in 30 mL of 1,4-dioxane in a sealed tube was heated at 120° C. for 18 hours and was allowed to cool to ambient temperature. The precipitate was filtered and washed with hexane (10 mL) to give the title compound. MS: 383 (M+H$^+$).

EXAMPLE 10B methyl 4-(6-amino-5-carbamoyl-2-(methylthio)pyrimidin-4-ylamino)-3-methoxybenzoate To a solution of the product of Example 10A (1.3 g, 3.4 mmol) in dimethylsulfoxide (50 mL) was added ammonium hydroxide (5.2 mL, 34 mmol). The mixture was heated to 100° C. for 4 hours and was allowed to cool to ambient temperature. Water (50 mL) was added and the precipitate was filtered and washed with ethanol (20 mL) to give the title compound. MS: 364 (M+H$^+$).

EXAMPLE 10C methyl 4-(6-amino-5-carbamoyl-2-(2,6-dichlorobenzyl)pyrimidin-4-ylamino)-3-methoxybenzoate A suspension of the product of Example 10B (1.1 g, 3.0 mmol), IM (2,6-dichlorobenzyl)zinc(II) bromide in tetrahydrofuran (30 mL, 30 mmol) and tetrakis(triphenylphosphine)palladium(0) (347 mg, 0.3 mmol) in tetrahydrofuran (50 mL) was heated in a sealed tube at 100° C. under nitrogen for 16 hours. The cooled mixture was washed with saturated ammonium chloride solution (50 mL) and extracted with ethyl acetate (3×50 mL). The combined organic phase was dried over anhydrous sodium sulfate, filtered, concentrated and purified by flash chromatography on silica gel (200-300 mesh) eluting with 3/1 petroleum ether/ethyl acetate to give the title compound. MS: 476 (M+H$^+$).

EXAMPLE 10D methyl 4-(8-carbamoyl-5-(2,6-dichlorobenzyl)imidazo[1,2-f]pyrimidin-7-ylamino)-3-methoxybenzoate A suspension of the product of Example 10C (770 mg, 1.6 mmol) and 2-chloroacetaldehyde (4.8 mL, 4.8 mmol, IM in acetic acid) in N,N-dimethylformamide (30 mL) was heated at 70° C. under nitrogen for 16 hours. The solvent was removed and the residue was diluted with ethyl acetate (50 mL) and washed with saturated sodium bicarbonate solution (20 mL). The organic layer was dried over anhydrous sodium sulfate, filtered, concentrated and purified by flash chromatography on silica gel (200-300 mesh) eluting with 1/1 petroleum ether/ethyl acetate to give the title compound. MS: 500 (M+H$^+$).

EXAMPLE 10E 4-(8-carbamoyl-5-(2,6-dichlorobenzyl)imidazo[1,2-f]pyrimidin-7-ylamino)-3-methoxybenzoic acid To a suspension of the product of Example 10D (385 mg, 0.77 mmol) in ethanol (20 mL) was added 2.5N sodium hydroxide solution (3.1 mL, 7.7 mmol) and the mixture was heated at 85° C. for 2 hours. The solvent was removed and the residue was diluted with water (10 mL) and adjusted to pH 1-2 with 1N hydrochloric acid. The precipitate was filtered and washed with ethanol (2×5 mL) to give the title compound. MS: 486 (M+H$^+$).

EXAMPLE 10F 5-(2,6-dichlorobenzyl)-7-(2-methoxy-4-(morpholine-4-carbonyl)phenylamino)imidazo[1,2-f]pyrimidine-8-carboxamide A suspension of the product of Example 10E (50 mg, 0.10 mmol), morpholine (13 mg, 0.153 mmol), (3-dimethylaminopropyl)ethyl-carbodiimide monohydrochloride (79 mg, 0.41 mmol), 1-hydroxy benzotriazole hydrate (56 mg, 0.41 mmol) and N,N-diisopropylethylamine (106 mg, 0.82 mmol) in N,N-dimethylmethanamide (10 mL) was stirred at ambient temperature for 20 hours. The solvent was removed and the residue was diluted with dichloromethane (50 mL) and washed with water (20 mL). The organic layer was dried over anhydrous sodium sulfate, filtered, concentrated and purified by preparative HPLC using a gradient of 10/90 to 80/20 acetonitrile/water (containing 0.1% trifluoroacetic acid) to give the title compound. $^1$H NMR (DMSO-d$_6$, 300 MHz): δ 12.42 (s, 1H), 9.71 (br, 1H), 8.25 (d, J=1.5 Hz, 1H), 7.87 (br, 1H), 7.67 (m, 3H), 7.54 (m, 1H), 7.41 (d, J=8.4 Hz, 1H), 6.98 (d, J=1.5 Hz, 1H), 6.42 (dd, J=8.4, 1.5 Hz, 1H), 4.86 (s, 2H), 3.86 (s, 3H), 3.46-3.64 (m, 8H). MS: 555 (M+H$^+$).

EXAMPLE 11

5-(2,6-dichlorobenzyl)-7-[(2-methoxy-4-{[2-(piperidin-1-yl)ethyl]carbamoyl}phenyl)amino][1,2,4]triazolo[4,3-c]pyrimidine-8-carboxamide

EXAMPLE 11A methyl 4-(5-carbamoyl-6-chloro-2-(methylthio)pyrimidin-4-ylamino)-3-ethoxybenzoate A mixture of the product of Example 2D (1.80 g, 76 mmol), methyl 4-amino-3-methoxybenzoate (2.05 g, 113 mmol) and N,N-diisopropylethylamine (1.96 g, 152 mmol) in 1,4-dioxane (50 mL) was heated in a sealed tube at 120° C. for 12 hours. After cooling, the solid was filtered and washed with ethanol to give the title compound. MS: 383 (M+H$^+$).

EXAMPLE 11B methyl 4-(5-carbamoyl-6-hydrazinyl-2-(methylthio)pyrimidin-4-ylamino)-3-methoxybenzoate To a solution of the product of Example 11A (1.2 g, 3.1 mmol) in tetrahydrofuran (400 mL) was added hydrazine hydrate (550 mg, 9.4 mmol) and the mixture was stirred at ambient temperature for 12 hours. After concentration, the residue was washed with methanol and dried under vacuum to give the title compound, which was used in the next step without further purification. MS: 379 (M+H$^+$).

EXAMPLE 11C methyl 4-(8-carbamoyl-5-(methylthio)-[1,2,4]triazolo[4,3-f]pyrimidin-7-ylamino)-3-methoxybenzoate To a solution of the product of Example 11B (1.0 g, 2.63 mmol) was added methyl orthoformate (100 mL) and the mixture was heated at reflux for 6 hours. After cooling to ambient temperature and concentration, the residue was recrystallized from methanol and dried under vacuum to give the title compound. MS: 389 (M+H$^+$).

EXAMPLE 11D methyl 4-(8-carbamoyl-5-(2,6-dichlorobenzyl)-[1,2,4]triazolo[4,3-f]pyrimidin-7-ylamino)-3-methoxybenzoate To a mixture of the product of Example 11C (800 mg, 2.1 mmol) and tetrakis(triphenylphosphine) palladium (230 mg, 0.2 mmol) was added 1M 2,6-dichlorobenzyl zinc bromide in tetrahydrofuran (10 mL, 10 mmol) and tetrahydrofuran (200 mL) under nitrogen. The mixture was heated at 60° C. for 12 hours. After cooling to ambient temperature, the mixture was diluted with ethyl acetate (200 mL) and washed with saturated aqueous sodium bicarbonate. The organic phase was separated and the aqueous phase was extracted with ethyl acetate (2×50 mL). The combined organic phase was washed with brine, dried over sodium sulfate, filtered and concentrated. The crude product was recrystallized from ethyl acetate to give the title compound. MS: 502 (M+H$^+$).

EXAMPLE 11E 4-(8-carbamoyl-5-(2,6-dichlorobenzyl)-[1,2,4]triazolo[4,3-f]pyrimidin-7-ylamino)-3-methoxybenzoic acid A suspension of the product of Example 11D (500 mg, 1.0 mmol) in 3M sodium hydroxide solution (4 mL, 12 mmol) and ethanol (30 mL) was heated at reflux for 6 hours. After cooling, the mixture was acidified with 1N aqueous HCl to pH 4-5. The solid was filtered and dried under vacuum to give the title compound. MS: 488 (M+H$^+$).

EXAMPLE 11F 5-(2,6-dichlorobenzyl)-7-(2-methoxy-4-(2-(piperidin-1-yl)ethylcarbamoyl)phenylamino)-[1,2,4]triazolo[4,3-f]pyrimidine-8-carboxamide A solution of the product of Example 11E (97.4 mg, 0.2 mmol), 2-(piperidin-1-yl)ethanamine (38.4 mg, 0.3 mmol), 2-(7-aza-1H-benzotriazole-1-yl)-1,1,3,3-tetramethyluroniumhexafluoro phosphate (152 mg, 0.4 mmol) and N,N-diisopropylethylamine (129 mg, 1.0 mmol) in N,N-dimethylformamide (15 mL) was stirred at ambient temperature for 5 hours. Water (30 mL) was added and the precipitate was filtered. The crude solid was purified by preparative HPLC using a gradient of 10/90 to 80/20 acetonitrile/water (containing 0.1% trifluoroacetic acid) to give the title compound. $^1$H NMR (CD$_3$OD, 300 MHz) δ: 8.19 (s, 1H), 7.75 (d, J=8.7 Hz, 1H), 7.42-7.57 (m, 4H), 7.10 (d, J=8.7 Hz, 1H), 4.48 (s, 2H), 4.05 (s, 3H), 3.75 (m, 4H), 3.38 (m, 2H), 3.04 (m, 2H), 1.85-2.06 (m, 6H). MS: 597 (M+H$^+$).

EXAMPLE 12

5-(2,6-dichlorobenzyl)-7-[(4-{[2-(dimethylamino)ethyl]carbamoyl}-2-methoxyphenyl)amino]imidazo[1,2-c]pyrimidine-8-carboxamide The title compound was obtained following the procedure described in Example 10, using N$^1$,N$^1$-dimethylethane-1,2-diamine in place of morpholine. $^1$H NMR (CD$_3$OD, 300 MHz): δ 8.05 (s, 1H), 7.50-7.62 (m, 4H), 7.45 (s, 1H), 7.03 (d, J=8.4 Hz, 1H), 4.90 (s, 2H), 4.01 (s, 3H), 3.73 (t, 2H), 3.24 (t, 2H), 2.88 (s, 6H). MS: 556 (M+H$^+$).

EXAMPLE 13

7-{[2-methoxy-4-(piperazin-1-yl)phenyl]amino}-5-(pyrrolidin-1-yl)imidazo[1,2-c]pyrimidine-8-carboxamide

EXAMPLE 13A tert-butyl 4-(3-methoxy-4-nitrophenyl)piperazine-1-carboxylate

A suspension of 4-fluoro-2-methoxy-1-nitrobenzene (15 g, 87 mmol), tert-butyl piperazine-1-carboxylate (19.59 g, 105.2 mmol) and potassium carbonate (24 g, 174 mmol) in N,N-dimethylformamide (150 mL) was heated at 80'C for 8 hours. After cooling to ambient temperature, the mixture was poured in water (500 mL). The precipitate was filtered and washed with ethanol to give the title compound. MS: 338 (M+H$^+$).

EXAMPLE 13B tert-butyl 4-(4-amino-3-methoxy phenyl)piperazine-1-carboxylate

A suspension of the product of Example 13A (6.3 g, 18.7 mmol) and Raney nickel (2.0 g) in 300 mL methanol was stirred under hydrogen at ambient temperature for 5 hours. The mixture was filtered through diatomaceous earth and the filtrate was concentrated. The residue was purified by flash chromatography on silica gel (200-300 mesh) eluting with a gradient of 2/1 to 1/1 petroleum/ethyl acetate to give the title compound.

EXAMPLE 13C tert-bury 14-(4-(5-carbamoyl-6-chloro-2-(methylthio)pyrimidin-4-ylamino)-3-methoxyphenyl)piperazine-1-carboxylate A solution of the product of Example 2D (6.0 g, 25 mmol), the product of Example 13B (8.1 g, 27 mmol) and diisopropylethylamine (6.4 g, 50 mmol) in 1,4-dioxane (200 mL) was stirred at 100° C. for 12 hours. The mixture was concentrated and the residue was used directly in the next step without further purification. MS: 509 (M+H$^+$).

EXAMPLE 13D tert-butyl 4-(4-(6-amino-5-carbamoyl-2-(methy thio)pyrimidin-4-ylamino)-3-methoxyphenyl)piperazine-1-carboxylate A solution of the product of Example 13C (12.7 g, 25 mmol) and 25% ammonia solution in water (6.8 g, 100 mmol) in 1,4-dioxane (200 mL) was heated in a sealed tube at 100° C. for 48 hours. After cooling, the solid was filtrated and washed with methanol to give the title compound. MS: 490 (M+H$^+$).

EXAMPLE 13E tert-butyl 4-(4-(8-carbamoyl-5-(methylthio)imidazo [1,2-f]pyrimidin-7-ylamino)-3-methoxyphenyl)piperazine-1-carboxylate A mixture of 2-chloro-1,1-diethoxyethane (305 mg, 2 mmol) in acetic acid (2 mL) was heated at 100° C. for 2 hours. After cooling, 0.3 mL of the mixture was added to a solution of the product of Example 13D (500 mg, 0.2 mmol) in N,N-dimethylformamide (5 mL) and the mixture was stirred at 60° C. for 6 hours. After cooling to ambient temperature, water (30 mL) was added and the mixture was neutralized with aqueous sodium bicarbonate solution. The mixture was extracted with ethyl acetate (3×30 mL) and the combined organic phase was washed with brine, dried over sodium sulfate, filtered, and concentrated. The residue was purified by flash chromatography on silica gel eluting with 100:1 dichloromethane/methanol to give the title compound. MS: 514 (M+H$^+$).

EXAMPLE 13F tert-butyl 4-(4-(8-carbamoyl-5-(pyrrolidin-1-yl)imidazo[1,2-f]pyrimidin-7-ylamino)-3-methoxyphenyl) piperazine-1-carboxylate A mixture of the product of Example 13E (60 mg, 0.11 mmol) in pyrrolidine (5 mL) was heated in a sealed tube at 120° C. under nitrogen for 4 hours. After cooling and concentration, the title compound was used directly in the next step without further purification. MS: 537 (M+H$^+$).

EXAMPLE 13G 7-(2-methoxy-4-(piperazin-1-yl)phenylamino)-5-(pyrrolidin-1-yl)imidazo[1,2-f]pyrimidine-8-carboxamide To a solution of the product of Example 13F (60 mg, 0.11 mmol) in dichloromethane (10 mL) was added trifluoroacetic acid (2 mL). After stirring at ambient temperature for 6 hours, the mixture was concentrated and the residue purified by preparative HPLC using a gradient of 10/90 to 30/20 acetonitrile/water (containing 0.1% trifluoroacetic acid) to give the title compound as the trifluoroacetate salt. $^1$H NMR (DMSO-d$_6$, 300 MHz): δ 12.16 (s, 1H), 812 (br, 3H), 8.26 (d, J=8.4 Hz, 1H), 7.93 (s, 1H), 7.31(s, 1H), 6.70 (s, 1H), 6.56 (d, J=8.4 Hz, 1H), 3.86 (s, 3H), 3.25-3.32(m, 12H), 1.97 (m, 4H). MS: 436 (M+H$^+$).

EXAMPLE 14

5-(2,6-di chlorobenzyl)-7-{[2-(methylsulfinyl)-4-(piperazin-1-yl)phenyl]amino}imidazo[1,2-c]pyrimidine-8-carboxamide

EXAMPLE 14A (5-bromo-2-nitrophenyl)(methyl)sulfane

A solution of sodium methanethiolate (2.25 g, 70.1 mmol) in water (50 mL) was added dropwise to a solution of 4-bromo-2-fluoro-1-nitrobenzene (6.42 g, 29.2 mmol) in N,N-dimethylformamide (150 mL) at 0° C. and the mixture was stirred for 1 hour. The mixture was filtered and the solid washed with water (3×150 mL) to give the title compound.

EXAMPLE 14B 4-bromo-2-(methylsulfinyl)-1-nitrobenzene

Sodium periodate (4.2 g, 16.34 mmol) in water (8 mL) was added to the solution of the product of Example 14A (4.01 g, 16.34 mmol) in 2/1 methanol/tetrahydrofuran (60 mL) and the mixture stirred for 1 hour. The mixture was diluted with ethyl ether, washed with water and saturated aqueous sodium bicarbonate, dried over sodium sulfate, filtered and concentrated. The residue was purified by flash chromatography on silica gel (200-300 mesh) eluting with 3/1 ether/ethyl acetate to provide the title compound.

EXAMPLE 14C tert-butyl 4-(3-(methylsulfinyl)-4-nitrophenyl)piperazine-1-carboxylate A mixture of the product of Example 14B (45 mg, 0.17 mmol), tert-butyl piperazine-1-carboxylate (38 mg, 0.2 mmol), tetrabutylammonium bromide (6 mg, 0.02 mmol) and potassium carbonate (35 mg, 0.26 mmol) in dry DMSO (5 mL) was heated under nitrogen at 120° C. for 3 hours. The mixture was added to water (20 mL) and aqueous hydrogen chloride solution (20 mL) and washed with ethyl acetate. The aqueous phase was basified with 2.5N sodium hydroxide solution and extracted with ethyl acetate (3×20 mL). The combined organic phase was dried over sodium sulfate, filtered, and concentrated. The residue was purified by flash chromatography on silica gel eluting with 40/1 dichloromethane/methanol to give the title compound.

EXAMPLE 14D tert-butyl 4-(4-amino-3-(methylsulfinyl)phenyl)piperazine-1-carboxylate To a solution of the product of Example 14C (54 mg, 0.146 mmol) in tetrahydrofuran (2.5 mL) and methanol (2.5 mL) at ambient temperature was added slowly zinc powder (95 mg, 1.46 mmol) and acetic acid (0.1 mL). The mixture was stirred for 1 hour, followed by addition of a saturated aqueous sodium bicarbonate solution. The mixture was stirred for 1 hour and filtered through diatomaceous earth, followed by extraction with ethyl acetate (25 mL). The organic layer was washed with saturated brine solution, dried over sodium sulfate, filtered, and concentrated. The residue was purified by flash chromatography on silica gel (200-300 mesh) eluting with 95/5 dichloromethane/methanol to provide the title compound.

EXAMPLE 14E tert-butyl 4-(4-(3-carbamoyl-2-chloro-6-(methylthio)pyridin-4-ylamino)-3-(methylsulfinyl)phenyl)piperazine-1-carboxylate To a mixture of the product of Example 14D (630 mg, 1.86 mmol) and the product of Example 2D (419 mg, 1.77 mmol) in 1,4-dioxane (4 mL) was added N-ethyl-N-isopropylpropan-2-amine (458 mg, 3.54 mmol) and the mixture was heated in a sealed tube at 100° C. for 40 hours. After cooling to ambient temperature, the solvent was removed under vacuum and the residue was purified by flash chromatography on silica gel (200-300 mesh) 40/1 dichloromethane/methanol to give the title compound. MS: 541 (M+H$^+$).

EXAMPLE 14F tert-butyl 4-(4-(2-amino-3-carbamoyl-6-(methylthio)pyridin-4-ylamino)-3-(methylsulfinyl)phenyl)piperazine-1-carboxylate A mixture of the product of Example 14E (637 mg, 1.18 mmol) and 25% aqueous ammonia (2 mL) in 1,4-dioxane (3 mL) was heated in a seated tube at 80° C. for 24 hours. After cooling to ambient temperature, the mixture was concentrated, diluted with ethyl acetate, washed with water, dried over sodium sulfate, filtered and concentrated. The residue was purified by flash chromatography on silica gel eluting with 25/1 dichloromethane/methanol to give the title compound. MS: 521 (M+H$^+$).

EXAMPLE 14G tert-butyl 4-(4-(8-carbamoyl-5-(methylthio)H-imidazo[1,2-a]pyridin-7-ylamino)-3-(methylsulfinyl)phenyl)piperazine-1-carboxylate To a solution of the product of Example 14F (400 mg, 0.77 mmol) in N,N-dimethylformamide (10 mL) was added 2-chloroacetaldehyde (1.5 mL, 1M in acetic acid) and the solution was heated at 60° C. for 2 days. The mixture was concentrated and the residue was purified by flash chromatography on silica gel eluting with 50/1 dichloromethane/methanol to give the title compound. MS: 546 (M+H$^+$).

EXAMPLE 14H 5-(2,6-dichlorobenzyl)-7-(2,6-difluoro-4-(piperazin-1-yl)phenylamino)-[1,2,4]triazolo[4,3-a]pyridine-8-carboxamide To a solution of the product of Example 14G (100 mg, 0.183 mmol) and tris(dibenzylideneacetone) dipalladium (21 mg, 0.018 mmol) in tetrahydrofuran (2 mL) was added 0.5M (2,6-dichlorobenzyl)zinc(II) chloride in tetrahydrofuran (3 mL, 1.83 mmol) and the solution was heated at reflux for 16 hours. After cooling to ambient temperature, the mixture was concentrated and purified by flash chromatography on silica gel eluting with 30/1 dichloromethane/methanol to give the title compound. MS: 658 (M+H$^+$).

EXAMPLE 14I tert-butyl 4-(4-(8-carbamoyl-5-(methylthio)H-imidazo[1,2-a]pyridin-7-ylamino-3-(methylsulfinyl)phenyl)piperazine-g801-carboxylate To a solution of the product of Example 14H (102 mg, 0.16 mmol) in dichloromethane (5 mL) was added trifluoroacetic acid (4 mL). After stirring at ambient temperature for 3 hours, the mixture was concentrated and the residue was purified by preparative HPLC using a gradient of 10/90 to 75/25 acetonitrile in water (containing 0.1% trifluoroacetic acid) to give the title compound. $^1$H NMR (CD$_3$OD, 300 MHz): δ 7.96 (d, J=1.5 Hz, 1H), 7.57 (d, J=1.5 Hz, 1H), 7.34 (m, 2H), 7.24 (m, 2H), 7.11 (d, J=9.0 Hz, 1H), 6.86 (dd, J=3.0 Hz, J=8.7 Hz, 1H), 4.72 (s, 2H), 3.47 (m, 8H), 2.59 (s, 3H). MS: 558 (M+H$^+$)

EXAMPLE 15

5-(2,6-dichlorobenzyl)-7-{[2,5-difluoro-4-(piperazin-1-yl)phenyl]amino}[1,2,4]triazolo[4,3-c]pyrimidine-8-carboxamide

EXAMPLE 15A

N,N-dibenzyl-4-bromo-2,5-difluoroaniline

To a mixture of 4-bromo-2,5-difluoroaniline (8 g, 39 mmol) and potassium carbonate (16 g, 116 mmol) in acetonitrile (200 mL) was added (bromomethyl)benzene (14.5 g, 85 mmol). After refluxing for 20 hours, the mixture was filtered and the filtrate was concentrated. The residue was purified by flash chromatography on silica gel (200-300 mesh) eluting with 5/1 petroleum ether/ethyl acetate to give the title compound. MS: 388 (M+H$^+$).

EXAMPLE 15B tert-butyl 4-(4-(dibenzylamino)-2,5-difluorophenyl)piperazine-1-carboxylate A mixture of the product of Example 15A (5.12 g, 13.2 mmol), tert-butyl piperazine-1-carboxylate (2.95 g, 15.8 mmol), palladium diacetate (149 mg, 0.66 mmol), (±)-2,2'- bis(diphenylphosphino)-1,1'-binaphthalene (616 mg, 0.99 mmol) and cesium carbonate (8.61 g, 26.4 mmol) in toluene (100 mL) was heated at 100° C. under nitrogen for 16 hours. After cooling, the mixture was filtered and the filtrate was concentrated. The residue was purified by flash chromatography on silica gel (200-300 mesh) eluting with 5/1 petroleum ether/ethyl acetate to give the title compound. MS: 494 (M+H$^+$).

EXAMPLE 15C tert-butyl 4-(4-amino-2,5-difluorophenyl)piperazine-1-carboxylate To a solution of the product of Example 15B (4 g, 8 mmol) in methanol (100 mL) was added 10% palladium on carbon (400 mg). The mixture was stirred at room temperature under hydrogen for 16 hours. The catalyst was filtered off and the filtrate was concentrated to give the title compound. MS: 314 (M+H$^+$).

EXAMPLE 15D tert-butyl 4-(4-(5-carbamoyl-6-chloro-2-(methylthio)pyrimidin-4-ylamino)-2,5-difluorophenyl)piperazine-1-carboxylate A mixture of the product of Example 15C (337 mg, 1.42 mmol), the product of Example 2D (446 mg, 1.42 mmol), and N,N-diisopropylethylamine (550 mg, 4.26 mmol) in 1,4-dioxane (10 mL) was heated in a sealed tube at 100° C. for 16 hours. The mixture was concentrated and the residue was purified by flash chromatography on silica gel (200-300 mesh) eluting with 98/2 petroleum ether/ethyl acetate to give the title compound. MS: 515 (M+H$^+$).

EXAMPLE 15E tert-butyl 4-(4-(5-carbamoyl-6-hydrazinyl-2-(methylthio)pyrimidin-4-ylamino)-2,5-difluorophenyl)piperazine-1-carboxylate To a solution of the product of Example 15D (3.53 mg, 0.69 mmol) in 1,4-dioxane (5 mL) was added hydrazine hydrate (0.3 mL). After stirring at ambient temperature for 4 hours, the mixture was concentrated. The residue was washed with hexane and dried under vacuum to give the crude title compound, which was used in the next step without further purification (281 mg, 80%). MS: 511 (M+H$^+$).

EXAMPLE 15F tert-butyl 4-(4-(8-carbamoyl-5-(methylthio)-[1,2,4]triazolo[4,3-c]pyrimidin-7-ylamino)-2,5-difluorophenyl)piperazine-1-carboxylate To a solution of the product of Example 15E (281 mg, 0.55 mmol) in dimethylacetamide (5 mL) was added methyl orthoformate (2 mL). The mixture was stirred at ambient temperature for 1 hour and at 60° C. for 4 hours. After cooling to ambient temperature, 9/1 petroleum ether/ethyl acetate (50 mL) was added and the precipitate was filtered. The solid was washed with petroleum ether and dried under vacuum to give the title compound. MS: 521 (M+H$^+$).

EXAMPLE 15G tert-butyl 4-(4-(8-carbamoyl-5-(2,6-dichlorobenzyl)-[1,2,4]triazolo[4,3-c]pyrimidin-7-ylamino)-2,5-difluorophenyl)piperazine-1-carboxylate To a mixture of the product of Example 15F (220 mg, 0.4 mmol) and tetrakis(triphenylphosphine) palladium (49 mg, 0.04 mmol) was added 0.5M 2,5-difluorobenzyl zinc bromide in tetrahydrofuran (4 mL, 2 mmol) under nitrogen. The mixture was heated at 70° C. for 16 hours. After cooling to ambient temperature, the mixture was diluted with dichloromethane (50 mL) and washed with saturated aqueous sodium bicarbonate. The organic phase was separated and the aqueous phase was extracted with dichloromethane (2×20 mL). The combined organic phase was washed with brine, dried over sodium sulfate, filtered and concentrated. The residue was purified by flash chromatography on silica gel (200-300 mesh) eluting with 97/3 dichloromethane/methanol to give the title compound. MS: 633 (M+H$^+$).

EXAMPLE 15H 5-(2,6-dichlorobenzyl)-7-(2,5-difluoro-4-(piperazin-1-yl)phenylamino)-[1,2,4]triazolo[4,3-c]pyrimidine-8-carboxamide To a solution of the product of Example 15G (230 mg, 0.36 mmol) in dichloromethane (8 mL) was added trifluoroacetic acid (2 mL) dropwise. The mixture was stirred at ambient temperature for 4 hours and concentrated. The solid was washed with ethanol and dried under vacuum to give the title compound. $^1$H NMR (DMSO-d$_6$, 300 MHz): δ 12.38 (d, J=1.5 Hz, 1H), 9.71 (s, 1H), 8.95 (d, J=2.1 Hz, 1H), 8.76 (br. s, 2H), 8.14 (d, J=2.1 Hz, 1H), 7.56-7.54 (m, 2H), 7.45-7.40 (m, 1H), 7.25-7.17 (m, 1H), 7.05-6.99 (m, 1H), 4.96 (s, 2H), 3.24-3.23 (m, 4H), 3.15-3.11 (m, 4H). MS: 533 (M+H$^+$).

EXAMPLE 16

5-(2,6-dichlorobenzyl)-7-{[2,6-difluoro-4-(piperazin-1-yl)phenyl]amino}[1,2,4]triazolo[4,3-c]pyrimidine-8-carboxamide

EXAMPLE 16A 4-bromo-2,6-difluorobenzenamine 2,6-Difluorobenzeneamine (6.0 g, 45 mmol) was dissolved in acetic acid (20 mL) and bromine (2.4 mL, 50 mmol) was added and the mixture was stirred at ambient temperature for 15 minutes. After concentration, the residue was treated with aqueous sodium carbonate and extracted with ethyl acetate. The organic extract was dried over sodium sulfate, filtered, and concentrated. The residue was purified by flash chromatography on silica gel (200-300 mesh) eluting with 25/1 petroleum ether/ethyl acetate to give the title compound. MS: 208 (M+H$^+$).

EXAMPLE 16B

N,N-dibenzyl-4-bromo-2,6-difluorobenzenamine

A mixture of the product of Example 16A (1.1 g, 5.3 mmol), benzyl bromide (949 mg, 0.66 ml) and potassium bicarbonate (1.46 mg, 10.6 mmol) in N,N-dimethylformamide (3 mL) was stirred at ambient temperature until TLC indicated no starting material remained. Ethyl acetate was added, and the mixture was washed with water and brine and dried over anhydrous sodium sulfate. After filtration and concentration, the residue was purified by flash chromatography on silica gel (200-300 mesh) eluting with 10/1 petroleum ether/dichloromethane to give the title compound.

EXAMPLE 16C tert-butyl 4-(4-(dibenzylamino)-3,5-difluorophenyl) piperazine-1-carboxylate A mixture of the product of Example 16B (490 mg, 1.3 mmol), tert-butyl piperazine-1-carboxylate (258 mg, 1.4 mmol), palladium diacetate (14 mg, 0.06 mmol), (±)-2,2'-bis (diphenylphosphino)-1,1'-binaphthalene (59 mg, 0.09 mmol) and cesium carbonate (848 mg, 2.6 mmol) in 1,4-dioxane (10 mL) was heated at reflux for 16 hours. The mixture was filtered through diatomaceous earth and the filtrate was concentrated. The residue was purified by flash chromatography on silica gel (200-300 mesh) eluting with 8/1 petroleum ether/ ethyl acetate to give the title compound.

EXAMPLE 16D tert-butyl 4-(4-amino-3,5-difluorophenyl)piperazine-1-carboxylate

A mixture of the product of Example 16C (560 mg, 1.1 mmol) and 10% palladium on carbon in methanol (30 mL) was stirred at ambient temperature under hydrogen until TLC indicated no starting material remained. The mixture was filtered through diatomaceous earth and the filtrate was concentrated. The residue was purified by flash chromatography on silica gel (200-300 mesh) eluting with 4/1 petroleum ether/ ethyl acetate to give the title compound. MS: 314 (M+H$^+$),

EXAMPLE 16E tert-butyl 4-(4-(5-carbamoyl-6-chloro-2-(methylthio) pyrimidin-4-ylamino)-3,5-difluorophenyl)piperazine-1-carboxylate A mixture of the product of Example 16D (695 mg, 2.22 mmol), the product of Example 2D (526 mg, 2.22 mmol) and N-ethyl-N-isopropylpropan-2-amine (286 mg, 4.44 mmol) in 1,4-dioxane (4 mL) was heated at 100° C. for 16 hours. The mixture was concentrated and the residue was purified by flash chromatography on silica gel (200-300 mesh) eluting with 5/1 petroleum/ethyl acetate to give the title compound. MS: 537 (M+H$^+$).

EXAMPLE 16F tert-butyl 4-(4-(5-carbamoyl-6-hydrazinyl-2-(methylthio)pyrimidin-4-ylamino)-3,5-difluorophenyl) piperazine-1-carboxylate To a solution of the product of Example 16E (380 mg, 0.74 mmol) in 1,4-dioxane (10 mL) was added hydrazine (185 mg, 3.68 mmol) and the mixture was stirred at ambient temperature for 3 hours. The mixture was concentrated and the residue was recrystallized from ethanol to give the title compound. MS: 495 (M+H$^+$).

EXAMPLE 16G tert-butyl 4-(4-(8-carbamoyl-5-(methylthio)-[1,2,4] triazolo[4,3-c]pyrimidin-7-ylamino)-3,5-difluorophenyl)piperazine-1-carboxylate A solution of the product of Example 16F (615 mg, 1.2 mmol) and trimethoxymethane (5 g, 46.9 mmol) in N,N-dimethylformamide (10 mL) was stirred at ambient temperature for 1 hour and at 55° C. for 3 hours. The mixture was filtered to give the title compound. MS: 495 (M+H$^+$).

EXAMPLE 16H tert-butyl 4-(4-(8-carbamoyl-5-(2,6-dichlorobenzyl)-[1,2,4]triazolo[4,3-c]pyrimidin-7-ylamino)-3,5-difluorophenyl)piperazine-1-carboxylate The title compound was obtained following the procedure described in Example 14H, using the product of Example 16G in place of the product of Example 14G. MS: 633 (M+H$^+$).

EXAMPLE 16I 5-(2,6-dichlorobenzyl)-7-(2,6-difluoro-4-(piperazin-1-yl)phenylamino)-[1,2,4]triazolo[4,3-c]pyrimidine-8-carboxamide The title compound was obtained following the procedure described in Example 14I, using the product of Example 16H in place of the product of Example 14H. $^1$H NMR (DMSO-d$_6$, 300 MHz): δ 10.71 (s, 1H), 9.58 (s, 1H), 8.61 (br. s, 2H), 8.02 (s, 1H), 7.31 (m, 2H), 6.47 (s, 1H), 6.43(s, 1H), 4.76 (s, 2H), 3.36 (m, 4H), 3.25(m, 4H). MS: 633 (M+H$^+$).

EXAMPLE 17

5-(2,6-dichlorobenzyl)-7-{[3-methyl-4-(piperazin-1-yl)phenyl]amino}[1,2,4]triazolo[4,3-c]pyrimidine-8-carboxamide

EXAMPLE 17A tert-butyl 4-(2-methyl-4-nitrophenyl)piperazine-1-carboxylate

A mixture of 1-bromo-2-methyl-4-nitrobenzene (5.16 g, 24 mmol), tert-butyl piperazine-1-carboxylate (4.46 g, 24 mmol), 2-dicyclohexylphosphino-2',4',6'-triisopropylbiphenyl (1.15 g, 2.4 mmol), cesium carbonate (15.65 g, 48 mmol) and tris(dibenzylideneacetone)dipalladium (2.21 g, 2.4 mmol) in 1,4-dioxane (120 mL) was heated at 100° C. for 16 hours. The solid was filtered and the filtrate was concentrated to give the crude product which was purified by flash chromatography on silica gel (200-300 mesh) eluting with 20/1 petroleum ether/ethyl acetate to give the title compound. MS: 322 (M+H$^+$).

EXAMPLE 17B tert-buty 14-(4-amino-2-methyl-phenyl)piperazine-1-carboxylate

A suspension of the product of Example 17A (3.10 g, 9.7 mmol) and 10% palladium on carbon (310 mg) in methanol (200 mL) was stirred under hydrogen at ambient temperature for 5 hours. The catalyst was filtered off and the filtrate was concentrated. Purification by flash chromatography on silica gel (200-300 mesh) eluting with 8/1 petroleum ether/ethyl acetate gave the title compound. MS: 292 (M+H⁺).

EXAMPLE 17C tert-butyl-4-(4-(5-carbamoyl-6-chloro-2-(methylthio) pyrimidin-4-ylamino)-2-methylphenyl)piperazine-1-carboxylate A suspension of the product of Example 17B (640 mg, 2.2 mmol), the product of Example 2D (474 mg, 2 mmol) and ethyldiisopropylamine (517 mg, 4 mmol) in 1,4-dioxane (10 mL) was stirred at 80° C. for 18 hours. The mixture was concentrated and the residue was purified by flash chromatography on silica gel (200-300 mesh) eluting with 4/1 petroleum ether/ethyl acetate to give the title compound. MS: 493 (M+H⁺).

EXAMPLE 17D tert-butyl 4-(4-(5-carbamoyl-6-hydrazinyl-2-(methylthio)pyrimidin-4-ylamino)-2-methyl-phenyl)piperazine-1-carboxylate To a suspension of the product of Example 17C (246 mg, 0.5 mmol) in 1,4-dioxane (10 mL) was added 85% hydrazine hydrate (125 mg, 2.5 mmol) dropwise. The mixture was stirred at room temperature for 3 hours, extracted with ethyl acetate and the organic layer was washed with water, dried over sodium sulfate, filtered and concentrated. The residue was washed with petroleum ether to provide the title compound. MS: 489 (M+H⁺).

EXAMPLE 17E tert-butyl 4-(4-(8-carbamoyl-5-(methylthio)-[1,2,4] triazolo[4,3-f]pyrimidin-7-ylamino)-2-methylphenyl) piperazine-1-carboxylate To a suspension of the product of Example 17D (246 mg, 0.5 mmol) in N,N-dimethylformamide (10 mL) was added trimethyl orthoformate (2.07 g, 19.5 mmol) and the mixture stirred at ambient temperature for 1 hour and at 60° C. for 3 hours. The solid was filtered and washed with ethanol to provide the title compound. MS: 499 (M+H⁺).

EXAMPLE 17F tert-butyl 4-(4-(5-(2,6-dichlorobenzyl)-8-carbamoyl-[1,2,4]triazolo[4,3-f]pyrimidin-7-ylamino)-2-methylphenyl)piperazine-1-carboxylate To a mixture of the product of Example 17E (249 mg, 0.5 mmol) and tetrakis(triphenylphosphine) palladium (58 mg, 0.05 mmol) was added 0.5M dichlorobenzyl zinc bromide in tetrahydrofuran (10 mL, 5 mmol) under nitrogen and the mixture was stirred at 100° C. for 24 hours. After cooling to ambient temperature, ammonium chloride was added and the mixture was extracted with ethyl acetate and washed with water. The organic layer was dried over sodium sulfate, filtered and concentrated to provide the title compound which was used in the next step without further purification. MS: 611 (M+H⁺).

EXAMPLE 17G 5-(2,6-dichlorobenzyl)-7-(3-methyl-4-(piperazin-1-yl)phenylamino)-[1,2,4]triazolo[4,3-f]pyrimidine-8-carboxamide To a suspension of the product of Example 17F (1.0 g, 1.6 mmol) in methanol (10 mL) was added trifluoroacetic acid (5 mL) and the mixture was stirred at 45° C. for 3 hours. After concentration, the residue was purified by preparative HPLC using a gradient of 10/90 to 80/20 acetonitrile/water (containing 0.1% trifluoroacetic acid) to provide the title compound. ¹H NMR (DMSO-d₆, 300 MHz): δ 12.20 (s, 1 H), 9.67 (s, 1 H), 8.99 (s, 1 H), 8.65 (br, 2 H), 8.06 (s, 1 H), 7.46-7.64 (m, 3 H), 7.03 (m, 1 H), 6.89 (d, J=9.0 Hz, 1 H), 6.67 (d, J=9.0 Hz, 1 H), 4.97 (s, 2 H), 3.25 (m, 4 H), 2.95 (m, 4 H), 2.13 (s, 3 H). MS: 511 (M+H⁺).

EXAMPLE 18

6-{[3-chloro-4-(piperazin-1-yl)phenyl]amino}-4-(2, 6-dichlorobenzyl)-1H-imidazo[4,5-c]pyridine-7-carboxamide

EXAMPLE 18A tert-butyl 4-(2-chloro-4-nitrophenyl)piperazine-1-carboxylate

A mixture of 1-bromo-2-chloro-4-nitrobenzene (1 g, 4.2 mmol), tert-butyl piperazine-1-carboxylate (0.86 g, 4.6 mmol), potassium carbonate (878 mg, 6.4 mmol) and tetrabutyl ammonium bromide (137 mg, 0.42 mmol) in dimethylsulfoxide (20 mL) was heated at 125° C. for 3 hours. After cooling to ambient temperature, the mixture was diluted with water and extracted with ethyl acetate. The organic layer was washed with brine, dried over anhydrous sodium sulfate, filtered, and concentrated. The residue was purified by flash chromatography on silica gel eluting with 5/1 petroleum ether/ethyl acetate to give the title compound. MS: 342 (M+H⁺)

EXAMPLE 18B tert-butyl 4-(4-amino-2-chlorophenyl)piperazine-1-carboxylate

To a solution of the product of Example 18A (1.5 g, 4.4 mmol) in 1:1 tetrahydrofuran/methanol (80 mL) at ambient temperature was slowly added zinc power (1.43 g, 22 mmol) and acetic acid (5 mL). The mixture was stirred for 1 hour, and saturated aqueous sodium hydrogen carbonate solution was added. The mixture was stirred for 1 hour and filtered, and extracted with ethyl acetate. The organic layer was washed with brine, dried over anhydrous sodium sulfate, filtered, and concentrated. The residue was purified by flash chromatography on silica gel eluting with 5/1 petroleum ether/ethyl acetate to give title compound. MS: 312 (M+H⁺).

EXAMPLE 18C tert-butyl 4-(2-chloro-4-(7-cyano-4-(2,6-dichlorobenzyl)-1-((2-(trimethylsilyl)ethoxy)methyl)-1H-imidazo[4,5-c]pyridin-6-ylamino)phenyl)piperazine-1-carboxylate A mixture of the product of Example 8I (234 mg, 0.5 mmol), the product of Example 18B (156 mg, 0.5 mmol), tricyclohexylphosphine (42 mg, 0.15 mmol), palladium diacetate (18 mg, 0.08 mmol) and cesium carbonate (326 mg, 1 mmol) in toluene (50 mL) was heated at 100° C. for 14 hours under nitrogen. After cooling, the mixture was filtered, concentrated and purified by flash chromatography on silica gel (200-300 mesh) eluting with 5/1 petroleum ether/ethyl acetate to provide the title compound. MS: 742 (M+H$^+$).

EXAMPLE 18D 6-(3-chloro-4-(piperazin-1-yl)phenylamino)-4-(2,6-dichlorobenzyl)-1H-imidazo[4,5-c]pyridine-7-carboxamide To a solution of the product of Example 18C (100 mg, 0.14 mmol) in concentrated sulfuric acid (5 mL) was added water (1 mL) at 0° C. and the mixture was heated at 95° C. for 20 minutes. After cooling to ambient temperature, water (3 mL) was added, and the mixture was adjusted to pH 8-9 with saturated aqueous sodium bicarbonate and extracted with dichloromethane (3×20 mL). The combined organic phase was concentrated and the residue was purified by preparative HPLC using a gradient of 10/90 to 75/25 acetonitrile in water (containing 0.1% trifluoroacetic acid) to give the title compound. $^1$H NMR (DMSO-d$_6$, 300 MHz): δ 13.62 (s, 1 H), 11.85 (s, 1 H), 9.62 (s, 1 H), 8.69 (s, 2 H), 8.61 (s, 1 H), 7.85 (br, 1 H), 7.58 (m, 1 H), 7.55 (m, 1 H), 7.52 (d, J=2.4 Hz, 1 H), 7.42-7.37 (m, 1 H), 7.15 (dd, J=9, 2.4 Hz, 1 H), 6.85 (d, J=9 Hz, 1 H), 4.74 (s, 2 H), 3.27 (m, 4 H), 2.08-1.70 (m, 4 H). MS: 530 (M+H$^+$).

EXAMPLE 19

5-(2-chlorobenzyl)-7-{[2-methoxy-4-(piperazin-1-yl)phenyl]amino}imidazo[1,2-c]pyrimidine-8-carboxamide

EXAMPLE 19A tert-butyl 4-(4-(8-carbamoyl-5-(2-chlorobenzyl)imidazo[1,2-f]pyrimidin-7-ylamino)-3-methoxyphenyl)piperazine-1-carboxylate A solution of the product of Example 13E (103 mg, 0.2 mmol), 1M (2-chlorobenzyl) zinc(II) bromide in tetrahydrofuran (1.0 mL, 1.0 mmol) and tetrakis(triphenylphosphine)palladium(0) (12 mg, 0.01 mmol) in tetrahydrofuran (5 mL) was stirred at 65° C. under nitrogen for 12 hours. Ammonium chloride solution (15 mL) was added and the mixture was extracted with ethyl acetate (3×30 mL). The combined organic layer was washed with brine, dried over anhydrous sodium sulfate, filtered, and concentrated. The residue was purified by flash chromatography on silica gel (200-300 mesh) eluting with 30/1 dichloromethane/methanol to give the title compound. MS: 592 (M+H$^+$).

EXAMPLE 19B 7-(2-methoxy-4-(piperazin-1-yl)phenylamino)-5-phenylimidazo[1,2-f]pyrimidine-8-carboxamide To a solution of the product of Example 19A (95 mg, 0.16 mmol) in dichloromethane (10 mL) was added trifluoroacetic acid (2 mL). After stirring at ambient temperature for 6 hours, the mixture was concentrated and the residue was purified by preparative HPLC using a gradient of 10/90 to 30/20 acetonitrile/water (containing 0.1% trifluoroacetic acid) to give the title compound as a trifluoroacetate salt. $^1$H NMR (DMSO-d$_6$, 300 MHz): δ 12.09 (s, 1H), 9.67 (s, 1H), 8.73 (br, 2H), 8.12 (s, 1H), 7.73 (s, 1H), 7.45-7.62 (m, 5H), 7.26 (d, J=9.0 Hz, 1H), 6.61 (s, 1H), 5.95 (d, J=9.0 Hz, 1H), 4.67 (s, 2H), 3.83 (s, 3H), 3.27(m, 8H). MS: 492(M+H$^+$).

EXAMPLE 20

4-(2,6-dichlorobenzyl)-6-{[2,5-difluoro-4-(piperazin-1-yl)phenyl]amino}-1H-imidazo[4,5-c]pyridine-7-carboxamide

EXAMPLE 20A tert-butyl 4-(4-((7-cyano-4-(2,6-dichlorobenzyl)-1-((2-(trimethylsilyl)ethoxy)methyl)-1H-imidazo[4,5-c]pyridin-6-yl)amino)-2,5-difluorophenyl)piperazine-1-carboxylate A mixture of the product of Example 8I (200 mg, 0.43 mmol), the product of Example 15C (160 mg, 0.51 mmol), palladium acetate (8 mg, 0.034 mmol), tricyclohexylphosphine (19 mg, 0.068 mmol) and cesium carbonate (278 mg, 0.85 mmol) in toluene (3 mL) was degassed with nitrogen 6 times and the mixture was heated at 110° C. for 15 hours. After cooling to ambient temperature, the mixture was concentrated and purified by flash chromatography on silica gel (200-300 mesh) eluting with 6/1 petroleum ether/ethyl acetate to give the title compound. MS: 744 (M+H$^+$).

EXAMPLE 20B 4-(2,6-dichlorobenzyl)-4-((2,5-difluoro-4-(piperazin-1-yl)phenyl)amino)-1H-imidazo[4,5-c]pyridine-7-carboxamide The product of Example 20A (0.169 g, 0.227 mmol) was dissolved in cool (0° C.) concentrated sulfuric acid (4 mL) and water (0.5 mL) was added. The solution was heated at 85° C. for 0.5 hours. After cooling to ambient temperature, the mixture was neutralized with saturated aqueous sodium bicarbonate and extracted with dichloromethane. The organic phase was dried over anhydrous sodium sulfate, filtered, concentrated and purified by preparative HPLC using a gradient of 10/90 to 75/25 acetonitrile in water (containing 0.1% trifluoroacetic acid) to give the title compound. $^1$H NMR (DMSO-d$_6$, 300 MHz): δ 13.76 (brs, 1 H), 12.03 (s, 1 H), 9.59 (s, 1 H), 8.74 (brs, 2 H), 8.67 (s, 1 H), 7.92 (s, 1 H), 7.83 (dd, J=14.7 Hz, 8.1 Hz, 1 H), 7.55 (d, J=8.1 Hz, 2 H), 7.40 (t, J=8.1 Hz, 1 H), 7.03 (dd, J=12.9, 8.1 Hz, 1 H), 4.76 (s, 2 H), 3.27 (m, 4 H), 3.12 (m, 4 H). MS: 532 (M+H$^+$).

EXAMPLE 21

7-{[2-methoxy-4-(piperazin-1-yl)phenyl]amino}-5-(piperazin-1-yl)imidazo[1,2-c]pyrimidine-8-carboxamide

EXAMPLE 21A tert-butyl 4-(7-(4-(4-(tert-butoxycarbonyl)piperazin-1-yl)-2-methoxyphenylamino)-8-carbamoylimidazo[1,2-f]pyrimidin-5-yl)piperazine-1-carboxylate To a solution of the product of Example 13E (100 mg, 0.19 mmol) in N-methyl-2-pyrrolidone (5 mL) was added Tert-butyl piperazine-1-carboxylate (177 mg, 0.95 mmol). After heating in a sealed tube at 150° C. for 16 hours, the mixture was cooled to ambient temperature, poured into water (50 mL) and extracted with ethyl acetate (2×50 mL). The combined organic phase was washed with brine (30 mL), dried over anhydrous sodium sulfate, filtered and concentrated. The residue was purified by flash chromatography on silica gel eluting with 100:1 dichloromethane/methanol to give the crude product. MS: 652 (M+H$^+$).

EXAMPLE 21B 7-(2-methoxy-4-(piperazin-1-yl)phenylamino)-5-(piperazin-1-yl)imidazo[1,2-f]pyrimidine-8-carboxamide To a solution of the product of Example 21A (120 mg, 0.19 mmol) in dichloromethane (12 mL) was added trifluoroacetic acid (3 mL). After stirring at ambient temperature for 5 hours, the mixture was concentrated and the residue was purified by preparative HPLC using a gradient of 10/90 to 30/20 acetonitrile/water (containing 0.1% trifluoroacetic acid) to give the title compound as the trifluoroacetate salt. $^1$H NMR (300 MHz, CD$_3$OD): 7.99 (d, =8.4 Hz, 1 H), 7.68 (s, 1 H), 7.51 (d, J=2.1 Hz, 1 H), 6.73 (s, 1 H), 6.62 (d, J=8.4 Hz, 1 H), 3.92-3.85 (m, 7 H), 3.46-3.29 (m, 12 H). MS: 452 (M+H$^+$).

EXAMPLE 22

4-(2,6-dichlorobenzyl)-6-{[4-(piperazin-1-yl)-2-(trifluoromethyl)phenyl]amino}-1H-imidazo[4,5-c]pyridine-7-carboxamide

EXAMPLE 22A tert-butyl 4-(4-amino-3-(trifluoromethyl)phenyl)piperazine-1-carboxylate The title compound was obtained following the procedure described in Example 13A and 13B, using 4-fluoro-1-nitro-2-(trifluoromethyl)benzene in place of 4-fluoro-2-methoxy-1-nitrobenzene.

EXAMPLE 22B tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-3-(trifluoromethyl)phenyl)piperazine-1-carboxylate A mixture of the product of Example 8I (140 mg, 0.3 mmol), the product of Example 22A (103 mg, 0.3 mmol), tricyclohexylphosphine (26 mg, 0.09 mmol), palladium diacetate (11 mg, 0.05 mmol) and cesium carbonate (195 mg, 0.6 mmol) in toluene (50 mL) was heated under nitrogen at 100° C. for 14 hours. After cooling to ambient temperature, the mixture was filtered and concentrated. The residue was purified by flash chromatography on silica gel (200-300 mesh) eluting with 5/1 petroleum ether/ethyl acetate to provide the title compound. MS: 776 (M+H$^+$).

EXAMPLE 22C 4-(2,6-dichlorobenzyl)-6-(4-(piperazin-1-yl)-2-(trifluoromethyl)phenylamino)-1H-imidazo[4,5-c]pyridine-7-carboxamide To a solution of the product of Example 22B (150 mg, 0.2 mmol) in concentrated sulfuric acid (5 mL) was added water (1 mL) at 0° C. and the mixture was stirred at 95° C. for 20 minutes. After cooling to ambient temperature, water (3 mL) was added. The mixture was adjusted to pH 8-9 with saturated aqueous sodium bicarbonate solution and extracted with dichloromethane (3×20 mL). The organic layers were concentrated and the residue was purified by preparative HPLC using a gradient of 10/90 to 80/20 acetonitrile/water (containing 0.1% trifluoroacetic acid) to give the title compound. $^1$H NMR (DMSO-d$_6$, 300 MHz): δ 13.51 (br, 1 H), 11.64 (s, 1 H), 9.52 (br, 1 H), 8.80 (s, 2 H), 8.61(s, 1 H), 7.81 (s, 1-H), 7.62 (d, J=9 Hz, 1 H), 7.56-7.53 (m, 2 H), 7.43-7.41 (m, 1 H), 7.07 (d, J=2.1 Hz, 1 H), 6.72 (dd, J=9, 2.1 Hz, 1 H), 4.83 (s, 2H), 2.75-2.67 (m, 8 H). MS: 564 (M+H$^+$).

EXAMPLE 23

5-(2,6-dichlorobenzyl)-7-({2-methoxy-4-[(4-methylpiperazin-1-yl)carbonyl]phenyl}amino)imidazo[1,2-c]pyrimidine-8-carboxamide The title compound was obtained following the procedure described in Example 10, using 1-methylpiperazine in place of morpholine. $^1$H NMR (DMSO-d$_6$, 300 MHz): δ 12.51 (s, 1H), 9.88 (br, 1H), 9.74 (s, 1H), 8.29 (s, 1H), 7.93 (br, 1H), 7.46-7.70 (m, 5H), 7.03 (s, 1H), 6.50 (d, J=8.1 Hz, 1H), 4.90 (s, 2H), 3.90 (s, 3H), 3.09-3.52 (m, 8H), 2.88 (s, 3H). MS: 568 (M+H$^+$):

EXAMPLE 24

5-(2,6-dichlorobenzyl)-7-[(2-methoxy-4-{[2-(4-methylpiperazin-1-yl)ethyl]carbamoyl}phenyl)amino]imidazo[1,2-c]pyrimidine-8-carboxamide The title compound was obtained following the procedure described in Example 10, using 2-(4-methylpiperazin-1-yl)ethanamine in place of morpholine. $^1$H NMR (DMSO-d$_6$, 300 MHz): δ 12.56 (s, 1H), 9.75 (s, 1H), 8.46 (br, 1H), 8.30 (s, 1H), 7.94 (br, 1H), 7.44-7.71 (m, 5H), 6.97 (d, 1H), 4.90 (s, 2H), 3.92 (s, 3H), 3.03-3.51 (m, 12H), 2.82 (s, 3H). MS: 611 (M+H$^+$).

EXAMPLE 25

5-(2,6-dichlorobenzyl)-7-{[3,5-dichloro-4-(piperazin-1-yl)phenyl]amino}[1,2,4]triazolo[4,3-c]pyrimidine-8-carboxamide

EXAMPLE 25A tert-butyl 4-(4-amino-2,6-dichlorophenyl)piperazine-1-carboxylate The title compound was obtained following the procedure described in Example 13A and B, using 2-bromo-1,3-dichloro-5-nitrobenzene in place of 4-fluoro-2-methoxy-1-nitrobenzene.

EXAMPLE 25B tert-butyl 4-(4-(5-carbamoyl-6-chloro-2-(methylthio)pyrimidin-4-ylamino)-2,6-dichlorophenyl)piperazine-1-carboxylate The title compound was obtained following the procedure described in Example 16E, using the product of Example 25A in place of the product of Example 16D. MS: 548 (M+H$^+$).

EXAMPLE 25C tert-butyl 4-(4-(5-carbamoyl-6-hydrazinyl-2-(methylthio)pyrimidin-4-ylamino)-2,6-dichlorophenyl)piperazine-1-carboxylate The title compound was obtained following the procedure described in Example 16F, using the product of Example 25B in place of the product of Example 16E. MS: 547 (M+H$^+$).

EXAMPLE 25D tert-butyl 4-(4-(8-carbamoyl-5-(methylthio)-[1,2,4]triazolo[4,3-f]pyrimidin-7-ylamino)-2,6-dichlorophenyl)piperazine-1-carboxylate The title compound was obtained following the procedure described in Example 16G, using the product of Example 25C in place of the product of Example 16F. MS: 552 (M+H$^+$).

EXAMPLE 25E tert-butyl 4-(4-(5-(2,6-dichlorobenzyl)-8-carbamoyl-[1,2,4]triazolo[4,3-f]pyrimidin-7-ylamino)-2,6-dichlorophenyl)piperazine-1-carboxylate The title compound was obtained following the procedure described in Example 16H, using the product of Example 25D in place of the product of Example 16G. MS: 666 (M+H$^+$).

EXAMPLE 25F 5-(2,6-dichlorobenzyl)-7-(3,5-dichloro-4-(piperazin-1-yl)phenylamino)-[1,2,4]triazolo[4,3-f]pyrimidine-8-carboxamide The title compound was obtained following the procedure described in Example 16I, using the product of Example 25E in place of the product of Example 16H. $^1$H NMR (DMSO-d$_6$, 300 MHz): δ 12.42 (s, 1H), 9.73 (s, 1H), 9.01 (s, 1H), 8.71 (brs, 2H), 8.22 (s, 1H), 7.57 (s, 1H), 7.55 (s, 1H), 7.41 (q, 1H), 7.28 (s, 1H), 4.96 (s, 2H), 3.22 (m, 4H), 3.15 (m, 4H). MS: 566 (M+H$^+$).

EXAMPLE 26

4-(2,6-dichlorobenzyl)-6-{[2-methyl-4-(piperazin-1-yl)phenyl]amino}-1H-imidazo[4,5-c]pyridine-7-carboxamide

EXAMPLE 26A tert-butyl 4-(4-amino-3-methylphenyl)piperazine-1-carboxylate

The title compound was obtained following the procedure described in Example 13A and B, using 4-fluoro-2-methyl-1-nitrobenzene in place of 4-fluoro-2-methoxy-1-nitrobenzene.

EXAMPLE 26B tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-3-methylphenyl)piperazine-1-carboxylate A mixture of the product of Example 8I (200 mg, 0.43 mmol), the product of Example 26A (125 mg, 0.43 mmol), tricyclohexylphosphine (36 mg, 0.13 mmol), palladium diacetate (15 mg, 0.06 mmol) and cesium carbonate (279 mg, 0.86 mmol) in toluene (50 mL) was heated under nitrogen at 100° C. for 14 hours. After cooling to ambient temperature, the mixture was filtered and concentrated. The residue was purified by flash chromatography on silica gel (200-300 mesh) eluting with 5/1 petroleum ether/ethyl acetate to provide the title compound. MS: 722 (M+H$^+$).

EXAMPLE 26C 4-(2,6-dichlorobenzyl)-6-(2-methyl-4-(piperazin-1-yl)phenylamino)-1H-imidazo[4,5-c]pyridine-7-carboxamide To a solution of the product of Example 26B (194 mg, 0.27 mmol) in concentrated sulfuric acid (5 mL) was added water (1 mL) at 0° C. and the mixture was stirred at 95° C. for 20 minutes. After cooling to ambient temperature, water (3 mL) was added. The mixture was adjusted to pH 8-9 with saturated sodium bicarbonate solution and extracted with dichloromethane (3×20 mL). The organic layers were concentrated under vacuum and the residue was purified via preparative HPLC using a gradient of 10/90 to 75/25 acetonitrile/water (containing 0.1% trifluoroacetic acid) to give the title compound. $^1$H NMR (DMSO-d$_6$, 300 MHz): δ 13.62 (br, 1 H), 11.4 (br, 1 H), 9.58 (br, 1 H), 8.66 (s, 2 H), 8.58 (s, 1 H), 7.75-7.57 (m, 3 H), 7.45 (d, J=9 Hz, 1 H), 6.78 (d, J=2.4 Hz, 1 H), 6.34 (dd, J=9, 2.4 Hz, 1 H), 4.70 (s, 2 H), 3.26-3.22 (m, 8 H), 2.23 (s, 3 H). MS: 510 (M+H$^+$).

EXAMPLE 27

7-{[3-chloro-4-(piperazin-1-yl)phenyl]amino}-5-(2,6-dichlorobenzyl)[1,2,4]triazolo[4,3-c]pyrimidine-8-carboxamide

EXAMPLE 27A tert-butyl 4-(4-(5-carbamoyl-6-chloro-2-(methylthio)pyrimidin-4-ylamino)-2-chlorophenyl)piperazine-1-carboxylate The title compound was obtained following the procedures described in Example 15A-D, using 4-bromo-3-chloroaniline in place of 4-bromo-2,5-difluoroaniline. MS: 513 (M+H$^+$).

EXAMPLE 27B tert-butyl 4-(4-(5-carbamoyl-6-hydrazinyl-2-(methylthio)pyrimidin-4-ylamino)-2-chlorophenyl)piperazine-1-carboxylate The title compound was obtained following the procedure described in Example 15E, using the product of Example 27A in place of the product of Example 15D. MS: 509 (M+H$^+$).

EXAMPLE 27C tert-buty 14-(4-(8-carbamoyl-5-(methylthio)-[1,2,4]triazolo[4,3-c]pyrimidin-7-ylamino)-2-chlorophenyl)piperazine-1-carboxylate The title compound was obtained following the procedure described in Example 15F, using the product of Example 27B in place of the product of Example 15E. MS: 519 (M+H$^+$).

EXAMPLE 27D tert-butyl 4-(4-(8-carbamoyl-5-(2,6-dichlorobenzyl)-[1,2,4]triazolo[4,3-c]pyrimidin-7-ylamino)-2-chlorophenyl)piperazine-1-carboxylate The title compound was obtained following the procedure described in Example 15G, using the product of Example 27C in place of the product of Example 15F. MS: 631 (M+H$^+$).

EXAMPLE 27E 7-(3-chloro-4-(piperazin-1-yl)phenylamino)-5-(2,6-dichlorobenzyl)-[1,2,4]triazolo[4,3-c]pyrimidine-8-carboxamide The title compound was obtained following the procedure described in Example 15H, using the product of Example 27D in place of the product of Example 15G. $^1$H NMR (DMSO-d$_6$, 300 MHz): δ 12.26 (s, 1H), 9.71 (s, 1H), 9.00 (s, 1H), 8.77 (brs, 2H), 8.15 (s, 1H), 7.62-7.60 (m, 2H), 7.48-7.43 (m, 1H), 7.37 (d, J=2.4 Hz, 1H), 7.03-7.00 (m, 1H), 6.91-6.88 (m, 1H), 4.97 (s, 2H), 3.27-3.26 (m, 4H), 3.11-3.08 (m, 4H). MS: 531 (M+H$^+$).

EXAMPLE 28

5-(2,6-dichlorobenzyl)-7-{[2-fluoro-4-(piperazin-1-yl)phenyl]amino}[1,2,4]triazolo[4,3-c]pyrimidine-8-carboxamide

EXAMPLE 28A tert-butyl 4-(3-fluoro-4-nitrophenyl)piperazine-1-carboxylate

A mixture of 4-bromo-2-fluoro-1-nitrobenzene (5 g, 23 mmol), tert-butyl piperazine-1-carboxylate (4.24 g, 23 mmol), palladium diacetate (0.51 g, 2.3 mmol), (±)-2,2'-bis(diphenylphosphino)-1,1'-binaphthalene (2.13 g, 3.4 mmol) and cesium carbonate (14.8 g, 45 mmol) in toluene (120 mL) was heated under nitrogen at 60° C. for 20 hours. After cooling to ambient temperature, the mixture was concentrated and the residue was diluted with dichloromethane (300 mL) and washed with water. The combined organic phase was washed with brine, dried over sodium sulfate, filtered and concentrated. The residue was purified by flash chromatography on silica gel (200-300 mesh) eluting with 3/1 petroleum ether/ethyl acetate to give the title compound. MS: 348 (M+Na$^+$).

EXAMPLE 28B tert-butyl 4-(4-amino-3-fluorophenyl)piperazine-1-carboxylate

A mixture of the product of Example 28A (1.6 g, 4.9 mmol), zinc dust (3.2 g, 49 mmol) and acetic acid (5.4 mL) in 1/1 tetrahydrofuran/methanol (100 mL) was stirred at ambient temperature for 1 hour. The mixture was filtered and the filtrate was diluted with water and adjusted to pH 9. The mixture was extracted with ethyl acetate and the combined organic phase was washed with brine, dried over sodium sulfate, filtered and concentrated. The residue was purified by flash chromatography on silica gel (200-300 mesh) eluting with 99/1 dichloromethane/methanol to give the title compound. MS: 296 (M+H$^+$).

EXAMPLE 28C tert-butyl 4-(4-(5-carbamoyl-6-chloro-2-(methylthio)pyrimidin-4-ylamino)-3-fluorophenyl)piperazine-1-carboxylate A mixture of the product of Example 28B (296 mg, 1 mmol), the product of Example 2D (238 mg, 1 mmol), and N,N-diisopropylethylamine (258 mg, 2 mmol) in 1,4-dioxane (10 mL) was heated in a sealed tube at 100° C. for 16 hours. The mixture was concentrated and the crude title compound was used in the next step without further purification. MS: 492 (M+H$^+$).

EXAMPLE 28D tert-butyl 4-(4-(5-carbamoyl-6-hydrazinyl-2-(methylthio)pyrimidin-4-ylamino)-3-fluorophenyl)piperazine-1-carboxylate To a solution of the product of Example 28C (497 mg, 1 mmol) in 1,4-dioxane (10 mL) was added hydrazine hydrate (0.3 mL). After stirring at ambient temperature for about 4 hours, the mixture was concentrated. The residue was washed with hexane and dried under vacuum to give the title compound, which was used in the next step without further purification. MS: 493 (M+H$^+$).

EXAMPLE 28E tert-butyl 4-(4-(8-carbamoyl-5-(methylthio)-[1,2,4]triazolo[4,3-c]pyrimidin-7-ylamino)-3-fluorophenyl)piperazine-1-carboxylate To a solution of the product of Example 28D (240 mg, 0.5 mmol) in dimethylacetamide (2 mL) was added methyl orthoformate (2 mL). The mixture was stirred at ambient temperature for 1 hour and at 60° C. for 4 hours. After cooling to ambient temperature, petroleum 9/1 ether/ethyl acetate (50 mL) was added and the precipitate was filtered. The solid was washed with petroleum ether and dried under vacuum to give the title compound. MS: 503 (M+H$^+$).

EXAMPLE 28F tert-butyl 4-(4-(8-carbamoyl-5-(2,6-dichlorobenzyl)-[1,2,4]triazolo[4,3-c]pyrimidin-7-ylamino)-3-fluorophenyl)piperazine-1-carboxylate To a mixture of the product of Example 28E (200 mg, 0.4 mmol) and tetrakis(triphenylphosphine)palladium (50 mg, 0.04 mmol) was added 0.5M 2,6-dichlorobenzylzinc bromide in tetrahydrofuran (4 mL, 2 mmol) under nitrogen atmosphere and the mixture was heated at 70° C. for 16 hours. After cooling to ambient temperature, the mixture was diluted with dichloromethane (50 mL) and washed with saturated aqueous sodium bicarbonate. The organic phase was separated and the aqueous phase was extracted with dichloromethane (2×20 mL). The combined organic phase was washed with brine, dried over sodium sulfate, filtered and concentrated. The residue was purified by flash chromatography on silica gel (200-300 mesh) eluting with 97/3 dichloromethane/methanol to give the title compound. MS: 615 (M+H$^+$).

EXAMPLE 28G 5-(2,6-dichlorobenzyl)-7-(2-fluoro-4-(piperazin-1-yl)phenylamino)-[1,2,4]triazolo[4,3-c]pyrimidine-8-carboxamide To a solution of the product of Example 28F (220 mg, 0.36 mmol) in dichloromethane (8 mL) was added trifluoroacetic acid (2 mL) dropwise and the mixture was stirred at ambient temperature for 4 hours. After concentration, the residue was washed with ethanol and dried under vacuum to give the title compound. $^1$H NMR (DMSO-$d_6$, 300 MHz): δ 12.11 (s, 1H), 9.68 (s, 1H), 8.94-8.91 (m, 3H), 8.07 (s, 1H), 7.64-7.61 (m, 2H), 7.54-7.49 (m, 1H), 7.19-7.12 (t, J=9.3 Hz, 1H), 6.87(dd, J=2.4 Hz, J=14.4 Hz, 1H), 6.29 (dd, J=9.0, 1.8 Hz, 1H), 4.96 (s, 2H), 3.27 (m, 8H). MS: 515 (M+H$^+$).

EXAMPLE 29

4-(2,6-dichlorobenzyl)-6-{[3-methyl-4-(piperazin-1-yl)phenyl]amino}-1H-imidazo[4,5-c]pyridine-7-carboxamide

EXAMPLE 29A tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-2-methylphenyl)piperazine-1-carboxylate A mixture of the product of Example 8I (140 mg, 0.3 mmol), the product of Example 17B (88 mg, 0.3 mmol), tricyclohexylphosphine (26 mg, 0.09 mmol), palladium diacetate (11 mg, 0.05 mmol) and cesium carbonate (195 mg, 0.6 mmol) in toluene (50 mL) was heated under nitrogen at 100° C. for 14 hours. After cooling to ambient temperature, the mixture was filtered and concentrated. The residue was purified by flash chromatography on silica gel (200-300 mesh) eluting with 5/1 petroleum ether/ethyl acetate to provide the title compound. MS: 722 (M+H$^+$).

EXAMPLE 29B 4-(2,6-dichlorobenzyl)-6-(3-methyl-4-(piperazin-1-yl)phenylamino)-1H-imidazo[4,5-c]pyridine-7-carboxamide To a solution of the product of Example 29A (120 mg, 0.17 mmol) in concentrated sulfuric acid (5 mL) was added water (1 mL) at 0° C. and the mixture was heated at 95° C. for 20 minutes. After cooling to ambient temperature, the mixture was diluted with water (3 mL), and the pH was adjusted to pH 8-9 with saturated sodium bicarbonate solution. The mixture was extracted with dichloromethane (3×20 mL). The combined organic phase was concentrated and the residue was purified via preparative HPLC using a gradient of 10/90 to 80/20 acetonitrile/water (containing 0.1% trifluoroacetic acid) to give the title compound. $^1$H NMR (DMSO-$d_6$, 3 00 MHz): δ 13.55 (br, 1H), 11.66 (s, 1 H), 9.58 (s, 1 H), 8.67 (s, 1 H), 8.57 (s, 1 H), 7.81 (s, 1 H), 7.57-7.54 (m, 1 H), 7.41-7.36 (m, 1 H), 7.11 (dd, J=8.4, 2.1 Hz, 1 H), 7.05 (d, J=2.1 Hz, 1 H), 6.62 (d, J=8.4 Hz, 1 H), 4.69 (s, 2H), 3.23-3.22 (m, 4 H), 2.94-2.92 (m, 4 H), 2.14 (s, 3 H). MS: 510 (M+H$^+$).

EXAMPLE 30

4-(2,6-dichlorobenzyl)-6-({2-methoxy-4-[2-oxo-2-(pyrrolidin-1-yl)ethyl]phenyl}amino)-1H-imidazo[4,5-c]pyridine-7-carboxamide

EXAMPLE 30A diethyl 2-(3-methoxy-4-nitrophenyl)malonate

To a suspension of NaH (151 g, 88 mmol) in dry N,N-dimethylformamide (40 mL) at 0° C. was added diethyl malonate (10.3 g, 64.3 mmol) and the mixture was stirred at room temperature for 30 minutes. A solution of 4-fluoro-2-methoxy-1-nitrobenzene (10 g, 58.5 mmol) was added and the mixture was stirred at 90° C. overnight. The mixture was diluted with water and extracted with ethyl acetate (3×20 mL). The combined organic phase was washed with brine, dried over anhydrous sodium sulfate, filtered and concentrated. The residue was purified by flash chromatography on silica gel eluting with a gradient of 1/20 to 1/10 ethyl acetate/petroleum ether to afford the title compound.

EXAMPLE 30B 2-(3-methoxy-4-nitrophenyl)acetic acid

To a solution of the product of EXAMPLE 30A (0.3 g, 0.96 mmol) in ethanol (2 mL) was added 2N aqueous sodium hydroxide (2 mL) and the mixture was stirred at room temperature for 12 hours. Ater concentration, the residue was diluted with water and extracted with ethyl acetate. The aqueous phase was acidified to pH 2-3 with concentrated HCl and extracted with ethyl acetate (3×5 mL). The combined organic phase was washed with brine, dried over anhydrous sodium sulfate, filtered and concentrated. The title compound was used in the next step without further purification.

EXAMPLE 30C 2-(3-methoxy-4-nitrophenyl)-1-(pyrrolidin-1-yl)ethanone

A solution of the product of EXAMPLE 30B (1 g, 4.74 mmol) in thionyl dichloride (20 mL) was stirred at reflux for 3 hours. The solution was concentrated and the residue was diluted with dry dichloromethane (20 mL) and dropped into a solution of pyrrolidine (0.63 mL, 7.1 mmol) and diisopropyl ethylamine (1.7 mL, 9.5 mmol). The mixture was stirred at room temperature overnight and the mixture was washed with 1N aqueous hydrochloric acid (20 mL) and brine. The organic phase was dried over anhydrous sodium sulfate, filtered and concentrated and the residue was purified by flash chromatography on silica gel eluting with 1/100 methanol/dichloromethane to give the title compound.

EXAMPLE 30D 2-(4-amino-3-methoxyphenyl)-1-(pyrrolidin-1-yl)ethanone

To a suspension of Raney Ni (0.5 g) in methanol (10 mL) was added EXAMPLE 30C (0.9 g, 3.4 mmol) and the mixture was degassed with hydrogen three times and stirred at room temperature under hydrogen overnight. The mixture was filtered through a pad of diatomaceous earth, washed with methanol and concentrated to give the title compound.

EXAMPLE 30E 4-(2,6-dichlorobenzyl)-6-((2-methoxy-4-(2-oxo-2-(pyrrolidin-1-yl)ethyl)phenyl)amino)-1-((2-(trimethylsilyl)ethoxy)methyl)-1H-imidazo[4,5-c]pyridine-7-carbonitrile A mixture of the product of Example 8I (259 mg, 0.56 mmol), the product of Example 30D (260 mg, 1.11 mmol), palladium acetate (13 mg, 0.06 mmol), tricyclohexylphosphine (31 mg, 0.11 mmol), cesium carbonate (0.361 g, 1.11 mmol) and toluene (3 mL) was degassed with nitrogen 6 times and heated at 110° C. for 15 hours. After cooling to ambient temperature, the mixture was concentrated and purified by flash chromatography on silica gel (200-300 mesh) eluting with 60/1 dichloromethane/methanol to give the title compound. MS: 665 (M+H$^+$).

EXAMPLE 30F 4-(2,6-dichlorobenzyl)-6-((2-methoxy-4-(2-oxo-2-(pyrrolidin-1-yl)ethyl)phenyl)amino)-1H-imidazo[4,5-c]pyridine-7-carboxamide The product of Example 30E (80 mg, 0.12 mmol) was dissolved in concentrated sulfuric acid (3 mL) and water (0.5 mL) was added and the solution was heated at 85° C. for 0.5 hours. After cooling to ambient temperature, the mixture was neutralized with saturated aqueous sodium bicarbonate solution and extracted with dichloromethane. The organic phase was dried over anhydrous sodium sulfate, filtered, concentrated and purified by preparative HPLC using a gradient of 10/90 to 75/25 acetonitrile/water (containing 0.1% trifluoroacetic acid) to give the title compound. $^1$H NMR (DMSO-d$_6$, 300 MHz): δ 14.11 (s, 1 H), 11.83 (s, 1 H), 9.59 (s, 1 H), 8.59 (s, 1 H), 7.71-7.68 (m, 2 H), 7.60-7.58 (m, 2 H), 7.44 (t, J=7.8 Hz, 1 H), 6.77 (s, 1 H), 6.31 (d, J=8.1 Hz, 1 H), 4.79 (s, 2 H), 3.81 (s, 3 H), 3.51 (s, 2 H), 3.46 (t, J=6.6 Hz, 2 H), 3.33 (t, J=6.3 Hz, 2 H), 1.93-1.78 (m, 4 H). MS: 553 (M+H$^+$).

EXAMPLE 31

4-(2,6-dichlorobenzyl)-6-[(4-{[2-(dimethylamino)ethyl]carbamoyl}-2-methoxyphenyl)amino]-1H-imidazo[4,5-c]pyridine-7-carboxamide

EXAMPLE 31A

N-(2-(dimethylamino)ethyl)-3-methoxy-4-nitrobenzamide

To a solution of 3-methoxy-4-nitrobenzoic acid (5.0 g, 25.4 mmol) and N$^1$,N$^1$-dimethylethane-1,2-diamine (2.7 g, 30.5 mmol) in dichloromethane (200 mL) were added 1-hydroxybenzotriazole hydrate (7.8 g, 50.8 mmol), 1-ethyl-(3-dimethyl aminopropyl)carbodiimide hydrochloride (9.7 g, 50.8 mmol) and N,N-diisopropyl ethylamine (13.1 g, 101.6 mmol) and the mixture was stirred at ambient temperature for 16 hours. The mixture was washed with water (50 mL), dried over sodium sulfate, filtered, and concentrated. The residue was purified by flash chromatography on silica gel (200-300 mesh) eluting with 20/1 dichloromethane/methanol to give the title compound. MS: 268 (M+H$^+$).

EXAMPLE 31B 4-amino-N-(2-(dimethylamino)ethyl)-3-methoxy-benzamide

To a suspension of the product of Example 31A (5.4 g, 20.2 mmol) in methanol (200 mL) was added 10% palladium on carbon (540 mg) and the mixture was stirred under hydrogen for 4 hours. The catalyst was filtered off and the filtrate was concentrated to give the title compound. MS: 238 (M+H$^+$).

EXAMPLE 31C 4-(7-cyano-4-(2,6-dichlorobenzyl)-1-((2-(trimethylsilyl)ethoxy)methyl)-1H-imidazo[4,5-c]pyridin-6-ylamino)-N-(2-(dimethylamino)ethyl)-3-methoxy-benzamide A suspension of the product of Example 8I (170 mg, 0.5 mmol), the product of Example 31B (120 mg, 0.5 mmol), tricyclohexylphosphine (42 mg, 0.15 mmol), palladium diacetate (17 mg, 0.075 mmol) and cesium carbonate (326 mg, 1 mmol) in 1,4-dioxane (15 mL) was stirred under nitrogen for 17 hours at 100° C. The mixture was concentrated and purified by flash chromatography on silica gel eluting with 10:1 dichloromethane/methanol to give the title compound. MS: 668 (M+H$^+$).

EXAMPLE 31D 4-(2,6-dichlorobenzyl)-6-(4-(2-(dimethylamino)ethylcarbamoyl)-2-methoxyphenylamino)-1H-imidazo[4,5-c]pyridine-7-carboxamide A solution of the product of Example 31C (60 mg, 0.1 mmol) in concentrated sulfuric acid (3 mL) and water (0.5 mL) was stirred for 10 minutes at 0° C. and at 90° C. for 1.5 hours. The mixture was quenched with crushed ice and adjusted pH 9 with sodium bicarbonate solution. The precipitate was filtered off and the filtrate was extracted with 4/1 dichloromethane/methane (5×50 mL). The organic layers were collected, concentrated and purified by preparative HPLC using a gradient of 10/90 to 80/20 acetonitrile/water (containing 0.1% trifluoroacetic acid) to give the title compound. $^1$H NMR (DMSO-d$_6$, 300 MHz): δ 12.2 (s, 1H), 9.59 (s, 1H), 9.38 (s, 1H), 8.58-8.62 (d, J=12 Hz, 2H), 7.88-7.92 (m, 2H), 7.59-7.62 (m, 2H), 7.39-7.47 (m, 2H), 7.06 (m, 2H), 4.75 (s, 2H), 3.89 (s, 3H), 3.58-3.60 (d, J=6 Hz, 2H), 3.25-3.27 (d, J=6 Hz, 2H), 3.88 (s, 6H). MS: 556 (M+H$^+$).

EXAMPLE 32

5-(2,6-dichlorobenzyl)-7-[(2-methoxy-4-{[2-(pyrrolidin-1-yl)ethyl]carbamoyl}phenyl)amino]imidazo[1,2-c]pyrimidine-8-carboxamide The title compound was obtained following the procedure described in Example 10F, using 2-(pyrrolidin-1-yl)ethanamine in place of morpholine. $^1$H NMR (DMSO-d$_6$, 300 MHz): δ 12.56 (s, 1H), 9.74 (s, 1H), 9.48 (br, 1H), 8.57 (m, 1H), 8.28 (s, 1H), 7.92 (d, 1H), 7.44-7.68 (m, 6H), 6.97 (d, J=8.4 Hz, 1H), 4.88 (s, 2H), 3.91 (s, 3H), 3.58-3.65 (m, 4H), 3.34 (m, 2H), 3.06 (m, 2H), 1.86-2.04 (m, 4H). MS: 582 (M+H$^+$).

EXAMPLE 33

5-(2,6-dichlorobenzyl)-7-[(2-methoxy-4-{[2-(piperidin-1-yl)ethyl]carbamoyl}phenyl)amino]imidazo[1,2-c]pyrimidine-8-carboxamide The title compound was obtained following the procedure described in Example 10F, using 2-(piperidin-1-yl)ethanamine in place of morpholine. $^1$H NMR (DMSO-$d_6$, 300 MHz): δ 12.56 (s, 1H), 9.74 (s, 1H), 9.09 (br, 1H), 8.58 (m, 1H), 8.28 (s, 1H), 7.91 (s, 1H), 7.42-7.68 (m, 6H), 6.97 (d, J=8.4 Hz, 1H), 4.88 (s, 2H), 3.90 (s, 3H), 3.56-3.63 (m, 4H), 3.23 (m, 2H), 2.95 (m, 3H), 1.64-1.88 (m, 5H), 1.24 (m, 1H). MS: 596 (M+H$^+$).

EXAMPLE 34

5-(2,6-dichlorobenzyl)-7-[(4-{[4-(dimethylamino)butyl]carbamoyl}-2-methoxyphenyl)amino]imidazo[1,2-c]pyrimidine-8-carboxamide The title compound was obtained following the procedure described in Example 10F, using N$^1$,N$^1$-dimethylbutane-1,4-diamine in place of morpholine. $^1$H NMR (DMSO-$d_6$, 300 MHz): δ 12.55 (b, 1H), 9.76 (s, 1H), 9.33 (br, 1H), 8.38 (m, 1H), 8.27 (s, 1H), 7.90 (s, 1H), 7.41-7.68 (m, 6H), 6.94 (d, J=8.7 Hz, 1H), 4.87 (s, 2H), 3.89 (s, 3H), 3.32 (m, 2H), 3.10 (m, 2H), 2.79 (s, 3H), 2.77 (s, 3H), 1.63 (m, 4H). MS: 584 (M+H$^+$).

EXAMPLE 35

5-(2,6-dichlorobenzyl)-7-[(2-methoxy-4-{[3-(morpholin-4-yl)propyl]carbamoyl}phenyl)amino]imidazo[1,2-c]pyrimidine-8-carboxamide The title compound was obtained following the procedure described in Example 10F, using 3-morpholinopropan-1-amine in place of morpholine. $^1$H NMR (DMSO-$d_6$, 300 MHz): δ 12.51 (s, 1H), 9.73 (s, 1H), 8.32 (m, 1H), 8.26 (m, 1H), 7.89 (br, 1H), 7.40-7.68 (m, 6H), 6.92 (d, J=8.7 Hz, 1H), 4.87 (s, 2H), 3.89 (s, 3H), 3.58 (m, 4H), 3.31 (m, 4H), 2.35 (m, 4H), 1.69 (m, 2H). MS: 612 (M+H$^+$).

EXAMPLE 36

5-(2,6-dichlorobenzyl)-7-{[2-methoxy-4-(piperazin-1-ylcarbonyl)phenyl]amino}imidazo[1,2-c]pyrimidine-8-carboxamide

EXAMPLE 36A tert-butyl 4-(4-(8-carbamoyl-5-(2,6-dichlorobenzyl)imidazo[1,2-f]pyrimidin-7-ylamino)-3-methoxybenzoyl)piperazine-1-carboxylate The title compound was obtained following the procedure described in Example 10F, using tert-butyl piperazine-1-carboxylate in place of morpholine. MS: 654 (M+H$^+$).

EXAMPLE 36B 5-(2,6-dichlorobenzyl)-7-(2-methoxy-4-(piperazine-1-carbonyl)phenylamino)imidazo[1,2-f]pyrimidine-8-carboxamide To a solution of the product of Example 36A (100 mg, 0.15 mmol) in dichloromethane (25 mL) was added trifluoroacetic acid (5 mL), and the mixture was stirred at ambient temperature for 2 hours. After concentration, the residue was purified by preparative HPLC using a gradient of 10/90 to 75/25 acetonitrile/water (containing 0.1% trifluoroacetic acid) to give the title compound. $^1$H NMR (DMSO-$d_6$, 300 MHz): δ 12.50 (s, 1H), 9.75 (s, 1H), 8.92 (br, 2H), 8.29 (d, J=1.8 Hz, 1H), 7.92 (s, 1H), 7.69 (m, 3H), 7.55 (m, 1H), 7.46 (d, J=8.4 Hz, 1H), 7.05 (d, J=1.8 Hz, 1H), 6.50 (d, J=8.4 Hz, 1H), 4.90 (s, 2H), 3.90 (s, 3H), 3.69 (m, 4H), 3.22 (m, 4H). MS: 554 (M+H$^+$).

EXAMPLE 37

4-(2,6-dichlorobenzyl)-6-({2-methoxy-4-[(4-methylpiperazin-1-yl)carbonyl]phenyl}amino)-1H-imidazo[4,5-c]pyridine-7-carboxamide

EXAMPLE 37A (3-methoxy-4-nitrophenyl)(4-methylpiperazin-1-yl)methanone

A solution of 3-methoxy-4-nitrobenzoic acid (6.81 g, 34.54 mmol) in sulfurous dichloride (50 mL) was stirred at reflux for 8 hours. After cooling to ambient temperature, the mixture was concentrated under vacuum and the residue was dissolved in dichloromethane (60 mL). 1-Methylpiperazine (3.6 g, 36.27 mmol) was added at 0° C. and the mixture was stirred at ambient temperature for 4 hours. The mixture was poured into water (100 mL) and extracted with dichloromethane (2×200 mL). The organic phase was dried over anhydrous sodium sulfate, filtered and concentrated to provide the crude title compound. MS: 280.2 (M+H$^+$).

EXAMPLE 37B (4-amino-3-methoxyphenyl)(4-methylpiperazin-1-yl)methanone

To a solution of Example 37A (9 g, 32 mmol) in methanol (100 mL) was added 10% palladium on carbon (1 g) and the mixture was stirred at ambient temperature under hydrogen for 8 hours. The mixture was filtered and the filtrate was concentrated to provide the title compound. MS: 250.2 (M+H$^+$).

EXAMPLE 37C 4-(2,6-dichlorobenzyl)-6-(2-methoxy-4-(1-methylpiperazine-4-carbonyl)phenylamino)-1-((2-(trimethylsilyl)ethoxy)methyl)-1H-imidazo[4,5-c]pyridine-7-carbonitrile The title compound was obtained following the procedure described in Example 8J, using the product of Example 37B in place of tert-butyl 4-(4-amino-3-methoxyphenyl)piperazine-1-carboxylate. MS: 680 (M+H$^+$).

EXAMPLE 37D 4-(2,6-dichlorobenzyl)-6-(2-methoxy-4-(1-methylpiperazine-4-carbonyl)phenylamino)-1H-imidazo[4,5-c]pyridine-7-carboxamide The title compound was obtained as a trifluoroacetate salt following the procedure described in Example 8K, using the product of Example 37C in place of the product of Example 8J. ¹H NMR (CD₃OD, 300 MHz): δ 8.42 (s, 1H), 8.01 (d, J=8.1 Hz, 1H), 7.56 (d, J=7.5 Hz, 2H), 7.42 (dd, J=7.5, 8.7 Hz, 1H), 7.04 (d, J=1.8 Hz, 1H), 6.67 (dd, J=1.8, 8.4 Hz, 1H), 4.84 (s, 2H), 4.52 (brs, 2H), 3.99 (s, 3H), 3.58 (brs, 4H), 3.25 (brs, 2H), 3.01. (s, 3H). MS: 568 (M+H⁺).

EXAMPLE 38

4-(2,6-dichlorobenzyl)-6-{[2-fluoro-4-(piperazin-1-yl)phenyl]amino}-1H-imidazo[4,5-c]pyridine-7-carboxamide

EXAMPLE 38A tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-3-fluorophenyl)piperazine-1-carboxylate The title compound was obtained following the procedure described in Example 8J, using the product of Example 28B in place of tert-butyl 4-(4-amino-3-methoxyphenyl)piperazine-1-carboxylate. MS: 726 (M+H⁺).

EXAMPLE 38B 4-(2,6-dichlorobenzyl)-6-(2-fluoro-4-(piperazin-1-yl)phenylamino)-1H-imidazo[4,5-c]pyridine-7-carboxamide The title compound was obtained as a trifluoroacetate salt following the procedure described in Example 8K, using the product of Example 38A in place of the product of Example 8J. ¹H NMR (DMSO-d₆, 300 MHz): δ 13.62 (s, 1H), 11.72 (s, 1H), 9.56 (s, 1H), 8.69 (s, 1H), 7.81 (s, 1H), 7.60-7.69 (m, 3H), 7.44-7.49 (m, 1H), 6.84-6.90 (d, J=18 Hz, 1H), 6.25-6.27 (d, J=6 Hz, 1H), 4.73 (s, 2H), 3.47 (s, 8H). MS: 514 (M+H⁺).

EXAMPLE 39

4-(2,6-dichlorobenzyl)-6-{[2-methoxy-4-(piperazin-1-ylcarbonyl)phenyl]amino}-1H-imidazo[4,5-c]pyridine-7-carboxamide

EXAMPLE 39A 3-methoxy-4-nitrobenzoyl chloride

To a solution of 3-methoxy-4-nitrobenzoic acid (5.7 g, 30 mmol) in dichloromethane (100 mL) and N,N-dimethylformamide (5 mL) at 0° C. was added slowly oxalyl chloride (5.08 mL, 60 mmol). After stirring for 2 hours, the mixture was concentrated and the residue was used without further purification.

EXAMPLE 39B tert-butyl 4-(3-methoxy-4-nitrobenzoyl)piperazine-1-carboxylate

To a solution of the product of Example 39A (13 mmol) in dichloromethane (100 mL) at 0° C. was added slowly tert-butyl piperazine-1-carboxylate (1.06 g, 13 mmol) and triethylamine (3.6 mL). After stirring for 2 hours, water was added slowly and the mixture was extracted with dichloromethane (3×200 mL). The combined organic phase was washed with brine, dried over sodium sulfate, filtered, concentrated and purified by flash chromatography on silica gel (200-300 mesh) eluting with 100/1 dichloromethane/methanol to provide the title compound. MS: 388 (M+H⁺).

EXAMPLE 39C tert-butyl 4-(4-amino-3-methoxybenzoyl)piperazine-1-carboxylate

To a solution of the product of Example 39B (3 g, 11 mmol) in methanol (100 mL) was added Raney Ni (300 mg) and the mixture was stirred under hydrogen for 14 hours. The catalyst was filtered off and the filtrate was concentrated and purified by flash chromatography on silica gel (200-300 mesh) eluting with 100/1 dichloromethane/methanol to provide the title compound. MS: 336 (M+H⁺).

EXAMPLE 39D tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-3-methoxybenzoyl)piperazine-1-carboxylate A mixture of the product of Example 8I (180 mg, 0.38 mmol), the product of Example 39C (128 mg, 0.38 mmol), tricyclohexylphosphine (64 mg, 0.23 mmol), palladium diacetate (26 mg, 0.12 mmol) and cesium carbonate (247 mg, 0.76 mmol) in toluene (50 mL) was heated under nitrogen at 100° C. for 14 hours. After cooling, the mixture was filtered and concentrated. The residue was purified by flash chromatography on silica gel (200-300 mesh) eluting with 5/1 petroleum ether/ethyl acetate to provide the title compound. MS: 766 (M+H⁺).

EXAMPLE 39E 4-(2,6-dichlorobenzyl)-6-(2-methoxy-4-(piperazine-1-carbonyl)phenylamino)-1H-imidazo[4,5-c]pyridine-7-carbonitrile To a solution of the product of Example 39D (100 mg, 0.13 mmol) in concentrated sulfuric acid (5 mL) at 0° C. was added water (1 mL) and the mixture was heated at 95° C. for 20 minutes. After cooling, the mixture was diluted with water (3 mL), adjusted to pH 8-9 with saturated sodium bicarbonate solution and extracted with dichloromethane (3×20 mL). The combined organic phase was concentrated and the residue was purified via preparative HPLC using a gradient of 10/90 to 75/25 acetonitrile/water (containing 0.1% trifluoroacetic acid) to give the title compound. ¹H NMR (DMSO-d₆, 300 MHz): δ 12.18 (s, 1 H), 9.60 (br, 1 H), 8.86 (s, 2 H), 8.64 (s, 1 H), 7.79-7.78 (m, 1 H), 7.77 (s, 1H), 7.72 (s, 1 H), 7.64-7.61 (m, 2 H), 7.48 (d, J=9 Hz, 1 H), 6.98 (s, 1 H), 6.57 (d, J=9 Hz, 1 H), 4.90 (s, 2 H), 3.88 (s, 3 H), 3.23-3.10 (m, 8 H). MS: 554 (M+H⁺).

EXAMPLE 40

4-(2,6-dichlorobenzyl)-6-{[3,5-dichloro-4-(piperazin-1-yl)phenyl]amino}-1H-imidazo[4,5-c]pyridine-7-carboxamide

EXAMPLE 40A 6-(3,5-dichloro-4-(piperazin-1-yl)phenylamino)-4-(2,6-dichlorobenzyl)-1-((2-(trimethylsilyl)ethoxy)methyl)-1H-imidazo[4,5-c]pyridine-7-carbonitrile A suspension of the product of Example 8I (120 mg, 0.25), the product of Example 25A (97 mg, 0.28 mmol), palladium diacetate (11 mg, 0.05 mmol), (±)-2,2'-bis(diphenylphosphino)-1,1'-binaphthalene (62 mg, 0.1 mmol) and cesium carbonate (163 mg, 0.5 mmol) in 1,4-dioxane (20 mL) was stirred under nitrogen at 100° C. for 17 hours. The mixture was concentrated and purified by flash chromatography on silica gel eluting with 5/1 petroleum ether/ethyl acetate to give the title compound. MS: 676 (M+H$^+$).

EXAMPLE 40B 6-(3,5-dichloro-4-(piperazin-1-yl)phenylamino)-4-(2,6-dichlorobenzyl)-1H-imidazo[4,5-c]pyridine-7-carboxamide The title compound was obtained following the procedure described in Example 8K using the product of Example 40A in place of the product of Example 8J. $^1$H NMR (DMSO-d$_6$, 300 MHz): δ 13.74 (s, 1H), 12.17 (s, 1H), 9.68 (s, 1H), 8.69 (s, 2H), 8.04 (s, 1H), 7.55-7.58 (m, 2H), 7.36-7.46 (m, 3H), 4.76 (s, 1H), 3.19-3.28 (d, J=27 Hz, 8H). MS: 564 (M+H$^+$).

EXAMPLE 41

4-(2,6-dichlorobenzyl)-6-{[3,5-difluoro-4-(piperazin-1-yl)phenyl]amino}-1H-imidazo[4,5-c]pyridine-7-carboxamide

EXAMPLE 41A tert-butyl 4-(4-amino-2,6-difluorophenyl)piperazine-1-carboxylate The title compound was obtained following the procedure described in Example 13A and B using 1,2,3-trifluoro-5-nitrobenzene in place of 4-fluoro-2-methoxy-1-nitrobenzene.

EXAMPLE 41B tert-butyl 4-(4-(7-cyano-4-(2,6-dichlorobenzyl)-1H-(2-(trimethylsilyl)ethoxy)methyl)-1H-imidazo[4,5-c]pyridin-6-ylamino)-2,6-difluorophenyl)piperazine-1-carboxylate A suspension of the product of 81 (120 mg, 0.26 mmol), the product of Example 41A (97 mg, 0.31 mmol), palladium(II) acetate (12 mg, 0.05 mmol), tricyclohexylphosphine (29 mg, 0.10 mmol) and cesium carbonate (170 mg, 0.52 mmol) in toluene (20 mL) was heated under nitrogen at 110° C. for 16 hours. After concentration, the residue was purified by flash chromatography on silica gel (200-300 mesh) eluting with 1/1 petroleum ether/ethyl acetate to give the title compound. MS: 744 (M+H$^+$).

EXAMPLE 41C 4-(2,6-dichlorobenzyl)-6-(3,5-difluoro-4-(piperazin-1-yl)phenylamino)-1H-imidazo[4,5-c]pyridine-7-carboxamide To the product of Example 41B (190 mg, 0.26 mol) at 0° C. was added concentrated sulfuric acid (3 mL) and water (0.6 mL) and the mixture was stirred for 30 minutes at 0° C. and at 90° C. for 20 minutes. After cooling to ambient temperature, ice (10 g) was added and the mixture was extracted with 5/1 dichloromethane/methanol. The organic phase was dried over sodium sulfate, filtered, concentrated and purified by preparative HPLC using a gradient of 20/80 to 40/60 acetonitrile in water (containing 0.1% trifluoroacetic acid) to give the title compound. $^1$H NMR (DMSO-d$_6$, 300 MHz): δ 13.75 (s, 1H), 12.08 (s, 1H), 9.65 (s, 1H), 8.72 (br, 1H), 8.68 (s, 1H), 7.99 (br, 2H), 7.38-7.57 (m, 3H), 7.05 (d, 2H), 4.77 (s, 2H), 2.76 (m, 8H). MS: 532 (M+H$^+$).

EXAMPLE 42

6-{[2-chloro-4-(piperazin-1-yl)phenyl]amino}-4-(2,6-dichlorobenzyl)-1H-imidazo[4,5-c]pyridine-7-carboxamide

EXAMPLE 42A

N,N-bis(tert-butoxycarbonyl)-4-bromo-2-chloroaniline

A mixture of 4-bromo-2-chloroaniline (10 g, 48.4 mmol), di-tert-butyl dicarbonate (12.68 g, 58.12 mmol) and potassium carbonate (20.07 g, 145 mmol) in dimethylacetamide (300 mL) was stirred at ambient temperature for 24 hours. The mixture was poured into water and extracted with ethyl acetate (3×100 mL). The combined organic layer was dried over sodium sulfate, filtered, and concentrated and the residue was purified by flash chromatography on silica gel (200-300 mesh) eluting with 10/1 petroleum ether/ethyl acetate to give the title compound. MS: 428 (M+Na$^+$).

EXAMPLE 42B tert-butyl 4-(4-(bis(tert-butoxycarbonyl)amino)-3-chlorophenyl)piperazine-1-carboxylate A mixture of the product of EXAMPLE 42A (280 g, 0.9 mmol), tert-butyl piperazine-1-carboxylate (205 mg, 1.09 mmol), palladium acetate (21 mg, 0.092 mmol), (±)-2,2'-bis(diphenylphosphino)-1,1'-binaphthalene (86 mg, 0.14 mmol) and cesium carbonate (900 mg, 2.76 mmol) in toluene (10 mL) under nitrogen was heated at 100° C. for 16 hours. After cooling to ambient temperature, the mixture was concentrated and the residue was diluted with dichloromethane (300 mL), washed with water and brine, dried over sodium sulfate, filtered and concentrated. The residue was purified by flash chromatography on silica gel (200-300 mesh) eluting with 5/1 petroleum ether/ethyl acetate to give the title compound.

EXAMPLE 42C 2-chloro-4-(piperazin-1-yl)aniline

To a solution of the product of EXAMPLE 42B (320 mg, 0.63 mmol) in dichloromethane (4 mL) was added trifluoroacetic acid (1 mL) dropwise and the mixture was stirred at ambient temperature for 4 hours. The solvent was removed and the crude title compound was used in the next step without further purification. MS: 212 (M+H$^+$).

EXAMPLE 42D tert-butyl 4-(4-amino-3-chlorophenyl)piperazine-1-carboxylate

A mixture of the product of EXAMPLE 42C (133 mg, 0.63 mmol), di-tert-butyl dicarbonate (173 mg, 0.79 mmol) and potassium carbonate (546 mg, 3.95 mmol) in dimethylacetamide (5 mL) was stirred at ambient temperature for 1 hour. The mixture was poured into water and extracted with ethyl acetate (3×50 mL). The combined organic layer was dried over sodium sulfate, filtered, and concentrated and the residue was purified by flash chromatography on silica gel (200-300 mesh) eluting with 3/1 petroleum ether/ethyl acetate to give the title compound. MS: 312 (M+H$^+$).

EXAMPLE 42E tert-butyl 4-(3-chloro-4-(7-cyano-4-(2,6-dichlorobenzyl)-1-((2-(trimethylsilyl)ethoxy)methyl)-1H-imidazo[4,5-c]pyridin-6-ylamino)phenyl)piperazine-1-carboxylate A mixture of the product of Example 8I (509 mg, 1.09 mmol), the product of Example 42D (340 mg, 1.09 mmol), palladium diacetate (37 mg, 0.16 mmol), tricyclohexylphosphine (92 mg, 0.33 mmol) and cesium carbonate (711 mg, 2.18 mmol) in toluene (10 mL) was heated under nitrogen at 100° C. for 18 hours. After cooling to ambient temperature, the solid was filtered off and the filtrate was concentrated under vacuum. The residue was purified by flash chromatography on silica gel (200-300 mesh) eluting with 98/2 dichloromethane/methanol to give the title compound. MS: 742 (M+H$^+$).

EXAMPLE 42F 6-(2-chloro-4-(piperazin-1-yl)phenylamino)-4-(2,6-dichlorobenzyl)-1H-imidazo[4,5-c]pyridine-7-carboxamide To the product of Example 42E (200 mg, 0.27 mmol) in concentrated sulfuric acid (4 mL) at 0° C. was added water (0.4 mL) and the mixture was stirred at 0° C. for 10 minutes and at 80° C. for 40 minutes. After cooling to ambient temperature, the mixture was poured into ice-water, adjusted to pH 9 by saturated aqueous sodium carbonate and extracted with dichloromethane. The organic phase was washed with brine, dried over sodium sulfate, filtered and concentrated. The residue was purified by preparative HPLC using a gradient of 10/90 to 80/20 acetonitrile/water (containing 0.1% trifluoroacetic acid) to give the title compound. $^1$H NMR (DMSO-d$_6$, 300 MHz): δ 13.66 (s, 1H), 11.86 (s, 1H), 9.58 (s, 1H), 8.76 (brs, 2H), 8.63 (s, 1H), 7.83-7.78 (m, 2H), 7.61 (d, J=8.1 Hz, 2H), 7.49-7.43 (m, 2H), 7.01 (d, J=2.4 Hz, 1H), 6.43 (dd, J=9.0, 2.4 Hz, 1H), 4.73 (s, 2H), 3.27 (s, 8H). MS: 530 (M+H$^+$).

EXAMPLE 43

4-(2,6-dichlorobenzyl)-6-{[3-fluoro-2-methoxy-4-(piperazin-1-yl)phenyl]amino}-1H-imidazo[4,5-c] pyridine-7-carboxamide

EXAMPLE 43A 3-fluoro-2-methoxy-4-(piperazin-1-yl)aniline

The title compound was obtained following the procedure described in Example 13A and B using 1,2-difluoro-3-methoxy-4-nitrobenzene in place of 4-fluoro-2-methoxy-1-nitrobenzene.

EXAMPLE 43B tert-butyl 4-(4-(4-(2,6-dichlorobenzyl)-7-cyano-1-((2-(trimethylsilyl)ethoxy)methyl)-1H-imidazo[4,5-c]pyridin-6-ylamino)-2-fluoro-3-methoxyphenyl) piperazine-1-carboxylate A mixture of the product of Example 8I (144 mg, 0.308 mmol), the product of Example 43A (100 mg, 0.308 mmol), palladium diacetate (10 mg, 0.046 mmol), tricyclohexylphosphine (26 mg, 0.092 mmol) and cesium carbonate (200 mg, 0.616 mmol) in toluene (10 mL) was degassed and heated at 100° C. for 15 hours. After cooling to ambient temperature, the mixture was concentrated and the residue was purified by flash silica gel chromatography (200-300 mesh) eluting with 4/1 petroleum/ethyl acetate to give the title compound. MS: 738 (M+H$^+$).

EXAMPLE 43C 4-(2,6-dichlorobenzyl)-6-(3-fluoro-2-methoxy-4-(piperazin-1-yl)phenylamino)-1H-imidazo[4,5-c] pyridine-7-carboxamide A mixture of the product of Example 43B (50 mg, 0.068 mmol) and 4 drops of water in sulfuric acid (1 mL) was heated at 90° C. for 40 minutes. The mixture was poured onto ice water, neutralized with saturated sodium bicarbonate solution and extracted with ethyl acetate. The organic phase was dried over sodium sulfate, filtered and concentrated. The residue was purified by preparative HPLC using a gradient of 10/90 to 75/25 acetonitrile/water (containing 0.1% trifluoroacetic acid) to provide the title compound. $^1$H NMR (DMSO-d$_6$, 300 MHz): δ 8.37 (s, 1H), 7.63(dd, J=2.1 Hz, J=9.3 Hz, 1H), 7.56 (s, 1H), 7.53 (s, 1H), 7.41 (m, 1H), 6.32 (t, J=9 Hz, 1H), 4.81 (s, 2H), 3.94 (s, 3H), 3.40 (m, 4H), 3.26 (m, 4H). MS: 544 (M+H$^+$).

EXAMPLE 44

4-(2,6-dichlorobenzyl)-6-{[4-(piperazin-1-yl)-3-(trifluoromethyl)phenyl]amino}-1H-imidazo[4,5-c] pyridine-7-carboxamide

EXAMPLE 44A tert-butyl 4-(4-nitro-2-(trifluoromethyl)phenyl)piperazine-1-carboxylate A suspension of 1-fluoro-4-nitro-2-(trifluoromethyl)benzene (1 g, 4.8 mmol), tent-butyl piperazine-1-carboxylate (986 mg, 5.3 mmol) and potassium carbonate (1.3 g, 9.6 mmol) in acetonitrile (50 mL) was heated at 80° C. for 16 hours. After concentration, the residue was diluted with dichloromethane (100 mL) and washed with water (30 mL). The organic layer was dried over anhydrous sodium sulfate, filtered, and concentrated. The residue was purified by flash chromatography on silica gel (200-300 mesh) eluting with 10/1 petroleum ether/ethyl acetate to give the title compound. MS: 376 (M+H$^+$).

EXAMPLE 44B tert-butyl 4-(4-amino-2-(trifluoromethyl)phenyl) piperazine-1-carboxylate To a solution of the product of Example 44A (1 g, 2.7 mmol) in methanol (30 mL) was added Raney Nickel (100 mg) and the mixture stirred under nitrogen for 16 hours. The catalyst was filtered off and the solvent concentrated to give the title compound which was used in the next reaction without further purification. MS: 346 (M+H$^+$).

EXAMPLE 44C tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-2-(trifluoromethyl)phenyl)piperazine-1-carboxylate A suspension of the product of Example 8I (120 mg, 0.26 mmol), the product of Example 44B (107 mg, 0.31 mmol), palladium(II) acetate (12 mg, 0.05 mmol), tricyclohexylphosphine (29 mg, 0.10 mmol) and cesium carbonate (170 mg, 0.52 mmol) in toluene (20 mL) was heated under nitrogen at 110° C. for 16 hours. After concentration, the residue was purified by flash chromatography on silica gel (200-300 mesh) eluting with 1/1 petroleum ether/ethyl acetate to give the title compound. MS: 776 (M+H$^+$).

EXAMPLE 44D 4-(2,6-dichlorobenzyl)-6-(4-(piperazin-1-yl)-3-(trifluoromethyl)phenylamino)-1H-imidazo[4,5-c]pyridine-7-carboxamide To the product of Example 44C (200 mg, 0.26 mol) at 0° C. was added concentrated sulfuric acid (3 mL) and water (0.6 mL) and the mixture was stirred at 0° C. for 30 minutes and then at 90° C. for 20 minutes. After cooling to ambient temperature, ice (10 g) was added and the mixture was extracted with 5/1 dichloromethane/methanol. The organic layer was collected, dried over sodium sulfate, filtered, and concentrated and the residue was purified by preparative HPLC using a gradient of 10/90 to 80/20 acetonitrile/water (containing 0.1% trifluoroacetic acid) to give the title compound. $^1$H NMR (DMSO-d$_6$, 300 MHz): δ 13.70 (s, 1H), 11.95 (s, 1H), 9.64 (s, 1H), 8.66 (m, 3H), 7.97 (s, 1H), 7.76 (d, J=9 Hz, 1H), 7.59 (d, J=8.4 Hz, 2H), 7.42 (m, 1H), 7.24 (d, J=2.1 Hz, 1H), 7.02 (d, J=9 Hz, 1H), 4.75 (s, 2H), 3.22 (m, 4H), 3.01 (m, 4H). MS: 564 (M+H$^+$).

EXAMPLE 45

4-(2,6-dichlorobenzyl)-6-{[4-(piperazin-1-yl)-2-(trifluoromethoxy)phenyl]amino}-1H-imidazo[4,5-c]pyridine-7-carboxamide

EXAMPLE 45A

N,N-dibenzyl-4-bromo-2-(trifluoromethoxy)aniline

To a mixture of 4-bromo-2-(trifluoromethoxy)aniline (5 g, 19.53 mmol) and potassium carbonate (8.09 g, 58.89 mmol) in acetonitrile (200 mL) was added (bromomethyl)benzene (6.96 mL, 58.59 mmol) and the mixture was refluxed for 20 hours. The mixture was filtered and the filtrate was concentrated. The residue was purified by flash chromatography on silica gel (200-300 mesh) eluting with 5/1 petroleum ether/ethyl acetate to give the title compound. MS: 436 (M+H$^+$)

EXAMPLE 45B tert-butyl 4-(4-(dibenzylamino)-3-(trifluoromethoxy)phenyl)piperazine-1-carboxylate A mixture of the product of EXAMPLE 45A (7.92 g, 18.21 mmol), tert-butyl piperazine-1-carboxylate (3.73 g, 20 mmol), palladium diacetate (205 mg, 0.91 mmol), (±)-2,2'-bis(diphenylphosphino)-1,1'-binaphthalene (850 mg, 1.36 mmol) and cesium carbonate (11.88 g, 36 mmol) in toluene (200 mL) was heated under nitrogen at 100° C. for 20 hours. After cooling to ambient temperature, the mixture was concentrated and the residue was diluted with dichloromethane (300 mL), washed with water and brine, dried over sodium sulfate, filtered and concentrated. The residue was purified by flash chromatography on silica gel (200-300 mesh) eluting with 10/1 petroleum ether/ethyl acetate to give the title compound. MS: 542 (M+H$^+$).

EXAMPLE 45C tert-butyl 4-(4-amino-3-(trifluoromethoxy)phenyl)piperazine-1-carboxylate To a solution of the product of EXAMPLE 45B (8.98 g, 16.63 mmol) in methanol (100 mL) was added 10% palladium on carbon (900 mg) and the mixture was stirred at ambient temperature under hydrogen for 5 hours. The catalyst was filtered off and the filtrate was concentrated to give the title compound. MS: 362 (M+H$^+$).

EXAMPLE 45D tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-3-(trifluoromethoxy)phenyl)piperazine-1-carboxylate The title compound was obtained following the procedure described in Example 8J, using the product of Example 45C in place of tert-butyl 4-(4-amino-3-methoxyphenyl)piperazine-1-carboxylate. MS: 792 (M+H$^+$).

EXAMPLE 45E 4-(2,6-dichlorobenzyl)-6-(4-(piperazin-1-yl)-2-(trifluoromethoxy)phenylamino)-1H-imidazo[4,5-c]pyridine-7-carboxamide The title compound was obtained following the procedure described in Example 8K, using the product of Example 45D in place of the product of Example 8J. $^1$H NMR (DMSO-d$_6$, 300 MHz): δ 13.74 (s, 1H), 12.07 (s, 1H), 9.54 (s, 1H), 8.69 (s, 2H), 7.83-7.91 (m, 2H), 7.62-7.65 (m, 1H), 7.46-7.51 (m, 2H), 6.91 (s, 1H), 6.43-6.47 (d, J=12 Hz, 1H), 4.74 (s, 1H), 3.27 (s, 8H). MS: 580 (M+H$^+$).

EXAMPLE 46

4-(2,6-dichlorobenzyl)-6-{[2-methoxy-5-(piperazin-1-yl)phenyl]amino}-1H-imidazo[4,5-c]pyridine-7-carboxamide

EXAMPLE 46A tert-butyl 4-(4-methoxy-3-nitrophenyl)piperazine-1-carboxylate

A mixture of 4-bromo-1-methoxy-2-nitrobenzene (232 mg, 1 mmol), tert-butyl piperazine-1-carboxylate (224 mg, 1.2 mmol), palladium diacetate (23 mg, 1.2 mmol), (±)-2,2'-bis(diphenylphosphino)-1,1'-binaphthalene (93 mg, 0.15 mmol) and cesium carbonate (978 mg, 3 mmol) in 1,4-dioxane (15 mL) was heated at reflux for 16 hours. The mixture was filtered through diatomaceous earth and the filtrate was concentrated. The residue was purified by flash chromatography on silica gel (200-300 mesh) eluting with 4/1 petroleum ether/ethyl acetate to give the title compound.

EXAMPLE 46B tert-butyl 4-(3-amino-4-methoxyphenyl)piperazine-1-carboxylate

A mixture of the product of Example 46A (260 mg, 0.77 mmol) and Raney-Ni (50 mg) in methanol (10 mL) was stirred under hydrogen at ambient temperature for 15 hours. The solution was filtered through diatomaceous earth and the filtrate was concentrated. The residue was purified by flash chromatography on silica gel (200-300 mesh) eluting with a gradient of 3/1 to 2/1 petroleum/ethyl acetate to give the title compound.

EXAMPLE 46C tert-butyl 4-(3-(4-(2,6-dichlorobenzyl)-7-cyano-1-((2-(trimethylsilyl)ethoxy)methyl)-1H-imidazo[4,5-c]pyridin-6-ylamino)-4-methoxyphenyl)piperazine-1-carboxylate The title compound was obtained following the procedure described in Example 8J, using the product of Example 46B in place of tert-butyl 4-(4-amino-3-methoxyphenyl)piperazine-1-carboxylate. MS: 724 (M+H$^+$).

EXAMPLE 46D 4-(2,6-dichlorobenzyl)-6-(2-methoxy-5-(piperazin-1-yl)phenylamino)-1H-imidazo[4,5-c]pyridine-7-carboxamide The title compound was obtained following the procedure described in Example 8K, using the product of Example 46C in place of the product of Example 8J. $^1$H NMR (DMSO-d$_6$, 300 MHz): δ 11.65 (s, 1H), 9.54 (s, 1H), 8.68 (brs, 2H), 8.57 (s, 7.70 (d, J=2.7 Hz, 2H), 7.50 (d, J=8.1 Hz, 2H), 7.32 (m, 1H), 6.83 (d, J=8.1 Hz, 1H), 6.45 (d, J=8.7, 2.7 Hz, 1H), 4.73 (s, 2H), 3.77 (s, 3H), 331 (m, 4H), 3.01 (m, 4H). MS: 525 (M+H$^+$).

EXAMPLE 47

4-(2,6-dichlorobenzyl)-6-{[4-(hexahydropyrrolo[1,2-a]pyrazin-2(1H)-yl)-2-methoxyphenyl]amino}-1H-imidazo[4,5-c]pyridine-7-carboxamide

EXAMPLE 47A 2-(3-methoxy-4-nitrophenyl)octahydropyrrolo[1,2-a]pyrazine

A mixture of 4-fluoro-2-methoxy-1-nitrobenzene (342 mg, 2 mmol), octahydropyrrolo[1,2-a]pyrazine (252 mg, 2 mmol) and potassium carbonate (552 mg, 4 mmol) in dimethylacetamide (10 mL) was heated at 100° C. for 16 hours. After cooling to ambient temperature, the mixture was poured into water and extracted with ethyl acetate (3×50 mL). The combined organic phase was washed with brine, dried over sodium sulfate, filtered and concentrated. The residue was purified by flash chromatography on silica gel (200-300 mesh) eluting with 98/2 dichloromethane/methanol to give the title compound. MS: 278 (M+H$^+$).

EXAMPLE 47B 4-(hexahydropyrrolo[1,2-a]pyrazin-2(1H)-yl)-2-methoxy aniline

To a suspension of the product of Example 47A (1.58 g, 5.68 mmol) in methanol (100 mL) was added Raney-Ni (158 mg) and the mixture was stirred at ambient temperature under hydrogen for 4 hours. The catalyst was filtered off and the filtrate was concentrated to give the title compound, which was used in the next step without further purification. MS: 248 (M+H$^+$).

EXAMPLE 47C 4-(2,6-dichlorobenzyl)-6-(4-(hexahydropyrrolo[1,2-a]pyrazin-2(1H)-yl)-2-methoxyphenylamino)-1-((2-(trimethylsilyl)ethoxy)methyl)-1H-imidazo[4,5-c]pyridine-7-carbonitrile The title compound was obtained following the procedure described in Example 8J, using the product of Example 47B in place of tert-butyl 4-(4-amino-3-methoxyphenyl)piperazine-1-carboxylate. MS: 678 (M+H$^+$).

EXAMPLE 47D 4-(2,6-dichlorobenzyl)-6-(4-(hexahydropyrrolo[1,2-a]pyrazin-2(1H)-yl)-2-methoxyphenylamino)-1H-imidazo[4,5-c]pyridine-7-carboxamide The title compound was obtained following the procedure described in Example 8K, using the product of Example 47C in place of the product of Example 8J. $^1$H NMR (DMSO-d$_6$, 300 MHz): δ 11.64 (brs, 1H), 10.25 (brs, 1H), 9.75 (brs, 1H), 9.50 (brs, 1H), 8.56 (s, 1H), 7.65-7.60 (m, 3H), 7.49-7.46 (m, 1H), 6.63-6.60 (m, 1H), 6.04-6.02 (m, 1H), 4.71 (s, 2H), 3.92-3.65 (m, 6H), 3.46-3.11 (m, 5H), 2.93-2.73 (m, 1H), 2.29-1.67 (m, 4H). MS: 566 (M+H$^+$).

EXAMPLE 48

4-(2,6-dichlorobenzyl)-6-{[2,3-dimethyl-4-(piperazin-1-yl)phenyl]amino}-1H-imidazo[4,5-c]pyridine-7-carboxamide

EXAMPLE 48A

N,N-dibenzyl-4-bromo-2,3-dimethylaniline

The title compound was obtained following the procedure described in Example 45A, using 4-bromo-2,3-dimethylaniline in place of 4-bromo-2-(trifluoromethoxy)aniline. MS: 380 (M+H$^+$).

EXAMPLE 48B tert-butyl 4-(4-(dibenzylamino)-2,3-dimethylphenyl)piperazine-1-carboxylate The title compound was obtained following the procedure described in Example 45B, using the product of Example 48A in place of the product of Example 45A. MS: 486 (M+H$^+$).

EXAMPLE 48C tert-butyl 4-(4-amino-2,3-dimethylphenyl)piperazine-1-carboxylate The title compound was obtained following the procedure described in Example 45C, using the product of Example 48B in place of the product of Example 45B. MS: 306 (M+H$^+$).

EXAMPLE 48D tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-3,5-difluorophenyl)piperazine-1-carboxylate The title compound was obtained following the procedure described in Example 8J, using product of Example 48C in place of tert-butyl 4-(4-amino-3-methoxyphenyl)piperazine-1-carboxylate. MS: 736 (M+H$^+$).

EXAMPLE 48E 4-(2,6-dichlorobenzyl)-6-(2,6-difluoro-4-(piperazin-1-yl)phenylamino)-1H-imidazo[4,5-c]pyridine-7-carboxamide The title compound was obtained following the procedure described in Example 8K, using the product of Example 48D in place of the product of Example 8J. $^1$H NMR (CD$_3$OD, 300 MHz): δ 12.15 (s, 1H), 10.38 (br, 1H), 9.54 (br, 2H), 9.38 (s, 1H), 8.56 (br, 1H), 8.36-8.19 (m, 4H), 7.26 (d, J=8.7 Hz, 1H), 5.47 (s, 2H), 4.09 (br, 4H), 3.75 (br, 4H), 3.00 (s, 3H), 2.93 (s, 3H). MS: 526 (M+H$^+$).

EXAMPLE 49

4-(2,6-dichlorobenzyl)-6-{[2-methoxy-4-(pyrrolidin-1-ylmethyl)phenyl]amino}-1H-imidazo[4,5-c]pyridine-7-carboxamide

EXAMPLE 49A (4-amino-3-methoxyphenyl)(pyrrolidin-1-yl)methanone

To a solution of 4-amino-3-methoxybenzoic acid (167 mg, 1 mmol) in dichloromethane (20 mL) at 0° C. was added pyrrolidine (71 mg, 1 mmol), hydroxybenzotriazole monohydrate (270 mg, 2 mmol), 1-ethyl-3-(3-dimethylaminopropyl)carbodiimide (384 mg, 2 mmol) and triethylamine (0.5 mL, 3 mmol). After stirring for 2 hours, the mixture was diluted with water and extracted with dichloromethane. The organic phase was concentrated and the residue was purified by flash chromatography on silica gel (200-300 mesh) eluting with 5/1 petroleum ether/ethyl acetate to give the title compound. MS: 220 (M+H$^+$).

EXAMPLE 49B 2-methoxy-4-(pyrrolidin-1-ylmethyl)aniline

To a solution of the product of Example 49A (220 mg, 3.64 mmol) in tetrahydrofuran (20 mL) at 0° C. was added borane tetrahydrofuran complex (18 mL, 18 mmol) and the mixture was stirred at 0° C. for 2 hours and at 60° C. for 4 hours. After cooling to ambient temperature, methanol (20 mL) was added and stirring was continued for 30 minutes. The organic phase was concentrated and the residue was purified via preparative HPLC using a gradient of 10/90 to 80/20 acetonitrile/water (containing 0.1% trifluoroacetic acid) to give the title compound. MS: 207 (M+H$^+$).

EXAMPLE 49C 4-(2,6-dichlorobenzyl)-6-(2-methoxy-4-(pyrrolidin-1-ylmethyl)phenylamino)-1-((2-(trimethylsilyl)ethoxy)methyl)-1H-imidazo[4,5-c]pyridine-7-carbonitrile A mixture of the product of Example 8I (120 mg, 0.87 mmol), the product of Example 49B (179 mg, 0.87 mmol), tricyclohexylphosphine (73 mg, 0.26 mmol), palladium diacetate (31 mg, 0.13 mmol) and cesium carbonate (568 mg, 1.74 mmol) in toluene (50 mL) was heated under nitrogen at 100° C. for 14 hours. After cooling, the mixture was filtered, concentrated and purified by flash chromatography on silica gel (200-300 mesh) eluting with 5/1 petroleum ether/ethyl acetate to provide the title compound. MS: 637 (M+H$^+$).

EXAMPLE 49D 4-(2,6-dichlorobenzyl)-6-(2-methoxy-4-(pyrrolidin-1-ylmethyl)phenylamino)-1H-imidazo[4,5-c]pyridine-7-carboxamide To a solution of the product of Example 49C (80 mg, 0.13 mmol) in concentrated sulfuric acid (5 mL) at 0° C. was added water (1 mL) and the mixture was heated to 95° C. for 20 minutes. After cooling, the mixture was diluted with water (3 mL), adjusted to pH 8-9 with saturated sodium bicarbonate solution and extracted with dichloromethane (3×20 mL). The combined organic phase was concentrated and the residue was purified via preparative HPLC using a gradient of 10/90 to 75/25 acetonitrile/water (containing 0.1% trifluoroacetic acid) to give the title compound. $^1$H NMR (DMSO-d$_6$, 300 MHz): δ 12.00 (br, 1 H), 9.68 (br, 1 H), 8.62 (s, 1 H), 7.85 (d, J=8.4 Hz, 1 H), 7.73 (s, 1 H), 7.61-7.58 (m, 2 H), 7.48-7.42 (m, 1 H), 7.08 (d, J=1.2 Hz, 1 H), 6.62-6.58 (dd, J=8.4, 1.2 Hz, 1 H), 4.75 (s, 2 H), 4.23 (d, 2 H), 3.88 (s, 3 H), 3.44-3.41 (m, 8 H). MS: 525 (M+H$^+$).

EXAMPLE 50

7-{[2-bromo-4-(piperazin-1-yl)phenyl]amino}-5-(2,6-dichlorobenzyl)[1,2,4]triazolo[4,3-c]pyrimidine-8-carboxamide

EXAMPLE 50A tert-butyl 4-(3-bromo-4-nitrophenyl)piperazine-1-carboxylate

The title compound was obtained following the procedure as described Example 28A, using 2-bromo-4-fluoro-1-nitrobenzene in place of 4-bromo-2-fluoro-1-nitrobenzene. MS: 408 (M+H$^+$).

EXAMPLE 50B tert-butyl 4-(4-amino-3-bromophenyl)piperazine-1-carboxylate

The title compound was obtained following the procedures (two steps) described in Example 47A and Example 47B using 2-bromo-4-fluoro-1-nitrobenzene in place of 4-fluoro-2-methoxy-1-nitrobenzene and tert-butyl piperazine-1-carboxylate in place of octahydropyrrolo[1,2-a]pyrazine. MS: 386 (M+H$^+$).

EXAMPLE 50C tert-butyl 4-(3-bromo-4-(5-carbamoyl-6-chloro-2-(methylthio)pyrimidin-4-ylamino)phenyl)piperazine-1-carboxylate The title compound was obtained following the procedure described in Example 15D, using the product of Example 50B in place of the product of Example 15C, MS: 557 (M+H$^+$).

EXAMPLE 50D tert-butyl 4-(3-bromo-4-(5-carbamoyl-6-hydrazinyl-2-(methylthio)pyrimidin-4-ylamino)phenyl)piperazine-1-carboxylate The title compound was obtained following the procedure described in Example 15E, using the product of Example 50C in place of the product of Example 15D. MS: 553 (M+H$^+$).

EXAMPLE 50E tert-butyl 4-(3-bromo-4-(8-carbamoyl-5-(methylthio)-[1,2,4]triazolo[4,3-c]pyrimidin-7-ylamino)phenyl)piperazine-1-carboxylate The title compound was obtained following the procedure described in Example 15F, using the product of Example 50D in place of the product of Example 15E. MS: 563 (M+H$^+$).

EXAMPLE 50F tert-butyl 4-(3-bromo-4-(8-carbamoyl-5-(2,6-dichlorobenzyl)-[1,2,4]triazolo[4,3-c]pyrimidin-7-ylamino)phenyl)piperazine-1-carboxylate The title compound was obtained following the procedure described in Example 15G, using the product of Example 50E in place of the product of Example 15F. MS: 675 (M+H$^+$).

EXAMPLE 50G 7-(2-bromo-4-(piperazin-1-yl)phenylamino)-5-(2,6-dichlorobenzyl)-[1,2,4]triazolo[4,3-c]pyrimidine-8-carboxamide The title compound was obtained following the procedure described in Example 15H, using the product of Example 50F in place of the product of Example 15G. $^1$H NMR (DMSO-d$_6$, 300 MHz): δ 12.05 (s, 1H), 9.62 (s, 1H), 8.90 (s, 1H), 8.70 (br, 2H), 7.98 (s, 1H), 7.55 (d, J=8.4 Hz, 2H), 7.45-7.42 (m, 1H), 7.16-7.10 (m, 2H), 6.48-6.45 (m, 1H), 4.89 (s, 2H), 3.27-3.23 (m, 8H). MS: 575 (M+H$^+$).

EXAMPLE 51

4-(2,6-dichlorobenzyl)-6-{[2-fluoro-5-methyl-4-(piperazin-1-yl)phenyl]amino}-1H-imidazo[4,5-c]pyridine-7-carboxamide

EXAMPLE 51A

N,N-dibenzyl-4-bromo-2-fluoro-5-methylbenzenamine

A suspension of 4-bromo-2-fluoro-5-methylbenzenamine (1 g, 4.9 mmol), (bromomethyl)benzene (2.5 g, 14.7 mmol) and potassium carbonate (2 g, 14.7 mmol) in acetonitrile (80 mL) was heated in a sealed tube at 100° C. for 16 hours. After concentration, the residue was diluted with ethyl acetate (80 mL), washed with water (20 mL), dried over anhydrous sodium sulfate filtered, and concentrated. The residue was purified by flash chromatography on silica gel (200-300 mesh) eluting with 50/1 petroleum ether/ethyl acetate to give the title compound. MS: 384 (M+H$^+$).

EXAMPLE 51B tert-butyl 4-(4-(dibenzylamino)-5-fluoro-2-methylphenyl)piperazine-1-carboxylate A suspension of the product of Example 51A (3.2 g, 8.4 mmol), tert-butyl piperazine-1-carboxylate (1.9 g, 10.1 mmol), palladium(II) acetate (189 mg, 0.84 mmol), 2,2'-bis(diphenylphosphino)-1,1'-binaphthyl (1.05 g, 1.7 mmol) and cesium carbonate (5.5 g, 16.8 mmol) in toluene (200 mL) was heated at reflux under nitrogen for 16 hours. After concentration, the residue was purified by flash chromatography on silica gel (200-300 mesh) eluting with 10/1 petroleum ether/ethyl acetate to give the title compound. MS: 490 (M+H$^+$).

EXAMPLE 51C tert-butyl 4-(4-amino-5-fluoro-2-methylphenyl)piperazine-1-carboxylate A suspension of the product of Example 51B (2 g, 4.1 mmol) and 10% palladium on carbon (200 mg) in methanol (100 mL) was stirred under hydrogen for 18 hours. The catalyst was filtered and the filtrate was concentrated and the residue was purified by flash chromatography on silica gel (200-300 mesh) eluting with 1/1 petroleum ether/ethyl acetate to give the title compound. MS: 310 (M+H$^+$).

EXAMPLE 51D tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-5-fluoro-2-methylphenyl)piperazine-1-carboxylate A suspension of the product of Example 8I (300 mg, 0.64 mmol), the product of Example 51C (238 mg, 0.77 mmol), palladium(II) acetate (30 mg, 0.13 mmol), tricyclohexylphosphine (73 mg, 0.26 mmol) and cesium carbonate (417 mg, 1.28 mmol) in toluene (30 mL) was heated at reflux under nitrogen for 18 hours. After concentration, the residue was purified by flash chromatography on silica gel (200-300 mesh) eluting with 5/1 petroleum ether/ethyl acetate to give the title compound. MS: 740 (M+H$^+$).

EXAMPLE 51E 4-(2,6-dichlorobenzyl)-6-(2-fluoro-5-methyl-4-(piperazin-1-yl)phenylamino)-1H-imidazo[4,5-c]pyridine-7-carboxamide To the product of Example 51D (190 mg, 0.26 mmol) at 0° C. was added concentrated sulfuric acid (3 mL) and water (0.6 mL) and the mixture was heated at 90° C. for 20 minutes. After quenching with water (20 mL) and adjusting to pH 8 with saturated sodium bicarbonate solvent, the mixture was extracted with 4/1 dichloromethane/methanol (3×100 mL). The organic layers were collected, dried over anhydrous sodium sulfate, filtered, concentrated and purified by preparative HPLC using a gradient of 10/90 to 75/25 acetonitrile/ water (containing 0.1% trifluoroacetic acid) to give the title compound. $^1$H NMR (DMSO-$d_6$, 300 MHz): δ 13.63 (s, 1H), 11.98 (s, 1H), 9.63 (s, 1H), 8.64 (m, 3H), 7.90 (d, 1H), 7.83 (s, 1H), 7.56 (d, 2H), 7.39 (t, 1H), 6.90 (d, 1H), 4.74 (s, 2H), 3.25 (m, 4H), 2.95 (m, 4H), 2.07 (s, 3H). MS: 528 (M+H$^+$).

EXAMPLE 52

4-(2,6-dichlorobenzyl)-6-{[3,5-difluoro-2-methoxy-4-(piperazin-1-yl)phenyl]amino}-1H-imidazo[4,5-c] pyridine-7-carboxamide

EXAMPLE 52A 1,2,3-trifluoro-4-methoxy-5-nitrobenzene

To a solution of 1,2,3-trifluoro-4-methoxybenzene (1.6 g, 10 mmol) in acetic acid (20 mL) was added nitric acid (5 mL) and the mixture was heated at 60° C. for 3 hours. After cooling to ambient temperature, water (100 mL) was added and the mixture was extracted with ethyl acetate (3×100 mL). The organic layers were concentrated to give the crude title compound, which was used in the next step without further purification.

EXAMPLE 52B tert-butyl 4-(2,6-difluoro-3-methoxy-4-nitrophenyl) piperazine-1-carboxylate To a solution of the product of Example 52A (500 mg, 2.4 mmol) in acetonitrile (20 mL) was added potassium carbonate (660 mg, 4.8 mmol) and tert-butyl piperazine-1-carboxylate (900 mg, 4.8 mmol) and the mixture was heated to 80° C. for 3 hours. After cooling, the mixture was filtered, concentrated and purified by flash chromatography on silica gel (200-300 mesh) eluting with 20/1 petroleum ether/ethyl acetate to provide the title compound. MS: 374 (M+H$^+$).

EXAMPLE 52C tert-butyl 4-(4-amino-2,6-difluoro-3-methoxyphenyl) piperazine-1-carboxylate To a solution of the product of Example 52B (600 mg, 1.6 mmol) in methanol (100 mL) was added Raney Nickel (60 mg) and the mixture was stirred under hydrogen for 14 hours. The catalyst was filtered off and the filtrate was concentrated and purified by flash chromatography on silica gel (200-300 mesh) eluting with 100/1 dichloromethane/methanol to provide the title compound. MS: 344 (M+H$^+$),

EXAMPLE 52D tert-butyl 4-(4-(7-cyano-4-(2,6-dichlorobenzyl)-1-((2-(trimethylsilyl)ethoxy)methyl)-1H-imidazo[4,5-c]pyridin-6-ylamino)-2,6-difluoro-3-methoxyphenyl) piperazine-1-carboxylate A mixture of the product of Example 8I (250 mg, 0.53 mmol), the product of Example 52C (220 mg, 0.64 mmol), tricyclohexylphosphine (45 mg, 0.16 mmol), palladium diacetate (19 mg, 0.08 mmol) and cesium carbonate (348 mg, 1.07 mmol) in toluene (50 mL) was heated at 100° C. under nitrogen for 14 hours. After cooling to ambient temperature, the mixture was filtered, concentrated and purified by flash chromatography on silica gel (200-300 mesh) eluting with 5/1 petroleum ether/ethyl acetate to provide the title compound. MS: 774 (M+H$^+$).

EXAMPLE 52E 4-(2,6-dichlorobenzyl)-6-(3,5-difluoro-2-methoxy-4-(piperazin-1-yl)phenylamino)-1H-imidazo[4,5-c] pyridine-7-carboxamide To a solution of the product of Example 52D (130 mg, 0.17 mmol) in concentrated sulfuric acid (5 mL) at 0° C. was added water (1 mL) and the mixture was heated at 95° C. for 20 minutes. After cooling to ambient temperature, the mixture was diluted with water (3 mL), adjusted to pH 8-9 with saturated sodium bicarbonate solution and extracted with dichloromethane (3×20 mL). The combined organic phase was concentrated and the residue was purified by preparative HPLC using a gradient of 10/90 to 80/20 acetonitrile/water (containing 0.1% trifluoroacetic acid) to give the title compound. $^1$H NMR (DMSO-$d_6$, 300 MHz): δ 12.35 (s, 1 H), 9.61 (s, 1 H), 8.97 (s, 2 H), 8.66 (s, 1 H), 7.91 (s, 1 H), 7.74-7.66 (m 1 H), 7.56-7.53 (m, 2 H), 7.43-7.37 (m, 1 H), 4.77 (s, 2 H), 3.82 (s, 3 H), 3.21 (m, 8 H). MS: 562 (M+H$^+$).

EXAMPLE 53

4-(2,6-dichlorobenzyl)-6-[(6-methoxy-1,2,3,4-tetrahydroisoquinolin-7-yl)amino]-1H-imidazo[4,5-c] pyridine-7-carboxamide

EXAMPLE 53A methyl 3-methoxyphenethylcarbamate

To a solution of methyl carbonochloridate (25 g, 265 mmol) in dichloromethane (100 mL) at 0° C. was added slowly methyl 3-methoxyphenethylcarbamate (40 g, 265 mmol). After the addition, stirring was continued for 0.5 hours at 0° C. and at ambient temperature for 16 hours. The mixture was poured into ice-brine (200 mL) and extracted with dichloromethane (3×100 mL). The combined organic layer was dried over anhydrous sodium sulfate, filtered and concentrated and the residue was washed with hexane (50 mL) and concentrated to give the title compound. MS: 210 (M+H$^+$).

EXAMPLE 53B 6-methoxy-3,4-dihydroisoquinolin-1(2H)-one

To polyphosphoric acid (70 mL) at 120° C. was added slowly the product of Example 53A (10 g, 47.8 mmol) and the mixture was stirred at 120° C. for 1 hour. After cooling, the mixture was poured into ice-water (300 mL) and extracted with dichloromethane (2×200 mL). The combined organic layer was washed with brine (100 mL), dried over anhydrous sodium sulfate, filtered and concentrated to give the title compound. MS: 178 (M+H$^+$).

EXAMPLE 53C 6-methoxy-1,2,3,4-tetrahydroisoquinoline

To a suspension of lithium aluminum hydride (10 g, 46 mmol) in tetrahydrofuran (100 mL) at 0° C. under nitrogen was added slowly a solution of the product of Example 53B (4.1 g, 23 mmol) in tetrahydrofuran (50 mL) over 0.5 hours and the mixture was heated at 70° C. for 2 hours. After cooling to 0° C., 15% sodium hydroxide (4.9 mL) was added slowly and the mixture was filtered and washed with ethyl acetate (50 mL). The filtrate was concentrated to give the crude title compound. MS: 164 (M+H$^+$).

EXAMPLE 53D tert-butyl 6-methoxy-3,4-dihydroisoquinoline-2(1H)-carboxylate

To a solution of the product of Example 53C (1.88 g, 11.5 mmol) in dichloromethane (40 mL) was added triethylamine (2.3 g, 23 mmol) and di-tert-butyl dicarbonate (3 g, 13.8 mmol). After stirring for 16 hours, the mixture was poured into water (50 mL) and extracted with dichloromethane (2×100 mL). The combined organic layer was dried over anhydrous sodium sulfate, filtered, concentrated and purified by flash chromatography eluting with 10:1 hexane:ethyl acetate to give the title compound. MS: 264 (M+H$^+$).

EXAMPLE 53E tert-butyl 6-methoxy-7-nitro-3,4-dihydroisoquinoline-2(1H)-carboxylate To a solution of the product of Example 53D (2.46 g, 9.35 mmol) in nitromethane (30 mL) at −10° C. was added acetic anhydride (5.7 g, 56.1 mmol) and concentrated nitric acid (0.88 g, 14 mmol). After stirring for 3 hours, the mixture was adjusted to pH 7 with aqueous sodium bicarbonate solution and extracted with dichloromethane (2×100 mL). The combined organic layer was dried over anhydrous sodium sulfate, filtered, concentrated and purified by flash chromatography eluting with 5:1 hexane:ethyl acetate to give the title compound. MS: 309 (M+H$^+$).

EXAMPLE 53F tert-butyl 7-amino-6-methoxy-3,4-dihydroisoquinoline-2(1H)-carboxylate To a solution of the product of Example 53E (550 mg, 1.78 mmol) in methanol (10 mL) was added Raney Ni (55 mg) and the mixture was stirred at ambient temperature under hydrogen for 16 hours. The mixture was filtered, concentrated and dried under vacuum to give the crude title compound. MS: 279 (M+H$^+$).

EXAMPLE 53G tert-butyl 7-(7-cyano-4-(2,6-dichlorobenzyl)-1-((2-(trimethylsilyl)ethoxy)methyl)-1H-imidazo[4,5-c]pyridin-6-ylamino)-6-methoxy-3,4-dihydroisoquinoline-2(1H)-carboxylate To a solution of the product of Example 8I (163 mg, 0.35 mmol) in toluene (10 mL) was added the product of Example 53F (98 mg, 0.35 mmol), palladium diacetate (7 mg, 0.03 mmol), tricyclohexylphosphine (16.8 mg, 0.06 mmol) and cesium carbonate (208 mg, 0.64 mmol) and the mixture was stirred under nitrogen at 100° C. for 16 hours. After cooling and concentration, the residue was purified by flash chromatography on silica gel eluting with 100:1 dichloromethane/methanol to give the title compound. MS: 709 (M+H$^+$).

EXAMPLE 53H 4-(2,6-dichlorobenzyl)-6-(6-methoxy-1,2,3,4-tetrahydroisoquinolin-7-ylamino)-1H-imidazo[4,5-c]pyridine-7-carboxamide To the product of Example 53G (108 mg, 0.15 mmol) at 0° C. was added concentrated sulfuric acid (3 mL) and water (0.6 mL) and the mixture was stirred at 90° C. for 10 minutes. After cooling, the mixture was slowly poured into ice-water (10 mL), adjusted to pH 7 with sodium bicarbonate and extracted with 4/1 dichloromethane/methanol (150 mL). The organic phase was washed with water (50 mL), dried over anhydrous sodium sulfate, filtered, and concentrated. The residue was purified by preparative HPLC using a gradient of 10/90 to 30/20 acetonitrile/water (containing 0.1% trifluoroacetic acid) to give the title compound as the trifluoroacetate salt. $^1$H NMR (DMSO-d$_6$, 300 MHz): δ 13.6 (s, 1 H), 12.1 (s, 1 H), 9.81 (s, 1 H), 8.88 (s, 2 H), 8.82 (s, 1 H), 7.90 (s, 1 H), 7.91 (s, 1 H), 7.60 (d, J=8.1 Hz, 2 H), 7.43 (t, J=7.5 Hz, 1 H), 6.80 (s, 1 H), 4.76 (s, 2 H), 3.89 (s 5 H), 3.37 (br, 2 H), 2.91 (s, 2 H). MS: 497 (M+H$^+$).

EXAMPLE 54

6-{[2-chloro-4-(piperidin-4-yl)phenyl]amino}-4-(2,6-dichlorobenzyl)-1H-imidazo[4,5-c]pyridine-7-carboxamide

EXAMPLE 54A tert-butyl 4-(4-(4-(2,6-dichlorobenzyl)-7-cyano-1-((2-(trimethylsilyl)ethoxy)methyl)-1H-imidazo[4,5-c]pyridin-6-ylamino)-3-chlorophenyl)piperidine-1-carboxylate The title compound was obtained following the procedure described in Example 8J, using the product of Example 60E in place of tert-butyl 4-(4-amino-3-methoxyphenyl)piperazine-1-carboxylate. MS: 741 (M+H$^+$).

EXAMPLE 54B tert-butyl 4-(4-(4-(2,6-dichlorobenzyl)-7-carbamoyl-1-((2-(trimethylsilyl)ethoxy)methyl)-1H-imidazo[4,5-c]pyridin-6-ylamino)-3-chlorophenyl)piperidine-1-carboxylate To a mixture of the product of Example 54A (62 mg, 0.084 mmol) and 2N potassium hydroxide solution in methanol (20 mL) was added 25% hydrogen peroxide solution (0.4 mL), and the mixture was stirred at ambient temperature for 15 hours. The mixture was concentrated, diluted with ethyl acetate and washed with water. The organic layer was concentrated and purified by flash chromatography on silica gel (200-300 mesh) eluting with 30:1 dichloromethane/methanol to give the title compound. MS: 761 (M+H$^+$).

EXAMPLE 54C 4-(2,6-dichlorobenzyl)-6-(2-chloro-4-(piperidin-4-yl)phenylamino)-1H-imidazo[4,5-c]pyridine-7-carboxamide The title compound was obtained following the procedure described in Example 8K, using the product of Example 54B in place of the product of Example 8J. $^1$H NMR (DMSO-d$_6$, 300 MHz): δ 13.67 (s, 1H), 12.01 (s, 1H), 9.58 (s, 1H), 8.63 (s, 1H), 7.81 (d, J=7.7 Hz, 1H), 7.57 (d, J=8.1 Hz, 1H), 7.44-7.39 (m, 1H), 7.16 (d, J=2.1 Hz, 1H), 6.64 (dd, J=1.8 Hz, J=9 Hz, 1H), 4.72 (s, 1H), 3.40-3.39 (m, 2H), 2.98 (t, 2H), 2.71 (m, 1H), 1.93-1.83 (m, 2H), 1.72-1.67 (m, 2H). MS: 529 (M+H$^+$).

EXAMPLE 55

7-(2-chloro-4-(piperidin-4-yl)phenylamino)-5-(2-chlorobenzyl)-3-ethyl-[1,2,4]triazolo[4,3-c]pyrimidine-8-carboxamide

EXAMPLE 55A tert-butyl 4-(4-(5-carbamoyl-6-chloro-2-(methylthio) pyrimidin-4-ylamino)-3-chlorophenyl)piperidine-1-carboxylate A mixture of the product of Example 2D (213 mg, 0.9 mmol), the product of Example 60E (278 mg, 0.9 mmol) and N,N-diisopropylethylamine (232 mg, 1.8 mmol) in 1,4-dioxane (10 mL) was heated in a sealed tube at 120° C. for 18 hours. The mixture was concentrated and the residue was purified by flash chromatography on silica gel (200-300 mesh) eluting with 99/1 dichloromethane/methanol to give the title compound. MS: 512 (M+H$^+$).

EXAMPLE 55B tert-butyl 4-(4-(5-carbamoyl-6-hydrazinyl-2-(methylthio)pyrimidin-4-ylamino)-3-chlorophenyl)piperidine-1-carboxylate To a solution of the product of Example 55A (131 mg, 0.26 mmol) in 1,4-dioxane (3 mL) was added hydrazine hydrate (50 mg, 0.78 mmol) and the mixture was stirred at ambient temperature for 4 hours. The mixture was concentrated and the residue was washed with hexane and dried to give the title compound. The crude title compound was used in the next step without further purification. MS: 508 (M+H$^+$).

EXAMPLE 55C tert-butyl 4-(4-(8-carbamoyl-3-ethyl-5-(methylthio)-[1,2,4]triazolo[4,3-c]pyrimidin-7-ylamino)-3-chlorophenyl)piperidine-1-carboxylate To a solution of the product of Example 55B (250 mg, 0.49 mmol) was added 1,1,1-triethoxypropane (3 mL) and the mixture was stirred at ambient temperature for 1 hour and heated at 55° C. for 5 hours. After cooling, 90/10 petroleum ether/ethyl acetate was added and the precipitate was collected. The solid was washed with petroleum ether and dried under vacuum to give the title compound. MS: 546 (M+H$^+$).

EXAMPLE 55D tert-butyl 4-(4-(8-carbamoyl-5-(2-chlorobenzyl)-3-ethyl-[1,2,4]triazolo[4,3-c]pyrimidin-7-ylamino)-3-chlorophenyl)piperidine-1-carboxylate The title compound was obtained following the procedure described in Example 19A, using the product of Example 55C in place of the product of Example 13E. MS: 624 (M+H$^+$).

EXAMPLE 55E 7-(2-chloro-4-(piperidin-4-yl)phenylamino)-5-(2-chlorobenzyl)-3-ethyl-[1,2,4]triazolo[4,3-c]pyrimidine-8-carboxamide The title compound was obtained following the procedure described in Example 15H, using the product of Example 55D in place of the product of Example 15G. $^1$H NMR (DMSO-d$_6$, 300 MHz): δ 12.45 (s, 1H), 9.22-9.07 (m, 3H), 8.05 (brs, 1H), 7.58-7.42 (m, 4H), 7.28-7.23 (m, 2H), 6.63 (d, J=8.4 Hz, 1H), 4.90 (s, 2H), 3.49-3.35 (m, 4H); 3.00-2.94 (m, 2H), 2.83-2.73 (m, 1H), 1.88 (br, 4H), 1.50 (t, J=6.9 Hz, 3H). MS: 524 (M+H$^+$).

EXAMPLE 56

5-(2,6-dichlorobenzyl)-7-{[2-methoxy-4-(piperazin-1-yl)phenyl]amino}-3-methyl[1,2,4]triazolo[4,3-c]pyrimidine-8-carboxamide

EXAMPLE 56A tert-butyl 4-(4-(8-carbamoyl-3-methyl-5-(methylthio)-[1,2,4]triazolo[4,3-c]pyrimidin-7-ylamino)-3-methoxyphenyl)piperazine-1-carboxylate The title compound was obtained following the procedure described in Example 55C, using 1,1,1-trimethoxyethane in place of 1,1,1-triethoxypropane. MS: 529 (M+H$^+$).

EXAMPLE 56B tert-butyl 4-(4-(8-carbamoyl-5-(2,6-dichlorobenzyl)-3-methyl-[1,2,4]triazolo[4,3-c]pyrimidin-7-ylamino)-3-methoxyphenyl)piperazine-1-carboxylate The title compound was obtained following the procedure described in Example 15G, using the product of Example 56A in place of the product of Example 15F. MS: 641 (M+H$^+$).

EXAMPLE 56C 5-(2,6-dichlorobenzyl)-7-(2-methoxy-4-(piperazin-1-yl)phenylamino)-3-methyl-[1,2,4]triazolo[4,3-c]pyrimidine-8-carboxamide The title compound was obtained following the procedure described in Example 15H, using the product of Example 56B in place of the product of Example 15G. $^1$H NMR (DMSO-d$_6$+D$_2$O, 300 MHz): δ 7.60-7.53 (m, 2H), 7.51-7.49 (m, 1H), 6.94 (d, J=9.0 Hz, 1H), 6.58 (s, 1H), 5.95-5.91 (m, 1H), 4.99 (s, 2H), 3.80 (s, 3H), 3.27-3.25 (m, 8H), 3.01 (s, 3H). MS: 541 (M+H$^+$).

EXAMPLE 57

5-(2,6-dichlorobenzyl)-3-ethyl-7-{[2-methoxy-4-(piperazin-1-yl)phenyl]amino}[1,2,4]triazolo[4,3-c]pyrimidine-8-carboxamide

EXAMPLE 57A tert-butyl 4-(4-(8-carbamoyl-3-ethyl-5-(methylthio)-[1,2,4]triazolo[4,3-c]pyrimidin-7-ylamino)-3-methoxyphenyl)piperazine-1-carboxylate To a solution of the product of Example 2F (300 mg, 0.59 mmol) was added 1,1,1-triethoxypropane (3 mL) and the mixture was stirred at ambient temperature for 1 hour and at 55° C. for 4 hours. After cooling, 90/10 petroleum ether/ethyl acetate was added and the precipitate was collected. The solid was washed with petroleum ether and dried under vacuum to give the title compound, which was used in the next step without further purification. MS: 543 (M+H$^+$).

EXAMPLE 57B tert-butyl 4-(4-(8-carbamoyl-5-(2,6-dichlorobenzyl)-3-ethyl-[1,2,4]triazolo[4,3-d]pyrimidin-7-ylamino)-3-methoxyphenyl)piperazine-1-carboxylate To a mixture of the product of Example 57A (110 mg, 0.2 mmol) and tetrakis(triphenylphosphine) palladium (23 mg, 0.02 mmol) was added 0.5M 2,6-dichlorobenzyl zinc bromide in tetrahydrofuran (4 mL, 2 mmol) under nitrogen and the mixture was heated at 60° C. for 16 hours. After cooling to ambient temperature, the mixture was diluted with dichloromethane (50 mL) and washed with saturated aqueous sodium bicarbonate. The organic phase was separated and the aqueous phase was extracted with dichloromethane (2×20 mL). The combined organic phase was washed with brine, dried over sodium sulfate, filtered and concentrated. The residue was purified by flash chromatography on silica gel (200-300 mesh) eluting with 98/2 dichloromethane/methanol to give the title compound. MS: 655 (M+H$^+$).

EXAMPLE 57C 5-(2,6-dichlorobenzyl)-3-ethyl-7-(2-methoxy-4-(piperazin-1-yl)phenylamino)-[1,2,4]triazolo[4,3-c]pyrimidine-8-carboxamide To a solution of the product of Example 57B (130 mg, 0.2 mmol) in dichloromethane (12 mL) was added dropwise trifluoroacetic acid (3 mL) and the mixture was stirred at ambient temperature for 4 hours. The mixture was concentrated and the solid was washed with ethyl acetate and dried under vacuum to give the title compound. $^1$H NMR (DMSO-d$_6$+D$_2$O, 300 MHz): δ 7.57-7.54 (m, 2H), 7.50-7.46 (m, 1H), 6.91 (d, J=8.7 Hz, 1H), 6.55 (s, 1H), 5.92-5.89 (m, 1H), 4.94 (s, 2H), 3.77 (s, 3H), 3.39 (q, J=7.2 Hz, 2H), 3.24-3.22 (m, 8H), 1.45 (t, J=7.2 Hz, 3H). MS: 555 (M+H$^+$).

EXAMPLE 58

5-(2-chlorobenzyl)-2-ethyl-7-{[2-methoxy-4-(piperazin-1-yl)phenyl]amino}imidazo[1,2-c]pyrimidine-8-carboxamide

EXAMPLE 58A tert-butyl 4-(4-(8-carbamoyl-2-ethyl-5-(methylthio)imidazo[1,2-f]pyrimidin-7-ylamino)-3-methoxyphenyl)piperazine-1-carboxylate A solution of the product of Example 13D (250 mg, 0.5 mmol) and 1-bromobutan-2-one (302 mg, 2.0 mmol) in N,N-dimethylformamide (10 mL) was heated at 80° C. for 12 hours. After cooling, 30 mL of water was added, and the mixture was neutralized with sodium bicarbonate solution, and extracted with ethyl acetate (3×30 mL). The combined organic phase was washed with brine, dried over anhydrous sodium sulfate, filtered, and concentrated. The residue was purified by flash chromatography on silica gel eluting with 100:1 dichloromethane/methanol to give the title compound. MS: 542 (M+H$^+$).

EXAMPLE 58B tert-butyl 4-(4-(8-carbamoyl-5-(2-chlorobenzyl)-2-ethylimidazo[1,2-f]pyrimidin-7-ylamino)-3-methoxyphenyl)piperazine-1-carboxylate A solution of the product of Example 58A (100 mg, 0.18 mmol), 1M (2-chlorobenzyl)zinc(II) bromide in tetrahydrofuran (1.8 mL, 1.8 mmol) and tetrakis(triphenylphosphine)palladium(0) (12 mg, 0.01 mmol) in tetrahydrofuran (5 mL) was stirred at 65° C. under nitrogen for 12 hours. The mixture was neutralized with ammonium chloride solution (15 mL) and extracted with ethyl acetate (3×30 mL). The combined organic phase was washed with brine, dried over anhydrous sodium sulfate, filtered, and concentrated. The residue was purified by flash chromatography on silica gel (200-300 mesh) eluting with 30/1 dichloromethane/methanol to give the title compound. MS: 620 (M+H$^+$).

EXAMPLE 58C 5-(2-chlorobenzyl)-2-ethyl-7-(2-methoxy-4-(piperazin-1-yl)phenylamino)imidazo[1,2-f]pyrimidine-8-carboxamide To a solution of the product of Example 58B (80 mg, 0.13 mmol) in dichloromethane (10 mL) was added trifluoroacetic acid (2 mL). After stirring at room temperature for 8 hours, the mixture was concentrated and purified by preparative HPLC using a gradient of 10/90 to 75/25 acetonitrile/water (containing 0.1% trifluoroacetic acid) to give the title compound as the hydrochloride salt. $^1$H NMR (DMSO-d$_6$, 300 MHz): δ 11.90 (s, 1H), 9.39 (br, 3H), 7.90 (s, 1H), 7.24-7.60 (m, 5H), 6.64 (s, 1H), 5.98 (d, 1H), 4.63 (s, 2H), 3.84 (s, 3H), 3.25 (m, 8H), 2.77 (m, 2H), 1.31 (t, 3H). MS: 520 (M+H$^+$)

EXAMPLE 59

5-(2-chlorobenzyl)-7-{[2-chloro-4-(piperidin-4-yl)phenyl]amino}-2-ethylimidazo[1,2-c]pyrimidine-8-carboxamide

EXAMPLE 59A tert-butyl 4-(4-(5-carbamoyl-6-chloro-2-(methylthio)pyrimidin-4-ylamino)-3-chlorophenyl)piperidine-1-carboxylate A solution of the product of Example 2D (238 mg, 1.0 mmol), the product of Example 60E (310 mg, 1.0 mmol) and N-ethyl-N-isopropylpropan-2-amine (258 mg, 2.0 mmol) in dioxane (10 mL) was heated in a sealed tube at 120° C. for 16 hours. Cooling and concentration provided the crude title compound which was used in the next step without further purification. MS: 512 (M+H$^+$).

EXAMPLE 59B tert-butyl 4-(4-(6-amino-5-carbamoyl-2-(methylthio)pyrimidin-4-ylamino)-3-chlorophenyl)piperidine-1-carboxylate A solution of the product of Example 59A (450 mg, 0.88 mmol) and 25% ammonia solution (1 mL) in dioxane (10 mL)

was heated in a sealed tube at 100° C. for 16 hours. After cooling and concentration, the residue was purified by flash chromatography on silica gel eluting with 30:1 dichloromethane:methanol to give the title compound. MS: 493 (M+H+).

EXAMPLE 59C tert-butyl 4-(4-(8-carbamoyl-2-ethyl-5-(methylthio) imidazo[1,2-f]pyrimidin-7-ylamino)-3-chlorophenyl) piperidine-1-carboxylate A solution of the product of Example 59B (200 mg, 0.4 mmol) and 1-bromobutan-2-one (302 mg, 2.0 mmol) in N,N-dimethylformamide (10 mL) was heated at 60° C. for 12 hours. After cooling, the mixture was diluted with water (30 mL), neutralized with sodium bicarbonate solution and extracted with ethyl acetate (3×30 mL). The combined organic layer was washed with brine, dried over anhydrous sodium sulfate, filtered, and concentrated. The residue was purified by flash chromatography on silica gel eluting with 30:1 dichloromethane:methanol to give the title compound. MS: 545 (M+H+).

EXAMPLE 59D tert-butyl 4-(4-(8-carbamoyl-5-(2-chlorobenzyl)-2-ethylimidazo[1,2-f]pyrimidin-7-ylamino)-3-chlorophenyl)piperidine-1-carboxylate A solution of the product of Example 59C (50 mg, 0.1 mmol), 1M (2-chlorobenzyl)zinc(II) bromide in tetrahydrofuran (1.0 mL, 1.0 mmol) and tetrakis(triphenylphosphine)palladium(0) (12 mg, 0.01 mmol) in tetrahydrofuran (5 mL) was stirred at 65° C. under nitrogen for 12 hours. The mixture was neutralized with ammonium chloride solution (15 mL) and extracted with ethyl acetate (3×30 mL). The combined organic layer was washed with brine, dried over anhydrous sodium sulfate, filtered, and concentrated. The residue was purified by flash chromatography on silica gel (200-300 mesh) eluting with 30/1 dichloromethane/methanol to give the title compound. MS: 623 (M+H+).

EXAMPLE 59E 7-(2-chloro-4-(piperidin-4-yl)phenylamino)-5-(2-chlorobenzyl)-2-ethylimidazo[1,2-f]pyrimidine-8-carboxamide To a solution of the product of Example 59D (45 mg, 0.07 mmol) in dichloromethane (10 mL) was added trifluoroacetic acid (2 mL). After stirring at room temperature for 8 hours, the mixture was concentrated and purified by preparative HPLC using a gradient of 10/90 to 75/25 acetonitrile/water (containing 0.1% trifluoroacetic acid) to give the title compound as the hydrochloride salt. $^1$H NMR (DMSO-$d_6$+$D_2O$, 300 MHz): δ 7.88 (s, 1H), 7.40-7.57 (m, 5H), 7.22 (s, 1H), 6.62 (d, 1H), 4.59 (s, 2H), 3.37 (m, 2H), 2.96 (m, 2H), 2.75 (m, 4H), 1.70-1.89 (m, 3H), 1.30 (t, 3H). MS: 523 (M+H+)

EXAMPLE 60

5-(2-chlorobenzyl)-7-{[2-chloro-4-(piperidin-4-yl)phenyl]amino}[1,2,4]triazolo[4,3-c]pyrimidine-8-carboxamide

EXAMPLE 60A

N,N-4-(4-(bis(tert-butoxy carbonyl)amino-4-bromo-2-chlorobenzenamine

A mixture of 4-bromo-2-chlorobenzenamine (25 g, 121 mmol), di-tert-butyl dicarbonate (66 g, 303 mmol) and anhydrous potassium carbonate (50 g, 363 mmol) in N,N-dimethylformamide (120 mL) was stirred at ambient temperature for 15 hours. The mixture was filtered, and the filtrate was partitioned between ethyl acetate and water. The aqueous phase was extracted with ethyl acetate (3×35 mL). The combined organic phase was washed with saturated brine, dried over sodium sulfate, filtered and concentrated. The residue was purified by flash chromatography on silica gel (200-300 mesh) eluting with 20/1 petroleum/ethyl acetate to provide the title compound.

EXAMPLE 60B tert-butyl 4-(4-(bis(tert-butoxycarbonyl)amino)-3-chlorophenyl)-5,6-dihydropyridine-1(2H)-carboxylate A mixture of the product of Example 60A (380 mg, 1.23 mmol), tert-butyl 4-(4,4,5,5-tetramethyl-1,3,2-dioxaborolan-2-yl)-5,6-dihydropyridine-1(2H)-carboxylate (380 mg, 1.23 mmol) and sodium carbonate (391 mg, 3.69 mmol) in 1,4-dioxane (8 mL) and water (2 mL) was degassed and heated at 80° C. for 16 hours. After cooling to ambient temperature and concentration, the residue was partitioned between ethyl acetate and water and the aqueous layer was extracted with ethyl acetate (3×35 mL). The combined organic phase was washed with saturated brine, dried over sodium carbonate, filtered and concentrated. The residue was purified by flash chromatography on silica gel (200-300 mesh) eluting with 8/1 petroleum/ethyl acetate to provide the title compound.

EXAMPLE 60C tert-butyl 4-(4-(bis(tert-butoxycarbonyl)amino)-3-chlorophenyl)piperidine-1-carboxylate A mixture of the product of Example 60B (4.39 g, 10.7 mmol) and 10% palladium on carbon in methanol (100 mL) was stirred under hydrogen at ambient temperature for 4 hours. The mixture was filtered through diatomaceous earth and concentrated. The crude title compound was used in the next step without further purification.

EXAMPLE 60D 2-chloro-4-(piperidin-4-yl)benzenamine

A mixture the product of Example 60C (100 mg) and trifluoroacetic acid (1 mL) in dichloromethane (4 mL) was stirred at ambient temperature for 3 hours. The mixture was concentrated and the crude title compound was used in the next step without further purification. MS: 211 (M+H+).

EXAMPLE 60E tert-butyl 4-(4-amino-3-chlorophenyl)piperidine-1-carboxylate

A mixture of the product of Example 60D (77 mg, 0.36 mmol), di-tert-butyl bicarbonate (80 mg, 0.37 mmol) and potassium carbonate (117 mg, 0.85 mmol) in N,N-dimethylformamide (4 mL) was stirred at ambient temperature until TLC indicated no starting material remained. The mixture was concentrated and the residue was purified by flash chromatography on silica gel (200-300 mesh) eluting with 8/1 petroleum/ethyl acetate to provide the title compound. MS: 310 (M+H$^+$).

EXAMPLE 60F tert-butyl 4-(4-(5-carbamoyl-6-chloro-2-(methylthio)pyrimidin-4-ylamino)-3-chlorophenyl)piperidine-1-carboxylate The title compound was obtained following the procedure described in Example 16E, using the product of Example 60E in place of the product of Example 16D. MS: 512 (M+H$^+$).

EXAMPLE 60G tert-butyl 4-(4-(5-carbamoyl-6-hydrazinyl-2-(methylthio)pyrimidin-4-ylamino)-3-chlorophenyl)piperidine-1-carboxylate The title compound was obtained following the procedure described in Example 16F, using the product of Example 60F in place of the product of Example 16E. MS; 508 (M+H$^+$).

EXAMPLE 60H tert-butyl 4-(4-(8-carbamoyl-5-(methylthio)-[1,2,4]triazolo[4,3-f]pyrimidin-7-ylamino)-3-chlorophenyl)piperidine-1-carboxylate The title compound was obtained following the procedure described in Example 16G, using the product of Example 60G in place of the product of Example 16F. MS: 518 (M+H$^+$).

EXAMPLE 60I tert-butyl 4-(4-(5-(2-chlorobenzyl)-8-carbamoyl-[1,2,4]triazolo[4,3-f]pyrimidin-7-ylamino)-3-chlorophenyl)piperidine-1-carboxylate The title compound was obtained following the procedure described in Example 19A, using the product of Example 60H in place of the product of Example 13E. MS: 596 (M+H$^+$).

EXAMPLE 60J 5-(2-chlorobenzyl)-7-(2-chloro-4-(piperidin-4-yl)phenylamino)-[1,2,4]triazolo[4,3-f]pyrimidine-8-carboxamide The title compound was obtained following the procedure described in Example 14I, using the product of Example 60I in place of the product of Example 14H. $^1$H NMR (CD$_3$OD, 300 MHz): δ 9.46 (s, 1H), 7.49 (m, 5H), 7.25 (m, 1H), 6.70 (m, 1H), 4.74 (s, 2H), 3.50 (m, 2H), 3.18 (m, 2H), 2.83 (m, 1H), 2.06 (m, 2H), 1.81 (m, 2H). MS: 492 (M+H$^+$).

EXAMPLE 61

5-(2-chlorobenzyl)-3-ethyl-7-{[2-methoxy-4-(piperazin-1-yl)phenyl]amino}[1,2,4]triazolo[4,3-c]pyrimidine-8-carboxamide

EXAMPLE 61A tert-butyl 4-(4-(8-carbamoyl-5-(2-chlorobenzyl)-3-ethyl-[1,2,4]triazolo[4,3-c]pyrimidin-7-ylamino)-3-methoxyphenyl)piperazine-1-carboxylate The title compound was obtained following the procedure described in Example 19A, using the product of Example 57A in place of the product of Example 13E. MS: 621 (M+H$^+$).

EXAMPLE 61B 5-(2-chlorobenzyl)-3-ethyl-7-(2-methoxy-4-(piperazin-1-yl)phenylamino)-[1,2,4]triazolo[4,3-c]pyrimidine-8-carboxamide The title compound was obtained following the procedure described in Example 57C, using the product of Example 61A in place of the product of Example 57B. $^1$H NMR (DMSO-d$_6$/D$_2$O, 300 MHz): δ 7.58-7.42 (m, 4H), 6.95 (d/=8.7 Hz, 1H), 6.57 (s, 1H), 5.91-5.86 (m, 1H), 4.81 (s, 2H), 3.80 (s, 3H), 3.41-3.39 (m, 2H), 3.25-3.24 (m, 8H), 1.46 (t, J=7.2 Hz, 3H), 1.26-1.21 (m, 2H). MS: 521 (M+H$^+$).

EXAMPLE 62

5-(2,3-dichlorobenzyl)-7-{[2-methoxy-4-(piperidin-4-yl)phenyl]amino}[1,2,4]triazolo[4,3-c]pyrimidine-8-carboxamide

EXAMPLE 62A tert-butyl 4-(4-amino-3-methoxyphenyl)-5,6-dihydropyridine-1(2H)-carboxylate A mixture of 4-bromo-2-methoxybenzenamine (1.21 g, 6.0 mmol), tert-butyl 4-(3,3,4,4-tetramethylborolan-1-yl)-5,6-dihydropyridine-1(2H)-carboxylate (1.95 g, 6.3 mmol), sodium carbonate (1.91 g, 18 mmol) and 1,1'-bis(diphenylphosphino)ferrocene]dichloropalladium(II) (0.22 g, 0.3 mmol) in dioxane (25 mL) and water (5 mL) was degassed with nitrogen and heated to 90° C. for 15 hours. After cooling to ambient temperature, the mixture was filtered, concentrated and purified by flash chromatography eluting with 200:1 dichloromethane:methanol to give the title compound. MS: 305 (M+H$^+$).

EXAMPLE 62B tert-butyl 4-(4-amino-3-methoxyphenyl)piperidine-1-carboxylate

To a mixture of 10% palladium on carbon (0.1 g) in methanol (30 mL) was added the product of Example 62A (0.8 g, 2.6 mmol) and the mixture was stirred at ambient temperature under hydrogen for 8 hours. The mixture was filtered and concentrated to yield the title compound. MS: 307 (M+H$^+$).

EXAMPLE 62C tert-butyl 4-(4-(8-carbamoyl-5-(methylthio)-[1,2,4]triazolo[4,3-c]pyrimidin-7-ylamino)-3-methoxyphenyl)piperidine-1-carboxylate The title compound was obtained following the procedure described in Example 17C-E, using the product of Example 62B in place of the product of Example 17B. MS: 514 (M+H$^+$).

EXAMPLE 62D tert-butyl 4-(4-(5-(2,3-dichlorobenzyl)-8-carbamoyl-[1,2,4]triazolo[4,3-f]pyrimidin-7-ylamino)-3-methoxyphenyl)piperidine-1-carboxylate The title compound was obtained following the procedure described in Example 14H, using the product of Example 62C in place of the product of Example 14G and (2,3-dichlorobenzyl)zinc(II) chloride in place of (2,6-dichlorobenzyl)zinc(II) chloride. MS: 626 (M+H$^+$).

EXAMPLE 62E 5-(2,3-dichlorobenzyl)-7-(2-methoxy-4-(piperidin-4-yl)phenylamino)-[1,2,4]triazolo[4,3-f]pyrimidine-8-carboxamide The title compound was obtained following the procedure described in Example 14I, using the product of Example 62D in place of the product of Example 14H. $^1$H NMR (CD$_3$OD, 300 MHz): δ9.40 (s, 1H), 7.65 (dd, J=2.1, 1.5 Hz, 1H), 7.48 (m, 1H), 7.39 (t, J=7.5 Hz, 1H), 7.26 (t, J=8.4 Hz, 1H), 6.82 (d, J=1.5 Hz, 1H), 6.41 (dd, J=8.7, 1.8 Hz, 1H), 4.81 (s, 2H), 3.91 (s, 3H), 3.54 (m, 2H), 3.15 (m, 2H), 2.84 (m, 1H), 2.05 (m, 2H), 1.89 (m, 2H). MS: 526 (M+H$^+$).

EXAMPLE 63

5-(2-fluorobenzyl)-7-{[2-methoxy-4-(piperidin-4-yl)phenyl]amino}[1,2,4]triazolo[4,3-c]pyrimidine-8-carboxamide

EXAMPLE 63A tert-butyl 4-(4-(5-(2-fluorobenzyl)-8-carbamoyl-[1,2,4]triazolo[4,3-f]pyrimidin-7-ylamino)-3-methoxyphenyl)piperidine-1-carboxylate The title compound was obtained following the procedure described in Example 14H, using the product of Example 62C in place of the product of Example 14G and (2-fluorobenzyl)zinc(II) chloride in place of (2,6-dichlorobenzyl)zinc(II) chloride. MS: 576 (M+H$^+$).

EXAMPLE 63B 5-(2-fluorobenzyl)-7-(2-methoxy-4-(piperidin-4-yl)phenylamino)-[1,2,4]triazolo[4,3-f]pyrimidine-8-carboxamide The title compound was obtained following the procedure described in Example 14I, using the product of Example 63A in place of the product of Example 14H. $^1$H NMR (CD$_3$OD, 300 MHz): δ 9.48 (s, 1H), 7.49 (m, 5H), 7.26 (s, 1H), 7.43 (d, J=8.1 Hz, 1H), 4.75 (s, 2H), 3.52 (m, 2H), 3.15 (m, 2H), 2.84 (m, 1H), 2.02 (m, 2H), 1.83 (m, 2H). MS: 476 (M+H$^+$).

EXAMPLE 64

5-(2,3-difluorobenzyl)-7-{[2-methoxy-4-(piperidin-4-yl)phenyl]amino}[1,2,4]triazolo[4,3-c]pyrimidine-8-carboxamide

EXAMPLE 64A tert-butyl 4-(4-(5-(2,3-difluorobenzyl)-8-carbamoyl-[1,2,4]triazolo[4,3-f]pyrimidin-7-ylamino)-3-methoxyphenyl)piperidine-1-carboxylate The title compound was obtained following the procedure described in Example 14H, using the product of Example 62C in place of the product of Example 14G and (2,3-difluorobenzyl)zinc(II) chloride in place of (2,6-dichlorobenzyl)zinc(II) chloride. MS: 594 (M+H$^+$).

EXAMPLE 64B 5-(2,3-difluorobenzyl)-7-(2-methoxy-4-(piperidin-4-yl)phenylamino)-[1,2,4]triazolo[4,3-f]pyrimidine-8-carboxamide The title compound was obtained following the procedure described in Example 14I, using the product of Example 64A in place of the product of Example 14H. $^1$H NMR (DMSO-d$_6$, 300 MHz): δ 12.26 (s, 1H), 9.50 (s, 1H), 8.95 (m, 1H), 8.84 (brs, 1H), 8.75 (brs, 1H), 7.89 (s, 1H), 7.51 (m, 1H), 7.30 (m, 3H), 6.81 (m, 1H), 6.34 (m, 1H), 4.74 (s, 2H), 3.86 (m, 3H), 3.38 (m, 2H), 2.99 (m, 2H), 2.76 (m, 2H), 1.83 (m, 5H). MS: 494 (M+H$^+$),

EXAMPLE 65

5-(2,6-dichlorobenzyl)-7-{[2-methoxy-4-(piperazin-1-yl)phenyl]amino}-2-(morpholin-4-ylmethyl)imidazo[1,2-c]pyrimidine-8-carboxamide

EXAMPLE 65A tert-butyl 4-(4-(8-carbamoyl-2-(chloromethyl)-5-(methylthio)imidazo[1,2-c]pyrimidin-7-ylamino)-3-methoxyphenyl)piperazine-1-carboxylate A mixture of the product of Example 13D (629 mg, 1.28 mmol) and 1,3-dichloropropan-2-one (652 mg, 5.13 mmol) in 1,2-dimethoxylethane (20 mL) was heated at 80° C. for 18 hours. The mixture was concentrated and the residue was purified by flash chromatography on silica gel (200-300 mesh) eluting with 97/3 dichloromethane/methanol to give the title compound. MS: 562 (M+H$^+$).

EXAMPLE 65B tert-butyl 4-(4-(8-carbamoyl-5-(methylthio)-2-(morpholinomethyl)imidazo[1,2-d]pyrimidin-7-ylamino)-3-methoxyphenyl)piperazine-1-carboxylate To a solution of the product of Example 65A (50 mg, 0.09 mmol) in 1,4-dioxane (5 mL) was added morpholine (23 mg, 0.3 mmol) and the mixture was stirred at 60° C. for 18 hours.

EXAMPLE 65C tert-butyl 4-(4-(8-carbamoyl-5-(2,6-dichlorobenzyl)-2-(morpholinomethyl)imidazo[1,2-c]pyrimidin-7-ylamino)-3-methoxyphenyl)piperazine-1-carboxylate The title compound was obtained following the procedure described in Example 14H, using the product of Example 65B in place of the product of Example 14G. MS: 725 (M+H$^+$).

EXAMPLE 65D 5-(2,6-dichlorobenzyl)-7-(2-methoxy-4-(piperazin-1-yl)phenylamino)-2-(morpholinomethyl)imidazo[1,2-d]pyrimidine-8-carboxamide The title compound was obtained following the procedure described in Example 14I, using the product of Example 65C in place of the product of Example 14H. $^1$H NMR (DMSO-d$_6$+D$_2$O, 300 MHz): δ8.16 (s, 1H), 7.58-7.47 (s, 3H), 7.08 (d, J=9.0 Hz, 1H), 6.54 (d, J=2.4 Hz, 1H), 5.90 (dd, J=9.0, 2.4 Hz, 1H), 4.73 (s, 2H), 4.41 (s, 2H), 3.94 (m, 2H), 3.75-3.67 (m, 5H), 3.43-3.39 (m, 2H), 3.21-3.12 (m, 10H). MS: 625 (M+H$^+$).

EXAMPLE 66 ethyl 8-carbamoyl-5-(2,6-dichlorobenzyl)-7-{[2-methoxy-4-(piperazin-1-yl)-phenyl]amino}imidazo[1,2-c]pyrimidine-2-carboxylate

EXAMPLE 66A ethyl 7-(4-(4-(tert-butoxycarbonyl)piperazin-1-yl)-2-methoxyphenylamino)-8-carbamoyl-5-(methylthio)imidazo[1,2-c]pyrimidine-2-carboxylate A mixture of the product of Example 13D (1 g, 2.0 mmol), ethyl 3-bromo-2-oxopropanoate (796 mg, 4.1 mmol) and acetic acid (2 drops) in dimethylformamide (20 mL) was heated at 60° C. for 16 hours. After cooling to ambient temperature, the mixture was poured into water and extracted with dichloromethane (2×100 mL). The combined organic phase was washed with brine, dried over sodium sulfate, filtered and concentrated. The residue was purified by flash chromatography on silica gel (200-300 mesh) eluting with 98/2 dichloromethane/methanol to give the title compound. MS: 586 (M+H$^+$).

EXAMPLE 66B ethyl 7-(4-(4-(tert-butoxycarbonyl)piperazin-1-yl)-2-methoxyphenylamino)-8-carbamoyl-5-(2,6-dichlorobenzyl)imidazo[1,2-d]pyrimidine-2-carboxylate The title compound was obtained following the procedure described in Example 14H, using the product of Example 66A in place of the product of Example 14G. MS: 698 (M+H$^+$).

EXAMPLE 66C ethyl 8-carbamoyl-5-(2,6-dichlorobenzyl)-7-(2-methoxy-4-(piperazin-1-yl)phenylamino)imidazo[1,2-c]pyrimidine-2-carboxylate The title compound was obtained following the procedure described in Example 14I, using the product of Example 66B in place of the product of Example 14H. $^1$H NMR (DMSO-d$_6$, 300 MHz): δ 12.16 (s, 1H), 9.47 (s, 1H), 9.12 (brs, 2H), 8.87-8.86 (m, 1H), 7.83 (brs, 1H), 7.65-7.62 (m, 2H), 7.56-7.50 (m, 1H), 7.13 (d, J=8.7 Hz, 1H), 6.61 (s, 1H), 5.96 (d, J=8.7 Hz, 1H), 4.90 (s, 2H), 4.43-4.36 (m, 2H), 3.82 (s, 3H), 3.31-3.24 (m, 8H), 1.39-1.35 (m, 3H). MS: 598 (M+H$^+$).

EXAMPLE 67

5-(2,6-dichlorobenzyl)-N$^2$-ethyl-7-{[2-methoxy-4-(piperazin-1-yl)phenyl]amino}imidazo[1,2-c]pyrimidine-2,8-dicarboxamide

EXAMPLE 67A 7-(4-(4-(tert-butoxycarbonyl)piperazin-1-yl)-2-methoxyphenylamino)-8-carbamoyl-5-(2,6-dichlorobenzyl)imidazo[1,2-c]pyrimidine-2-carboxylic acid A mixture of the product of Example 66B (280 mg, 0.4 mmol) in 4M aqueous lithium hydroxide (2 mL) and tetrahydrofuran (6 mL) was heated at 60° C. for 2 hours. The mixture was concentrated and the residue was dissolved in dichloromethane, washed with water and brine, dried over sodium sulfate, filtered and concentrated. The crude title compound was used in the next step with further purification. MS: 670 (M+H$^+$).

EXAMPLE 67B tert-butyl 4-(4-(8-carbamoyl-5-(2,6-dichlorobenzyl)-2-(ethylcarbamoyl)imidazo[1,2-c]pyrimidin-7-ylamino)-3-methoxyphenyl)piperazine-1-carboxylate To a solution of the product of Example 67A (50 mg, 0.07 mmol), (1-ethyl-3-3-dimethylaminopropyl)carbodiimide (22 mg, 0.11 mmol) and hydroxybenzotriazole (15 mg, 0.11 mmol) in dimethylformamide (5 mL) was added ethanamine hydrochloride (9 mg, 0.11 mmol) and N,N-diisopropylethylamine (27 mg, 0.21 mmol). The mixture was stirred at ambient temperature for 16 hours and concentrated. The residue was purified by flash chromatography on silica gel (200-300 mesh) eluting with 98/2 dichloromethane/methanol to give the title compound. MS: 697 (M+H$^+$).

EXAMPLE 67C 5-(2,6-dichlorobenzyl)-N$^2$-ethyl-7-{[2-methoxy-4-(piperazin-1-yl)phenyl]amino}imidazo[1,2-c]pyrimidine-2,8-dicarboxamide The title compound was obtained following the procedure described in Example 14 I using the product of Example 67B in place of the product of Example 14H. $^1$H NMR (DMSO-d$_6$+D$_2$O, 300 MHz): δ 8.48 (s, 1H), 7.61-7.58 (m, 2H), 7.53-7.50 (m, 1H), 7.13 (d, J=8.7 Hz, 1H), 6.58 (d, J=2.1 Hz, 1H), 5.94 (dd, J=2.1 Hz, J=9.0 Hz, 1H), 4.83 (s, 2H), 3.80 (s, 3H), 3.35-3.24 (m, 10H), 1.15 (t, J=6.9 Hz, 3H). MS: 597 (M+H$^+$).

EXAMPLE 68

5-(2,6-dichlorobenzyl)-7-{[2-methoxy-4-(piperazin-1-yl)phenyl]amino}-$N^2$-(2,2,2-trifluoroethyl)imidazo[1,2-c]pyrimidine-2,8-dicarboxamide

EXAMPLE 68A tert-butyl 4-(4-(8-carbamoyl-5-(2,6-dichlorobenzyl)-2-(2,2,2-trifluoroethylcarbamoyl)imidazo[1,2-c]pyrimidin-7-ylamino)-3-methoxyphenyl)piperazine-1-carboxylate The title compound was obtained following the procedure described in Example 67B using 2,2,2-trifluoroethylamine in place of ethanamine hydrochloride. MS: 751 ($M+H^+$).

EXAMPLE 68B 5-(2,6-dichlorobenzyl)-7-{[2-methoxy-4-(piperazin-1-yl)phenyl]amino}-$N^2$-(2,2,2-trifluoroethyl)imidazo[1,2-c]pyrimidine-2,8-dicarboxamide The title compound was obtained following the procedure described in Example 14I, using the product of Example 68A in place of the product of Example 14H. $^1$H NMR (DMSO-$d_6$, 300 MHz): δ 12.32 (s, 1H), 9.43-9.41 (m, 2H), 9.17 (brs, 2H), 8.73 (s, 1H), 7.81 (brs, 1H), 7.65-7.63 (m, 2H), 7.56-7.54 (m, 1H), 7.15 (d, J=8.7 Hz, 1H), 6.62 (s, 1H), 5.96 (dd, J=9.3, 1.5 Hz, 1H), 4.88 (s, 2H), 4.16-4.11 (m, 2H), 3.83 (s, 3H), 3.32-3.24 (m, 8H). MS: 651 ($M+H^+$).

EXAMPLE 69

Enzyme Inhibition Data

The following procedure is used to determine ALK Activity:

ALK kinase assays were conducted with the indicated final concentrations unless otherwise specified. In 384 well black plates (Axygen), 8 μl of compound (2% DMSO) was incubated with 8 μl Lck-peptide substrate (0.5 μM, biotin-Ahx-GAEEEIYAAFFA-COOH) and 8 μl of a mixture of ALK (3 nM, Millipore) and ATP (50 μM) in reaction buffer (50 mM Hepes, pH 7.4; 10 mM $MgCl_2$; 2 mM $MnCl_2$; 0.1 mM sodium orthovanadate; 0.01% BSA and 1 mM DTT (added fresh before assay) for 1 h at room temperature. Reactions were then quenched by the addition of 30 μl quench solution (streptavidin-allophycocyanin and Europium-cryptate PT66 monoclonal antibody in 40 mM Hepes, pH 7.4; 480 mM KF; 66 mM EDTA; 0.01% Tween-20; and 0.1% BSA) at room temperature. Plates were read 1 h after quenching on an Envision Multilaber Reader and $IC_{50}$ values were calculated using a sigmoidal fit of the concentration/inhibition response curves. These values were converted to apparent $K_i$ values using the Cheng-Prusoff relationship.

Alternatively, 4 nM ALK (Millipore) and 50 μM ATP were pre-incubated for 30 min at room temperate in 384 well plates (Corning 3676) in 2.5× reaction buffer (125 nM SEB from Cisbio Bioassays, 12.5 mM $MgCl_2$, 5 mM $MnCl_2$, and 2.5 mM DTT). Reactions were initiated by the addition of 4 μl ALK-ATP mixture to 2 μl compounds (2% DMSO) and 4 μl TK-substrate biotin (Cisbio Bioassays). After incubation for 1 h at room temperature, reactions were quenched in 10 μl stop buffer (Cisbio detection buffer containing Streptavididn-XL665 and Eu-Cryptate PT66 monoclonal antibody). Plates were read 1 h after quenching on an Envision Multilaber Reader and $IC_{50}$ values were calculated using a sigmoidal fit of the concentration/inhibition response curves. These values were converted to apparent $K_i$ values using the Cheng-Prusoff relationship.

Results are shown in Table 1

TABLE 1

| Example | HTRF ALK Human-$K_i$ |
|---|---|
| 1 | 0.001 |
| 2 | 0.0015 |
| 3 | <0.001 |
| 4 | 0.002 |
| 5 | 0.001 |
| 6 | 0.004 |
| 7 | 0.002 |
| 8 | 0.001 |
| 9 | <0.001 |
| 10 | 0.005 |
| 11 | 1.1 |
| 12 | 0.001 |
| 13 | 0.079 |
| 14 | 0.065 |
| 15 | <0.001 |
| 16 | 0.013 |
| 17 | <0.001 |
| 18 | <0.001 |
| 19 | 0.002 |
| 20 | <0.001 |
| 21 | 0.18 |
| 22 | 0.008 |
| 23 | 0.005 |
| 24 | 0.007 |
| 25 | <0.001 |
| 26 | <0.001 |
| 27 | <0.001 |
| 28 | <0.001 |
| 29 | <0.001 |
| 30 | 0.18 |
| 31 | 0.001 |
| 32 | 0.001 |
| 33 | 0.001 |
| 34 | 0.003 |
| 35 | 0.004 |
| 36 | 0.001 |
| 37 | 0.004 |
| 38 | <0.001 |
| 39 | 0.002 |
| 40 | <0.001 |
| 41 | <0.001 |
| 42 | <0.001 |
| 43 | 0.0015 |
| 44 | <0.001 |
| 45 | 0.004 |
| 46 | 0.015 |
| 47 | 0.002 |
| 48 | <0.001 |
| 49 | 0.001 |
| 50 | <0.001 |
| 51 | <0.001 |
| 52 | 0.057 |
| 53 | 0.001 |
| 54 | <0.001 |
| 55 | 0.002 |
| 56 | 0.002 |
| 57 | 0.002 |
| 58 | 0.018 |
| 59 | 0.002 |
| 60 | 0.001 |
| 61 | 0.011 |
| 62 | 0.002 |
| 63 | 0.008 |
| 64 | 0.006 |
| 65 | 0.077 |
| 66 | 0.001 |
| 67 | 0.013 |
| 68 | 0.12 |

Compounds of the present invention assessed by the above-described assays were found to have ALK kinase-inhibiting activity.

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A compound of formula (I):

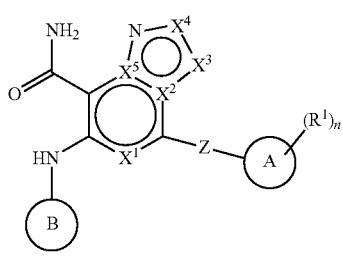

formula (I)

wherein $X^1$ and $X^3$ are N, $X^2$ and $X^5$ are C, and $X^4$ is $CR^{14}$;

A is phenyl, naphthyl, indenyl, $C_{3-8}$ cycloalkyl, 5-7 membered heterocycloalkyl, 5-7 membered heterocycloalkenyl, or 5-7 membered heteroaryl;

B is phenyl, pyridinyl, pyrimidinyl, pyrazinyl, pyridazinyl, or pyrazolinyl, wherein B is optionally susbstituted with one, two, three, or four $R^2$ and is substituted with $R^3$; or B is 1,2,3,4-tetrahydroisoquinoline;

Z is a bond, $C_{1-6}$ alkylene, or $C_{2-6}$ alkenylene;

$R^1$, at each occurrence, is independently selected from the group consisting of halo, CN, $NO_2$, $C_{1-6}$-alkyl, $C_{1-6}$-haloalkyl, aryl, $C_{3-8}$ cycloalkyl, heteroaryl, heterocycloalkyl, $OR^5$, $SR^5$, $C(O)R^5$, $C(O)NR^6R^7$, $C(O)OR^5$, $OC(O)R^5$, $OC(O)NR^6R^7$, $NR^6R^7$, $NR^6C(O)R^5$, $S(O)R^5$, $S(O)NR^6R^7$, $S(O)_2R^5$, $NR^6S(O)_2R^5$, and $S(O)_2NR^6R^7$; wherein the $C_{3-8}$ cycloalkyl, aryl, heterocycloalkyl, and heteroaryl are optionally substituted with 1, 2, or 3 substituents independently selected from halo, $C_{1-4}$ alkyl, $C_{1-4}$ haloalkyl, CN, $NO_2$, $OR^a$, $SR^a$, $C(O)R^a$, $C(O)NR^bR^c$, $C(O)OR^a$, $OC(O)R^a$, $OC(O)NR^bR^c$, $NR^bR^c$, $NR^bC(O)R^a$, $S(O)R^a$, $S(O)NR^bR^c$, $S(O)_2R^a$, $NR^bS(O)_2R^a$, and $S(O)_2NR^bR^c$;

$R^2$, at each occurrence, is independently selected from the group consisting of halo, CN, OH, $C_{1-4}$ alkyl, $C_{1-4}$-haloalkyl, $C_{1-4}$ alkoxy, $C_{1-4}$ haloalkoxy, $C_{1-4}$-thioalkoxy, -S(O)$C_{1-4}$ alkyl; amino, $C_{1-4}$ alkylamino, and $C_{1-4}$ dialkylamino;

$R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, heterocycloalkyl-$C_{1-6}$-alkyl-, $OR^8$, $C(O)R^8$, —$CH_2C(O)R^8$, $C(O)NR^9R^{10}$, $C(O)OR^8$, $OC(O)R^8$, $OC(O)NR^9R^{10}$, $NR^9R^{10}$, $NR^9C(O)R^8$, $S(O)R^8$, $S(O)NR^9R^{10}$, $S(O)_2R^8$, $NR^9S(O)_2R^8$, and $S(O)_2NR^9R^{10}$, wherein the $C_{3-8}$ cycloalkyl, aryl, heterocycloalkyl, and heteroaryl, alone or part of another moiety, are optionally substituted with one, two, or three $R^{11}$;

$R^4$ is H or $C_{1-6}$-alkyl;

$R^5$, $R^6$, and $R^7$, at each occurrence, are independently selected from H, $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety are optionally substituted with 1, 2, or 3 substituents independently selected from halo, CN, OH, $C_{1-4}$ alkyl, $C_{1-4}$-haloalkyl, $C_{1-4}$ alkoxy, $C_{1-4}$ haloalkoxy, amino, $C_{1-4}$ alkylamino, $C_{1-4}$ dialkylamino, C(O)OH, $C(O)C_{1-4}$ alkyl, $C(O)NH_2$, $C(O)NH(C_{1-4}$ alkyl), or $C(O)N(C_{1-4}$ alkyl)$_2$;

$R^8$, $R^9$, and $R^{10}$, at each occurrence, are independently selected from H, $C_{1-6}$ alkyl, $C_{1-6}$ haloalkyl, heteroaryl-$C_{1-6}$-alkyl-, heterocycloalkyl-$C_{1-6}$-alkyl-, $R^{12}R^{13}N$-$C_{1-6}$-alkyl-, aryl, $C_{3-8}$ cycloalkyl, heteroaryl, and heterocycloalkyl, wherein the aryl, $C_{3-8}$ cycloalkyl, heteroaryl, and heterocycloalkyl, alone or as part of another moiety, are optionally substituted with 1, 2, or 3 substituents independently selected from halo, CN, OH, $C_{1-4}$ alkyl, $C_{1-4}$-haloalkyl, $C_{1-4}$ alkoxy, $C_{1-4}$ haloalkoxy, amino, $C_{1-4}$ alkylamino, $C_{1-4}$ dialkylamino, C(O)OH, $C(O)C_{1-4}$ alkyl, $C(O)NH_2$, $C(O)NH(C_{1-4}$ alkyl), or $C(O)N(C_{1-4}$ alkyl)$_2$;

$R^{11}$, at each occurrence, is independently selected from the group consisting of halo, $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-$(C_{1-2}$ alkyl)-, $C_{3-8}$ cycloalkyl-$(C_{1-2}$ alkyl)-, heteroaryl-$(C_{1-2}$ alkyl)-, heterocycloalkyl-$(C_{1-2}$ alkyl)-, CN, $NO_2$, $OR^d$, $SR^d$, $C(O)R^d$, $C(O)NR^eR^f$, $C(O)OR^d$, $OC(O)R^d$, $OC(O)NR^eR^f$, $NR^eR^f$, $NR^eC(O)R^d$, $S(O)R^d$, $S(O)NR^eR^f$, $S(O)_2R^d$, $NR^eS(O)_2R^d$, and $S(O)_2NR^eR^f$, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl;

$R^{12}$ and $R^{13}$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^{14}$ is selected from the group consisting of H, $C_{1-6}$ alkyl, $C_{1-6}$ haloalkyl, —$C_{1-6}$ alkyl-heterocycloalkyl, —C(O)$OC_{1-6}$ alkyl, —C(O)$OC_{1-6}$ haloalkyl, —C(O)$NHC_{1-6}$ alkyl, —C(O)$NHC_{1-6}$ haloalkyl;

$R^a$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^b$ and $R^c$, at each occurrence, are independently selected from the group consisting of H, $C_{1-6}$ alkyl, $C_{1-6}$ haloalkyl, aryl, $C_{3-8}$ cycloalkyl, heteroaryl, heterocycloalkyl;

$R^d$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^e$ and $R^f$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl; and n is 0, 1, 2, or 3;

or a pharmaceutically acceptable salt or solvate thereof.

2. The compound of claim 1 of formula (I) wherein Z is —$CH_2$—, —$CH_2CH_2$—, —$CH(CH_3)$—, or —$C(CH_3)_2$—.

3. The compound of claim 1 of formula (I) wherein Z is —CH(=CH₂)— or —CH=CH—.

4. The compound of claim 1 of formula (I) wherein Z is a bond.

5. The compound of claim 1 of formula (I) wherein A is phenyl.

6. The compound of claim 5 of formula (I) wherein
n is 0, 1, or 2; and
$R^1$ is halo, $OR^5$, $C_{1-6}$ alkyl, $C_{1-6}$ haloalkyl, or CN.

7. The compound of claim 5 of formula (I) wherein
n is 1;
$R^1$ is $C(O)NR^6R^7$, $C(O)OR^5$, $NR^6C(O)R^5$, $NR^6S(O)_2R^5$, or $S(O)_2NR^6R^7$.

8. The compound of claim 1 of formula (I) wherein A is a 5-7 membered heteroaryl selected from the group consisting of include furanyl, thiophenyl, pyrrolyl, imidazolyl, pyrazoyl, triazolyl, tetrazolyl, oxazolyl, isoxazolyl, thiazolyl, isothiazolyl, thiodiazolyl, oxadiazolyl, oxatriazolyl, dioxazolyl, oxathiazolyl, oxathiolyl, pyridinyl, pyridazinyl, pyrimidinyl, and pyrazinyl.

9. The compound of claim 1 of formula (I) wherein B is phenyl.

10. The compound of claim 9 of formula (I) wherein $R^3$ is heterocycloalkyl.

11. The compound of claim 1 of formula (I) wherein B is

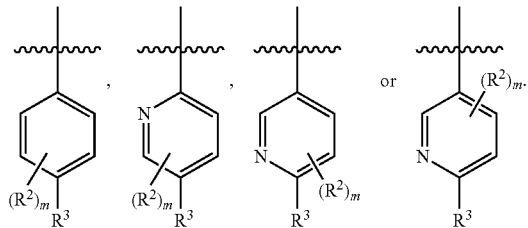

12. The compound of claim 11 of formula (I) wherein
m is 0 or 1;
$R^2$ is halo, $C_{1-4}$ alkyl, or $C_{1-4}$ alkoxy;
$R^3$ is

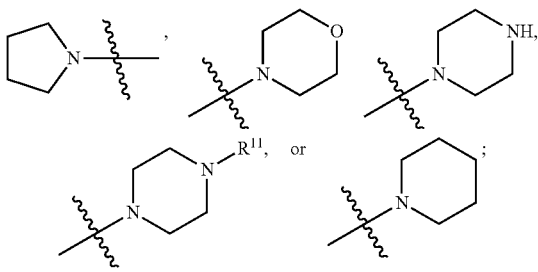

and
$R^{11}$ is $C_{1-4}$ alkyl, $C_{1-4}$ haloalkyl, amino-$C_{1-4}$-alkyl-, $C_{1-4}$alkylamino-$C_{1-4}$ alkyl-, $C_{1-4}$ dialkylamino-$C_{1-4}$ alkyl-, and hydroxy-$C_{1-4}$-alkyl-, $C_{1-4}$ alkyl-$C_{1-4}$ alkoxy, aryl, cycloalkyl, heteroaryl, heterocycloalkyl, aryl-($C_{1-2}$ alkyl)-, cycloalkyl-($C_{1-2}$ alkyl)-, heteroaryl-($C_{1-2}$ alkyl)-, or heterocycloalkyl-($C_{1-2}$ alkyl)-, wherein the aryl, cycloalkyl, heteroaryl, and heterocycloalkyl, alone or as part of another moiety, are optionally substituted with 1, 2, or 3 substituents independently selected from halo and $C_{1-4}$ alkyl.

13. The compound of claim 1 of formula (I) or a salt or a solvate thereof selected from the group consisting of
4-(2,6-dichlorobenzyl)-6-{[2-methoxy-4-(piperazin-1-yl)phenyl]amino}-1H-imidazo[4,5-c]pyridine-7-carboxamide;
6-{[3-chloro-4-(piperazin-1-yl)phenyl]amino}-4-(2,6-dichlorobenzyl)-1H-imidazo[4,5-c]pyridine-7-carboxamide;
4-(2,6-dichlorobenzyl)-6-{[2,5-difluoro-4-(piperazin-1-yl)phenyl]amino}-1H-imidazo[4,5-c]pyridine-7-carboxamide;
4-(2,6-dichlorobenzyl)-6-{[4-(piperazin-1-yl)-2-(trifluoromethyl)phenyl]amino}-1H-imidazo[4,5-c]pyridine-7-carboxamide;
4-(2,6-dichlorobenzyl)-6-{[2-methyl-4-(piperazin-1-yl)phenyl]amino}-1H-imidazo[4,5-c]pyridine-7-carboxamide;
4-(2,6-dichlorobenzyl)-6-{[3-methyl-4-(piperazin-1-yl)phenyl]amino}-1H-imidazo[4,5-c]pyridine-7-carboxamide;
4-(2,6-dichlorobenzyl)-6-{2-methoxy-4-[2-oxo-2-(pyrrolidin-1-yl)ethyl]phenyl}amino)-1H-imidazo[4,5-c]pyridine-7-carboxamide;
4-(2,6-dichlorobenzyl)-6-[(4-{[2-(dimethylamino)ethyl]carbamoyl}-2-methoxyphenyl)amino]-1H-imidazo[4,5-c]pyridine-7-carboxamide;
4-(2,6-dichlorobenzyl)-6-({2-methoxy-4-[(4-methylpiperazin-1-yl)carbonyl]phenyl}amino)-1H-imidazo[4,5-c]pyridine-7-carboxamide;
4-(2,6-dichlorobenzyl)-6-{[2-fluoro-4-(piperazin-1-yl)phenyl]amino}-1H-imidazo[4,5-c]pyridine-7-carboxamide;
4-(2,6-dichlorobenzyl)-6-{[2-methoxy-4-(piperazin-1-ylcarbonyl)phenyl]amino}-1H-imidazo[4,5-c]pyridine-7-carboxamide;
4-(2,6-dichlorobenzyl)-6-{[3,5-dichloro-4-(piperazin-1-yl)phenyl]amino}-1H-imidazo[4,5-c]pyridine-7-carboxamide;
4-(2,6-dichlorobenzyl)-6-{[3,5-difluoro-4-(piperazin-1-yl)phenyl]amino}-1H-imidazo[4,5-c]pyridine-7-carboxamide;
6-{[2-chloro-4-(piperazin-1-yl)phenyl]amino}-4-(2,6-dichlorobenzyl)-1H-imidazo[4,5-c]pyridine-7-carboxamide;
4-(2,6-dichlorobenzyl)-6-{[3-fluoro-2-methoxy-4-(piperazin-1-yl)phenyl]amino}-1H-imidazo[4,5-c]pyridine-7-carboxamide;
4-(2,6-dichlorobenzyl)-6-{[4-(piperazin-1-yl)-3-(trifluoromethyl)phenyl]amino}-1H-imidazo[4,5-c]pyridine-7-carboxamide;
4-(2,6-dichlorobenzyl)-6-{[4-(piperazin-1-yl)-2-(trifluoromethoxy)phenyl]amino}-1H-imidazo[4,5-c]pyridine-7-carboxamide;
4-(2,6-dichlorobenzyl)-6-{[2-methoxy-5-(piperazin-1-yl)phenyl]amino}-1H-imidazo[4,5-c]pyridine-7-carboxamide;
4-(2,6-dichlorobenzyl)-6-{[4-(hexahydropyrrolo[1,2-a]pyrazin-2(1H)-yl)-2-methoxyphenyl]amino}-1H-imidazo[4,5-c]pyridine-7-carboxamide;
4-(2,6-dichlorobenzyl)-6-{[2,3-dimethyl-4-(piperazin-1-yl)phenyl]amino}-1H-imidazo[4,5-c]pyridine-7-carboxamide;
4-(2,6-dichlorobenzyl)-6-{[2-methoxy-4-(pyrrolidin-1-ylmethyl)phenyl]amino}-1H-imidazo[4,5-c]pyridine-7-carboxamide;

4-(2,6-dichlorobenzyl)-6-{[2-fluoro-5-methyl-4-(piperazin-1-yl)phenyl]amino}-1H-imidazo[4,5-c]pyridine-7-carboxamide;

4-(2,6-dichlorobenzyl)-6-{[3,5-difluoro-2-methoxy-4-(piperazin-1-yl)phenyl]amino}-1H-imidazo[4,5-c]pyridine-7-carboxamide;

4-(2,6-dichlorobenzyl)-6-[(6-methoxy-1,2,3,4-tetrahydroisoquinolin-7-yl)amino]-1H-imidazo[4,5-c]pyridine-7-carboxamide; and 6-{[2-chloro-4-(piperidin-4-yl)phenyl]amino}-4-(2,6-dichlorobenzyl)-1H-imidazo[4,5-c]pyridine-7-carboxamide.

14. A pharmaceutical composition comprising a compound or pharmaceutically acceptable salt of claim 1 and pharmaceutically acceptable excipient.

\* \* \* \* \*

UNITED STATES PATENT AND TRADEMARK OFFICE
CERTIFICATE OF CORRECTION

PATENT NO. : 9,212,192 B2
APPLICATION NO. : 13/979387
DATED : December 15, 2015
INVENTOR(S) : Vasudevan et al.

It is certified that error appears in the above-identified patent and that said Letters Patent is hereby corrected as shown below:

In the claims

Column 109, line 58, claim 1: "alkyl;" to read as --alkyl,--

Column 111, line 15, claim 8: "consisting of include" to read as --consisting of--

Column 111, line 35, claim 11: " 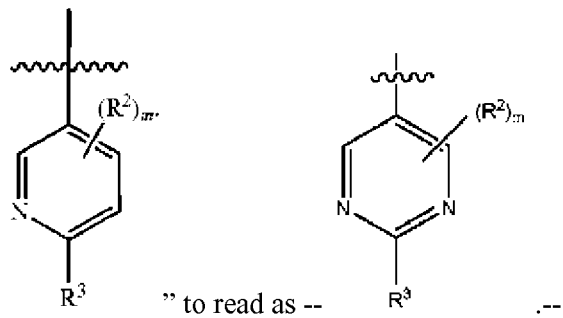 " to read as --            .--

Column 112, line 22, claim 13: "6-{2-methoxy" to read as --6-({2-methoxy--

Signed and Sealed this
Fifth Day of July, 2016

Michelle K. Lee
*Director of the United States Patent and Trademark Office*